(12) United States Patent
Pawelek et al.

(10) Patent No.: US 6,685,935 B1
(45) Date of Patent: Feb. 3, 2004

(54) VECTORS FOR THE DIAGNOSIS AND TREATMENT OF SOLID TUMORS INCLUDING MELANOMA

(75) Inventors: John M. Pawelek, Hamden, CT (US); David Bermudes, Wallingford, CT (US); Kenneth Brooks Low, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/358,052

(22) Filed: Jul. 21, 1999

Related U.S. Application Data

(63) Continuation of application No. 08/658,034, filed on Jun. 4, 1996, now Pat. No. 6,190,657, which is a continuation-in-part of application No. 08/486,422, filed on Jun. 7, 1995, now abandoned.

(51) Int. Cl.$^7$ .................. A01N 63/00; A61K 45/00; C12Q 1/00; C12N 1/00; C07H 21/00

(52) U.S. Cl. .................. 424/93.2; 424/282.1; 435/4; 435/243; 536/23.1

(58) Field of Search .................. 424/93.1, 93.2, 424/282.1; 435/4, 69.1, 243, 252.3; 436/543; 536/23.1

(56) References Cited

U.S. PATENT DOCUMENTS

| | | |
|---|---|---|
| 4,436,727 A | 3/1984 | Ribi |
| 5,021,234 A | 6/1991 | Ehrenfeld |
| 5,344,762 A | 9/1994 | Karapetian |
| 5,830,702 A | 11/1998 | Portnoy et al. |
| 6,051,237 A | 4/2000 | Paterson |

FOREIGN PATENT DOCUMENTS

| | | | |
|---|---|---|---|
| EP | 0 564 121 A2 | 3/1993 | |
| JP | 06046890 A * | 2/1994 | ............. 436/501 |
| WO | WO 92/11361 | 7/1992 | |
| WO | WO 92/15689 | 9/1992 | |
| WO | WO 95/02048 | 1/1995 | |
| WO | WO 95/05835 | 3/1995 | |
| WO | WO 96/11277 | 4/1996 | |

OTHER PUBLICATIONS

Bast Antitumor activity of bacterial infection. II Effect of *Listerial monocytogenes* on growth of a murine fibrosarcoma. J. Natl Cancer Inst. vol. 54(3):757–761, 1975.*

Bast Antitumor activity of bacterial infection. I Effect of *Listeria monocytogenes* on growth of a murine fibrosarcoma. J. Natl. Cancer Inst. vol. 54(3):749–756, 1975.*

North et al. T–cell mediated concomitant immunity to sygeneic tumors. I Activated macrophages as the expressors of nonspecific immunity to unrelated tumors and bacterial parasites. J. Exp. Med. vol. 145(2):275–292, 1977.*

Youdim et al. Resistance to tumor growth mediated by *Listeria monocytogenes*: collaborative and suppressive macrophage–lymphocyte interactions in vitro. J. Immunol. vol. 117(5pt2)1860–1865, 1976.*

Youdim Resistance to tumor growth mediated by *Listeria monocytogenes*. Destruction of experimental malignant melanoma by LM–activated peritoneal and lymphoid cells. J. Immunol. vol. 116(3)579–584, 1976.*

Youdim et al. Nonspecific suppression of tumor growth by an immune reaction to *Listeria monocytogenes*. J. Natl. Cancer Inst. vol. 52(1)193–198, 1974.*

Youdim et al. Cooperation of immune lymphoid and reticuloendothelial cells during *Listeria monocytogenes*–mediated tumor immunity. Cancer Res. vol. 37(4)991–996, 1977.*

Eisenstein et al. Immunotherapy of a plasmacytoma with attenuated salmonella. Medical Oncology. vol. 12:103–108, Jan. 1995.*

Pidherney et al. In vitro and in vivo tumoricidal properties of a pathogenic/free–living amoeba. Cancer Lett. vol. 72:91–98, Jan. 1995.*

Alizadeh et al. Apoptosis as a mechanism of cytolysis of tumor cells by a pathogenic free–living amoeba. Infect. Immun. vol. 62(4):1298–1303, Apr. 1994.*

Sakamoto et al. Antitumor effect of mromal intestinal microflora on Ehrlich ascites tumor. Jpn. J. Cancer Res. (Gann) vol. 79:109–116, Jan. 1988.*

Bast RC Jr et al., "Antitumor activity of bacterial infection. II. effect of *Listeria monocytogenes* on growth of a guinea pig hepatoma", J Natl Cancer Inst. Mar. 1975; 54(3):757–61.

Bast RC Jr, "Antitumor activity of bacterial infection. I. Effect of *Listeria monocytogenes* on growth of a murine fibrosarcoma", J Natl Cancer Inst. Mar. 1975; 54(3):749–56.

Hibbs et al., Role of activated macrophages in nonspecific resistance to neoplasia, J Reticuloendothel Soc. Sep. 1976; 20(3):223–31.

Keller R, "Resistance to a non–immunogenic tumor, induced by *Corynebacterium parvum* or *Listeria monocytogenes*, is abrogated by anti–interferon gamma", Int J Cancer. Oct. 15, 1990; 46(4):687–90.

Koshimura et al., "On the streptolysis S synthetizing and anticancer activities of cell–free extract from living hemolytic streptococci", Cncer Chemo. 13:107, Jul., 1961.

(List continued on next page.)

*Primary Examiner*—Remy Yucel
*Assistant Examiner*—William Sandals
(74) *Attorney, Agent, or Firm*—Pennie & Edmonds LLP

(57) ABSTRACT

The present invention is directed to the isolation and use of super-infective, tumor-specific vectors that are strains of parasites including, but not limited to bacteria, fungi and protists. In certain embodiments the parasites include, but are not limited to, the bacterium Salmonella spp., such as *Salmonella typhimurium*, the bacterium *Mycobacterium avium* and the protozoan *Leishmania amazonensis*. In other embodiments, the present invention is concerned with the isolation of super-infective, tumor-specific, suicide gene-containing strains of parasites for use in treatment of solid tumors.

188 Claims, 37 Drawing Sheets

OTHER PUBLICATIONS

Mizutani and Mitsuoka, 1980, "Inhibitory Effect of Some Intestinal Bacteria on Liver Tumorigenesis in Gnotobiotic C3H/He Male Mice," Cancer Letter 11:89–96.

Murata et al., 1965, "Oncolytic Effect of Proteus Mirabilis Upon Tumor Bearing Animal," Life Science 4:1055–67.

North et al., "T–cell–mediated concomitant immunity to syngeneic tumors. I. Activated macrophages as the expressors of nonspecific immunity to unrelated tumors and bacterial parasites", J Exp Med. Feb. 1, 1977; 145(2):275–92.

Reilly CH, "Microbiology and cancer therapy: A Review", Cancer Res. 13(12): 821, Dec. 1953.

Youdim et al., "Resistance to tumor growth mediated by *Listeria monocytogenes*: collaborative and suppressive macrophage–lymphocyte interactions in vitro", J Immunol. Nov. 1976; 117(5 Pt.2):1860–5.

Youdim S, "Resistance to tumor growth mediated by Listeria monocytogenes. Destruction of experimental malignant melanoma by LM–activated peritoneal and lymphoid cells", J Immunol. Mar. 1976; 116(3):579–84.

Youdim, S, et al., "Nonspecific suppression of tumor growth by an immune reaction to *Listeria monocytogenes*", J Natl Cancer Inst. Jan. 1974; 52(1):193–8.

Youdim.et al., "Cooperation of immune lymphoid and reticuloendothelial cells during *Listeria monocytogenes*–mediated tumor immunity", Cancer Res. Apr. 1977; 37(4):991–6.

Zinkernagel RM, "Early appearance of sensitized lymphocytes in mice infected with *Listeria monocytogenes*", J Immunol. Feb. 1974; 112(2):496–501.

J. Adler, 1973, "A method of measuring chemotaxis and use of the method to determine optimum conditions for chemotaxis by *Escherichia coli*", J Gen Microbiol 74:77–91.

Alizadeh et al., 1994, "Apoptosis as a mechanism of cytosis of tumor cells by a pathogenic free–living amoeba", *Infect Immun 62*:1298–1303.

K. Bagshawe, 1995, "Antibody–directed enzyme prodrug therapy: A review", *Drug Dev Res 34*:220–230.

Barry et al., 1995, "Protection against mycoplasma using expression library immunization", *Nature 377*:632–635.

Barth and Morton, 1995, "The role of adjuvant therapy in melanoma management", *Cancer 75 (Suppl.2)*:726–734.

R. Berggren, 1995, "Recombinant salmonella as an oral HIV vaccine", NIH project No. 5 K01 AI01248–02.

R. Bone, 1993, "Gram–negative sepsis: A dilemma of modern medicine", *Clin Microbiol Rev 6*:57–68.

Bonnekoh et al., 1995, "Inhibition of melanoma growth by adenoviral–mediated HSV thymidine kinase gene transfer in vivo", *J Invest Derm 104*:313–317.

Carey et al., "Clostridial oncolysis in man", Eur. J. Cancer 3:37–46, 1986.

Carrier et al, 1996, "Expression of human IL–1β in *Salmonella typhimurium*; a model system for the delivery of recombinant therapeutic proteins in vivo", J. Immunology 148:1176–1181.

Carswell et al., 1975, "An endotoxin–induced serum factor that causes necrosis of tumors", *Proc Natl Acad Sci 72*:3666–3669.

Chabalgoity et al., 1996, "A *Salmonella typhimurium* htrA live vaccine expressing multiple copies of a peptide comprising amino acids 8–23 of herpes simplex virus glycoprotein D as a genetic fusion to tetanus toxin fragment C protects mice from herpes simplex virus infection", Microbiol. 19:791–801.

Christ et al., 1995, "E5531, a pure endotoxin antagonist of high potency", *Science* 268:80–83.

J. Clements, 1995, "Attenuated salmonella as vaccine vectors", *Science* 268:80–83.

Cunningham et al., 1992, "Actin–binding protein requirement for cortical stability and efficient locomotion", *Science 255*:326–327.

R. Curtiss, 1995, "Biological containment of live bacterial vaccines", NIH project No. 1 R41 AI38599–01.

R. Curtiss, 1994, "Avirulent salmonella host–vector vaccine systems", NIH project No. 1 R41 AI36585–01.

E. Eidenstadt, 1987, "Analysis of mutagenesis", from *Escherichia coli and Salmonella typhimurium, Cellular and Molecular Biology,* Neidhardt et al. (ed.), pp. 1016–1033.

Engelbart and Gericke, 1963, "Oncolysis by Clostridia. V. Transplanted tumors of the hamster", 1963, Cancer Research 24:239–243.

S. Falkow, 1991, "Bacterial entry into eukaryotic cells", *Cell 65*:1099–1102.

Fox, et al., 1996, "Anaerobic bacteria as a delivery system for cancer gene therapy: in vitro activation of 5–fluorocytosine by genetically engineered Clostridia", Gene Therapy 3:173–178.

S. Friberg, 1993, "BCG in the treatment of superficial cancer of the bladder: A review", *Med Oncol Tumor Pharmacother 10*:31–36.

J. Galan, 1995, "Novel Salmonella antigen delivery vectors", NIH project No. 5 R01 AI36520–02.

Gericke and Engelbart, 1963, "Oncolysis by Clostridia. II. Experiments on a tumor spectrum with a variety of Clostridia in combination with heavy metal", Cancer Research 24:217–221.

P. Gulig, 1994, "*Salmonella typhimurium* virulence plasmid", NIH project No. 5 R29 AI28421–05.

Hall et al., 1994, "Induced regression of bovine papillomas by intralesional immunotherapy", Therapeutic Immunol. 1:319–324.

Han et al., 1967, "Salmonellosis in disseminated malignant diseases", *New Eng J Med* 276(11):1045–1052.

R. Jain, 1994, "Barriers to Drug Delivery in Solid Tumors", *Scientific American 7*:58–65.

Jones et al., 1992, "Invasion by *Salmonella typhimurium* is affected by the direction of flagellar rotation", *Infect Immun 60*:2475–2480.

Karow and Georgopoulos, 1992, "Isolation and characterization of the *Escherichia coli* msbB gene, a multicopy suppressor of Null mutations in the high–temperature requirement gene htrB", J. Bacteriology 174:702–710.

Klimpel et al., 1990, "Bacteria–infected fibroblasts have enhanced susceptibility to the cytotoxic action of tumor necrosis factor", *J Immunol 145*:711–717.

Lee et al., 1992, "Identification of a *Salmonella typhimurium* invasion locus by selection for hyperinvasive mutants", *Proc Natl Acad Sci 89*:1847–1851.

Lemmon et al., 1994, "Anaerobic bacteria as a gene delivery system to tumors", Proc. Am. Assn. Cancer Research 35:374 (Abstract 2231).

M. Levine, 1995, "Recombinant and live oral *salmonella typhi* vaccines", NIH project No. 5 R01 AI29471–06.

Loppnow et al., 1990, "Cytokine induction by lipopolysaccharide (LPS) corresponds to lethal toxicity and is inhibited by nontoxic *Rhodobacter capsulatus* LPS", *Infect Immun 58*:3743–3750.

Lytvyn et al., 1992, "Comparison of the thymidine kinase genes from three entomopoxviruses", J. Gen. Virol. 73:3235–3240.

R. Macnab, 1992, "Genetics and biogenesis of bacterial flagella", Ann Rev Genet 26:131–158.

Mahan et al., 1993, "Selection of bacterial virulence genes that are specifically induced in host tissues".

McLaughlin et al., 1979, "Synergistic activity of components of mycobacteria and mutant Salmonella in causing regression of line–10 tumors in guinea pigs", Cancer Research 39:1766–1771.

S. Michalek, 1994, "Genetically engineered oral vaccines and caries immunity", Abstract, NIH project No. 5 R01 DE09081–05.

Miller et al., 1989, "A two–component regulatory system (phoP phQ) controls Salmonella typhimurium virulence", Proc Natl Acad Sci 86:5054–5058.

V. Miller, 1995, "Entry into eukaryotic cells by salmonella and yersinia", NIH project No. 5 K04 AI01230–02.

Miller et al., 1992, "An unusual pagC::TnphoA mutation leads to an invasion and virulence–defective phenotype in Salmonellae", Infect Immun 60:3763–3770.

Minton et al, 1995, "Chemotherapeutic tumour targeting using Clostridial spores", FEMS Micro. Rev. 17:357–364.

Möse and Möse, 1963, "Oncolysis by Clostridia. I. Activity of Clostidium butyricum (M–55) and other nonpathogenic Clostridia against the Ehrlich carcinoma", Cancer Research 24:212–216.

Mullen et al., 1992, "Transfer of the bacterial gene for cytosine deaminase to mammalian cells confers lethal sensitivity to 5–fluorocytosine: a negative selection system", PNAS (USA) 89:171–176.

Nauts et al., 1953, "A review of the influence of bacterial infection and of bacterial products (Coley's toxins) on malignant tumors in man", Acta Medica Scandinavica 145 (Suppl. 276):1–105.

Pan et al., 1995, "A recombinant Listeria Monocytogenes vaccine expressing a model tumour antigen protects mice against lethal tumour cell challenge and causes regression of established tumours", Nature Medicine 1:471–477.

Parker et al., "Effect of histiocyticus infection and toxin on transplantable mouse tumors", 1947, Pro. Soc. Exp. Biol. Med. 16124:461–467.

Pawelek et al., 1995, "Macrophage characteristics of metastatic melanoma", J Invest Dermatol 104:605 (Abstract 304).

Pidherney et al., 1993, "In vitro and in vivo tumoricidal properties of a pathogenic free–living amoeba", Cancer Letters 72:91–98.

A. Pugsley, 1988, "Protein secretion across the outer membrane of gram–negative bacteria" In: Protein Transfer and Organelle Biogenesis, Dand and Robbins (eds.), Academic Press, Inc., Harcourt Brace Jovanovich, Publishers, San Diego, pp. 607–652.

Raue and Cashel, 1975, "Regulation of RNA synthesis in Escherichia coli", Biochimica et Biophysica Acta 383:290–304.

Reinhard et al., 1950, "Chemotherapy of malignant neoplastic diseases", JAMA 142(6):383–390.

Saltzman et al., 1996, "Attenuated Salmonella typhimurium containig interleukin–2 decreases MC–38 hepatic metastases: a novel anti–tumor agent", Cancer Biotherapy and Radiopharmaceuticals 11:145–153.

Schafer et al., 1992, "Induction of a cellular immune response to a foreign antigen by a recombinant Listeria monocytogenes vaccine", J. Immunnol. 149:53.

Schlechte and Elbe, 1988, "Recombinant plasmid DNA variation of Clostridium oncolyticum—model experiments of cancerostatic gene transfer", Zbl. Bakt. Hyg. A 268:347–356.

Schlechte et al., 1982, "Chemotherapy for tumours using Clostridial oncolysis, antibiotics and cyclophosphamide: model trial on the UVT 15264 tumour", Arch. Geschwulstforsch 52:41–48.

Shaw et al., 1991, "The human dioxin–inducible NAD(P)H: quinone oxidoreductase cDNA–encoded protein expressed in COS–1 cells is identical to diaphorase 4", Eur. J. Biochem. 195:171–176.

Sizemore et al., 1995, "Attenuated Shigella as a DNA Delivery Vehicle for DNA–Mediated Immunization", Science 270:299–302.

Slauch et al., 1994, "In vivo expression technology for selection of bacterial genes specifically induced in host tissues", Meth Enzymol 235:481–492.

Somerville et al., "A novel Escherichia coli lipid A mutant that produces an antiinflammatory lipopolysaccharide", J. Clin. Invest. 97:359–365.

Sosnowski et al., 1994, "Complications of bacillus calmette–guerin (BCG) immunotherapy in superficial bladder cancer", Comp Ther 20:695–701.

Su et al., 1992, "Extracellular export of Shiga toxin B–subunit/haemolysin A (C–terminus) fusion protein expressed in Salmonella typhimurium aroA–Mutant and stimulation of B–subunit specific antibody responses in mice", Microbial Pathogenesis 13:465–476.

Takayma et al., 1989, "Diphosphoryl lipid A from Rhodopseudomonas sphaeroides ATCC 17023 blocks induction of cachectin in macrophages by lipopolysaccharide", Infect Immun 57:1336–1338.

Thiele et al., 1963, "Oncolysis by Clostidia. III. Effects of Clostridia and chemotherapeutic agents on rodent tumors", Cancer Research 24:222–232.

Thiele et al., 1963, "Oncolysis by Clostridia. IV. Effect of nonpathogenic Clostridial spores in normal and pathological tissues", 1963, Cancer Research 24:234–238.

Tuomanen, 1993, "Subversion of leukocyte adhesion systems by respiratory pathogens", Am Soc Microbiol 59:292–296.

Vinopal, 1987, "Selectable phenotypes", from Escherichia coli and Salmonella typhimurium, Cellular and Molecular Biology, Neidhardt et al. (ed.), pp. 990–1015.

Wolfe et al., 1971, "Salmonellosis in patients with neoplastic disease", Arch Intern Med 128:547–554.

Eisenstein et al., 1995, "Immunotherapy of a plasmacytoma with attenuated salmonella", Medical Oncol. 12(2):103–108.

Tsujitani, S. et al., 1998 Cancer 61: 1749–1753 Endoscopic Intratumoral Injection of OK–432 and Langerhans' Cells in Patients with Gastric Carcinoma.

Okamoto M. et al., 2002 Anticancer Res. 22: 3229–40 Enhancement of Anti–tumor Immunity by Lipteichoic Acid–related Molecule Isolated from OK–432, a Streptococcal Agent, in Athymic Nude Mice Bearing Human Salivary Adenocarcinoma: Role of Natural Killer Cells.

Hohmann et al., 1995, PNAS 92(7): 2904–08 Macrophage–inducible expression of a model antigen in *Salmonella typhimurium* enhances immunogenicity.

Okuno et al. Immunomodulating effect of intratumoral (IT) injection of biological response modifiers (BRM) on tumor–bearing hosts. J. Jpn. Soc. Cancer Ther. vol. 25(8):1543–1549, 1990.*

Translation of Japanese Office Action mailed Feb. 15, 2002 in connection with Japanese counterpart of U.S. application No. 08/658,034, now U.S. Pat. No. 6,190,657, to which the present application claims priority.

* cited by examiner

CONTROL

VECTOR (10 DAYS)

CONTROL+ GCV

TK VECTOR + GCV

VECTORS FOR THE DIAGNOSIS AND TREATMENT OF SOLID TUMORS INCLUDING MELANOMA

This application is a continuation application of U.S. patent application Ser. No. 08/658,034 filed Jun. 4, 1996, which issued on Feb. 20, 2001 as U.S. Pat. No. 6,190,657, and which in turn is a continuation-in-part application of U.S. patent application Ser. No. 08/486,422 filed Jun. 7, 1995, now abandoned, which is incorporated by reference herein in its entirety.

1. FIELD OF THE INVENTION

The present invention is concerned with the isolation and use of super-infective, tumor-specific, attenuated strains of parasites including, but not limited to, bacteria, fungi and protists. In certain embodiments the parasites include the bacterium Salmonella spp., such as *Salmonella typhimurium*, the bacterium *Mycobacterium avium*, and the protozoan *Leishmania amazonensis*, for the diagnosis and treatment of sarcomas, carcinomas, and other solid tumor cancers. In other embodiments, the present invention is concerned with the isolation and use of super-infective, tumor-specific, suicide gene-containing strains of parasites.

2. BACKGROUND OF THE INVENTION

Citation or identification of any reference in Section 2 of this application shall not be construed as an admission that such reference is available as prior art to the present invention.

A major problem in the chemotherapy of solid tumor cancers is the delivery of therapeutic agents, such as drugs, in sufficient concentrations to eradicate tumor cells while at the same time minimizing damage to normal cells. Thus, studies in many laboratories are directed toward the design of biological delivery systems, such as antibodies, cytokines, and viruses for targeted delivery of drugs, pro-drug converting enzymes, and/or genes into tumor cells. Houghton and Colt, 1993, New Perspectives in Cancer Diagnosis and Management 1: 65–70; de Palazzo,et al., 1992a, Cell. Immunol. 142:338–347; de Palazzo et al., 1992b, Cancer Res. 52: 5713–5719; Weiner, et al., 1993a, J. Immunotherapy 13:110–116; Weiner et al., 1993b, J. Immunol. 151:2877–2886; Adams et al., 1993, Cancer Res. 53:4026–4034; Fanger et al., 1990, FASEB J. 4:2846–2849; Fanger et al., 1991, Immunol. Today 12:51–54; Segal, et al., 1991, Ann N.Y. Acad. Sci. 636:288–294; Segal et al., 1992, Immunobiology 185:390–402; Wunderlich et al., 1992; Intl. J. Clin. Lab. Res. 22:17–20; George et al., 1994, J. Immunol. 152:1802–1811; Huston et al., 1993, Intl. Rev. Immunol. 10:195–217; Stafford et al., 1993, Cancer Res. 53:4026–4034; Haber et al., 1992, Ann. N.Y. Acad. Sci. 667:365–381; Haber, 1992, Ann. N.Y. Acad. Sci. 667: 365–381; Feloner and Rhodes, 1991, Nature 349:351–352; Sarver and Rossi, 1993, AIDS Research & Human Retroviruses 9:483–487; Levine and Friedmann, 1993, Am. J. Dis. Child 147:1167–1176; Friedmann, 1993, Mol. Genetic Med. 3:1–32; Gilboa and Smith, 1994, Trends in Genetics 10:139–144; Saito et al., 1994, Cancer Res. 54:3516–3520; Li et al., 1994, Blood 83:3403–3408; Vieweg et al., 1994, Cancer Res. 54:1760–1765; Lin et al., 1994, Science 265:666–669; Lu et al., 1994, Human Gene Therapy 5:203–208; Gansbacher et al., 1992, Blood 80:2817–2825; Gastl et al., 1992, Cancer Res. 52:6229–6236.

Because of their biospecificity, such systems could in theory deliver therapeutic agents to tumors. However, it has become apparent that numerous barriers exist in the delivery of therapeutic agents to solid tumors that may compromise the effectiveness of antibodies, cytokines, and viruses as delivery systems. Jain, 1994, Scientific American 7:58–65 (Jain). For example, in order for chemotherapeutic agents to eradicate metastatic tumor cells, they must a) travel to the tumors via the vasculature;

b) extravasate from the small blood vessels supplying the tumor;

c) traverse through the tumor matrix to reach those tumor cells distal to the blood supply; and d) interact effectively with the target tumor cells (adherence, invasion, pro-drug activation, etc).

Although antibodies and viruses can express specific recognition sites for tumor cells, they are dependent solely upon the forces of diffusion and convection in order to reach these sites. According to Jain:

An agent that destroys cancers cells in a culture dish should, in theory, be able to kill such cells in the body. . . . Sadly, however, the existing pharmacopoeia has not markedly reduced the number of deaths caused by the most common solid tumors in adults, among them cancers of the lung, breast, colon, rectum, prostate, and brain. . . . Before a blood-borne drug can begin to attack malignant cells in a tumor, it must accomplish three critical tasks. It has to make its way into a microscopic blood vessel lying near malignant cells in the tumor, exit from the vessel into the surrounding matrix (the interstitium), and finally, migrate through the matrix to the cells. Unfortunately, tumors often develop in ways that hinder each of these steps.

Jain points out that blood vessels supplying tumors are irregular and convoluted in shape so that blood flow is frequently restricted compared to that in normally vascularized tissue. In addition, there is an unusually high interstitial pressure in many tumors that counteracts the blood flow. Jain further points out that the two chief forces governing the transport of agents to tumor cells via the circulatory system are convection (the transport of molecules by a stream of flowing fluid), and diffusion (the movement of molecules from an area of high concentration to an area of low concentration). Since tumors are often non-uniformly vascularized, many cells in the tumors receive nutrients through the process of diffusion through the matrix. Jain and coworkers obtained data suggesting that "a continuously supplied monoclonal antibody having a molecular weight of 150,000 daltons could take several months to reach a uniform concentration in a tumor that measured one centimeter in radius and had no blood supply in its center."

2.1. Bacterial Infections and Cancer

Regarding bacteria and cancer, an historical review reveals a number of clinical observations in which cancers were reported to regress in patients with bacterial infections. Nauts et al., 1953, Acta Medica. Scandinavica 145:1–102, (Suppl. 276) state:

The treatment of cancer by injections of bacterial products is based on the fact that for over two hundred years neoplasms have been observed to regress following acute infections, principally streptococcal. If these cases were not too far advanced and the infections were of sufficient severity or duration, the tumors completely disappeared and the patients remained free from recurrence.

Shear, 1950, J. A.M.A. 142:383–390 (Shear), observed that 75% of the spontaneous remissions in untreated leukemia in the Children's Hospital in Boston occurred following an acute episode of bacterial infection. Shear stated:

> Are pathogenic and non-pathogenic organisms one of Nature's controls of microscopic foci of malignant disease, and in making progress in the control of infectious diseases, are we removing one of Nature's controls of cancer?

Subsequent evidence from a number of research laboratories indicated that at least some of the anti-cancer effects are mediated through stimulation of the host immune system, resulting in enhanced immuno-rejection of the cancer cells. For example, release of the lipopolysaccharide (LPS) endotoxin by Gram negative bacteria such as Salmonella triggers release of tumor necrosis factor, TNF, by cells of the host immune system, such as macrophages, Christ et al., 1995, Science 268:80–83. Elevated TNF levels in turn initiate a cascade of cytokine-mediated reactions which culminate in the death of tumor cells. In this regard, Carswell et al., 1975, Proc. Natl. Acad. Sci. USA 72:3666–3669, demonstrated that mice injected with bacillus Calmette-Guerin (BCG) have increased serum levels of TNF and that TNF-positive serum caused necrosis of the sarcoma Meth A and other transplanted tumors in mice. Further, Klimpel et al., 1990, J. Immunol. 145:711–717, showed that fibroblasts infected in vitro with Shigella or Salmonella had increased susceptibility to TNF.

As a result of such observations as described above, immunization of cancer patients with BCG injections is currently utilized in some cancer therapy protocols. See Sosnowski, 1994, Compr. Ther. 20:695–701; Barth and Morton, 1995, Cancer 75 (Suppl. 2) :726–734; Friberg, 1993, Med. Oncol. Tumor. Pharmacother. 10:31–36 for reviews of BCG therapy.

2.2. Parasites and Cancer Cells

Although the natural biospecificity and evolutionary adaptability of parasites has been recognized for some time and the use of their specialized systems as models for new therapeutic procedures has been suggested, there are few reports of, or proposals for, the actual use of parasites as vectors.

In this regard, Pidherney et al., 1993, Cancer Letters 72:91–98 (Pidherney et al.) and Alizadeh et al., 1994, Infect. Immun. 62:1298–1303 (Alizadeh et al.) have provided evidence that the pathogenic free-living amoeba, *Acanthamoeba castellani*, has tumorcidal capabilities toward human tumor cells, including melanoma, when added to tumor cells growing in culture or when injected directly into tumors in nude mice. Pidherney et al. conclude:

> The feasibility of utilizing the tumorcidal properties of pathogenic/free-living amoebae and their cell-free products in the treatment of drug-resistant or radio-resistant tumors warrants further investigation.

However, Pidherney et al. also point out that such pathogenic/free living amoebae can exist either as free-living organisms feeding on bacteria or as opportunistic pathogens producing life-threatening meningoencephalitis or blinding keratitis.

Thus, it is readily apparent that for any parasite to be effective as a therapeutic vector, for example, for human tumors, the benefit of the parasite as a vector must outweigh its risk as a pathogen to the patient. Therefore, although Pidherney et al. and Alizadeh et al. demonstrated cytotoxicity of pathogenic amoebae toward tumor cells, and further suggested their use in the treatment of drug-resistant and radio-resistant tumors, they offered no solution for the inherent pathogenicity of these organisms once injected into cancer patients. Furthermore, they offered no method, e.g., genetic selection for isolating super-infective, tumor-specific strains of pathogenic amoebae nor did they suggest insertion into the amoebael genome of genetic constructs containing inducible genes for the synthesis and secretion of pro-drug converting enzymes and/or suicide gene products.

Likewise, Lee et al., 1992, Proc. Natl. Acad. Sci. USA 89:1847–1851 (Lee et al.) and Jones et al., 1992, Infect. Immun. 60:2475–2480 (Jones et al.) isolated mutants of *Salmonella typhimurium* that were able to invade HEp-2 (human epidermoid carcinoma) cells in vitro in significantly greater numbers than the wild type strain. The "hyperinvasive" mutants were isolated under conditions of aerobic growth of the bacteria that normally repress the ability of wild type strains to invade HEp-2 animal cells. However, Lee et al. and Jones et al. did not suggest the use of such mutants as therapeutic vectors, nor did they suggest the isolation of tumor-specific bacteria by selecting for mutants that show infection preference for melanoma or other cancers over normal cells of the body. Without tumor-specificity or other forms of attenuation, such hyperinvasive *Salmonella typhimurium* as described by Lee et al. and Jones et al. would likely be pan-invasive, causing wide-spread infection in the cancer patient. Further, without selection for tumor specificity or employment of other forms of attenuation, use of such bacteria as therapeutic vectors would increase the risk of pan-infection and septic shock to the cancer patient.

Pan et al., 1995, Nature Medicine 1:471–477 (Pan et al.) described the use of *Listeria monocytogenes* as a vaccine for the immunization of mice against lethal challenges with tumor cells expressing the same antigen expressed by the Listeria vaccine. In addition, they showed regression of established tumors when immunized after tumor development in an antigen specific T-cell-dependent manner. However, Pan et al. did not show that *Listeria monocytogenes* could be used as a tumor specific vector, which would target and amplify within the tumor. Rather, Pan et al. showed that recombinant *Listeria monocytogenes* has the ability to deliver a foreign antigen to the immune system and to involve cell-mediated immunity against the same antigen.

Sizemore et al., 1995, Science 270:299–302 (Sizemore et al.) described the use of attenuated Shigella bacteria as a DNA delivery vehicle for DNA-mediated immunization. Sizemore et al. showed that an attenuated strain of Shigella invaded mammalian cells in culture and delivered DNA plasmids containing foreign genes to the cytoplasm of the cells. Foreign protein was produced in the mammalian cells as a result of the procedure. The Shigella vector was designed to deliver DNA to colonic mucosa, providing a potential oral and mucosal DNA immunization procedure as well as other gene immunotherapy strategies. However, Sizemore et al. did not suggest the use of such attenuated Shigella as tumor vectors in that they could be used to target tumors and thereby express genes within them. Rather, Sizemore et al. envisioned its use in vaccination therapy following oral delivery and invasion of the mucosa.

Clostridium was previously investigated as a potential therapeutic vector for solid tumors. The propensity of spores of the obligate anaerobe Clostridium to germinate in necrotic tissues is well known. Tetanus and gas gangrene result from successful colonization of necrotic tissue by pathogenic members of this genus.

Parker et al., 1947, Proc. Soc. Exp. Biol. Med. pp. 461–467 first showed that direct injection of spores of *Clostridium histolyticus* into a transplantable sarcoma growing in a mouse caused oncolysis, i.e., liquification, as well as regression of the tumor. In general the process of Clostridium-mediated oncolysis was accompanied by acute toxicity and death of the mice. Malmgren and Flanigan, 1955, Cancer Res. 15:473 demonstrated that mice bearing mammary carcinomas, hepatomas, and other tumors died within 48 hrs of intravenous injection of *Clostridium tetani* spores, whereas control, non-tumor bearing animals were asymptomatic for 40 days. Möse and Möse, 1964, Cancer Res. 24:212–216 (Möse and Möse) described the colonization and oncolysis of tumors by *Clostridium butyricum*, strain M-55, a non-pathogenic soil isolate. Möse and Möse established the lack of human pathogenicity of the M-55 strain by administering spores to themselves, as reported by Carey et al., 1967, Eur. J. Cancer 3:37–46. Using *Clostridium butyricum* strain M-55, Möse and Möse reported that intravenous injections of spores caused oncolysis of the mouse Erlich ascites tumor, growing experimentally as a solid tumor. Aerobic spore-forming organisms—e.g., *Bacillus mesentericus, Bacillus subtilis*, which were prepared in a similar manner, did not show any oncolysis under the same conditions. Möse and Möse concluded that the clostridial oncolysis was restricted to anaerobic areas of the tumors because of the anaerobic metabolic requirements of the bacteria.

Gericke and Engelbart, 1964, Cancer Res. 24:217–221 showed that intravenously injected spores of strain M-55 produced extensive lysis of a number of different tumors, but with shortened survival times of the Clostridium-treated, tumor-bearing animals compared to non-treated tumor-bearing animals. Further, they found that "metastases in organs or lymph nodes were unaffected by the spores unless the metastatic tumors had reached a considerable size."

Thiele et al., 1964, Cancer Res. 24:222–233 showed that intravenously injected spores of a number of species of nonpathogenic Clostridia, including M-55, localized and germinated in tumor tissue, but not in normal tissues of the mouse. Thiel et al., 1964, Cancer Res. 24:234–238 found that spore treatment produced no effect when administered early in the development of the tumor, i.e., when the tumors were of small size. While the spores caused oncolysis in tumors of sufficient size, there was no effect in smaller tumors or metastases. The animals regularly died during oncolysis. Carey et al., 1967, Eur. J. Cancer 3:37–46, concluded that small tumors and metastases had been noted to be resistant to oncolysis whereas large neoplasms were particularly favorable. Thus, the qualitative differences in germination of spores were likely to be not a characteristic of neoplastic and normal tissues per se, but related to physiologic and biochemical conditions found within large tumor masses.

Recent molecular genetic studies have focused on anaerobic bacteria of the genus Clostridium as potential tumor vectors. Fox et al., 1996, Gene Therapy 3:173–178 using a Clostridium expression vector were able to transform the *E. coli* cytosine deaminase gene into *Clostridium beijerincki*, which resulted in increased cytosine deaminase activity in the growth medium supernatant and cell extracts of transformed clostridial bacteria. Such supernatants, when added to cultures of mouse EMT6 carcinoma made the cells sensitive to 5-fluorocytosine, presumably through its conversion to the toxic 5-fluorouracil. Similarly, Minton et al., 1996, FEMS Microbiol. Rev. 17:357–364 inserted the *E. coli* nitroreductase gene into *Clostridium beijerincki* and were able to detect expression of the gene in an in vivo murine tumor model through the use of antibodies directed against the *E. coli* nitroreductase gene. The nitroreductase gene product activates CB1954, a potent alkylating agent.

Nothing in any of the above references (or any other references known to the present inventors) suggests the use of any microorganisms, other than the obligate anaerobe Clostridium, as a potential therapeutic vector for solid tumors.

2.3. Attenuated Salmonella Spp.

Bacon et al., 1950, Br. J. Exp. Path. 31:703–713; Br. J. Exp. Path. 31:714–724; 1951, Br. J. Exp. Path. 32:85–96 demonstrated that attenuation of Salmonella for virulence in mice can be achieved through auxotrophic mutations, i.e., through the use of mutants which lack the ability to synthesize precursor molecules necessary for growth. More specifically, the authors showed that purine-requiring ($Pur^-$) auxotrophs of Salmonella were attenuated in mice.

Hoiseth and Stocker, 1981, Nature 291: 238–239 showed that *Salmonella typhimurium* auxotrophic mutants with requirements for aromatic amino acids ($Aro^-$) were attenuated for virulence in C57BL mice. Further, Su et al., 1992, Microbiol. Pathogenesis 13:465–476 showed that one such $Aro^-$ mutant, the attenuated antigen carrier strain of *Salmonella typhimurium*, SL3261, was useful as a vaccine. The Shiga toxin B-subunit/hemolysin A (C-terminus) fusion protein was expressed and underwent extracellular export resulting in antigen-specific immune responses in mice inoculated with these bacteria.

O'Callaghan et al., 1988, Infect. Immun. 56:419–423 characterized *Salmonella typhimurium* that were both Aro- and Pur- and found that although they were highly attenuated in BALB/c mice, they persisted for several weeks in the livers and spleens following i.v. injections. They were found to be ineffective as vaccines when administered either orally or i.v.

Johnson et al., 1991, Mol. Microbiol. 5:401–407 (Johnson et al.) demonstrated that attenuation in Salmonella virulence can be achieved through mutations in the heat shock inducible protein HtrA, a serine protease. Chabalgoity et al., 1996, Mol. Microbiol. 19:791–801, demonstrated that such attenuated htrA- *Salmonella typhimurium* were useful as live vaccines.

However, none of the references by Bacon et al., Hoiseth and Stocker, O'Callaghan et al., Johnson et al., Su et al. 1992, Chabalgoity et al. 1996, nor any of the studies referred to in Table 4, infra, suggest that such avirulent strains of *Salmonella typhimurium* would survive and proliferate within solid tumors, nor that such avirulent mutants might be used as vectors for solid tumor therapy.

2.4. Objectives of the Invention

The problems associated with the many physical barriers for delivery of therapeutic agents to solid tumors provide clear and difficult obstacles in the design of effective delivery systems. Thus, there has been a long felt need in the art to provide delivery systems which are able to overcome these obstacles.

It is an object of the present invention to use and to provide more advanced biological vectors such as parasites having several distinct advantages as a novel delivery system, some of which are listed below, as well as to meet the challenges of tumor therapy.

Antibiotic Sensitivity: It is an advantage for a tumor-specific parasitic vector to be sensitive to exogenously administered antibiotics. Parasites, such as bacteria, can be eradicated within their hosts by the administration of antibiotics. Such antibiotic sensitivity allows for the eradication of the parasite from the cancer patient's body upon completion of the therapeutic protocol.

Biospecificity: It is an advantage for a vector to express specificity for its target cell, e.g., a tumor cell. The more specificity, of the vector for the tumor cell, the lower the inoculum necessary for effective therapy, thereby reducing the risk of septic shock or pan-infection to the cancer patient. Parasites show a great degree of natural biospecificity, having evolved to utilize a variety of specific recognition and invasion mechanisms. (For general discussions on biospecificity see: Falkow, 1991, Cell 65:1099–1102; Tumomanen, 1993, Am. Soc. Microbiol. 59:292–296).

Mutant Isolation and Genetic Manipulation: It is an advantage, in the design and isolation of a parasite as a tumor-specific, therapeutic vector, for the parasite to be amenable to genetic manipulation. Parasites with haploid genomes and short generation times, for example, bacteria such as *Salmonella typhimurium* and enteroinvasive *Escherichia coli*, can be readily subjected to mutagenesis followed by enrichment procedures for the isolation of strains with desired new characteristics (see generally, Neidhardt et al., (ed.) 1987, *Escherichia coli* and *Salmonella typhimurium*, Cellular and Molecular Biology. American Society for Microbiology, pp 990–1033. Furthermore, the methods for the genetic analysis and stable introduction of genetic constructs into these bacteria are well known to the science of molecular genetics.

Chemotaxis: A chemotactic response toward cancer cells is an advantage for a tumor-specific vector, for example as a stimulus for the vector to invade through a basement membrane matrix such as that produced by endothelial cells in the vasculature, or as a stimulus for the vector to seek out cancer cells surrounded by tumor matrix. Chemotactic responses in parasites and commensalists or mutualists, particularly in bacteria such as *Escherichia coli* and *Salmonella typhimurium*, are well documented. For a review of chemotaxis see Macnab, 1992, Ann. Rev. Genet. 26:131–158.

Replication Within Target Cells: The ability to replicate within target cells is an advantage for a tumor-specific vector. Such an ability allows for amplification of the therapeutic vector number within the infected cancer cell, thus increasing the therapeutic effectiveness of the vector. Progeny of vectors within cancer cells further infect surrounding or distant cancer cells, thus amplifying the vector number within the tumor cell population.

Anaerobic and Aerobic Metabolism: The ability to express invasive and amplification capacities under either aerobic or anaerobic conditions is an advantage for a tumor-specific vector. Solid tumors generally contain vascularized, oxygen-rich areas as well as necrotic oxygen-poor areas. A vector that is functional in both such environments would be able to reach a larger portion of tumor cells than one that can function in only one environment, such as, for example, an obligate anaerobe or aerobe.

3. SUMMARY OF THE INVENTION

The present invention provides compositions and methods for delivery of genes and/or gene products to and/or into target mammalian cells in vitro or in vivo. The genes and/or gene products are delivered by microorganism vectors, including bacteria, fungal and protozoan parasites, which are selected and/or genetically engineered to be specific to a particular type of target mammalian cell. In a preferred embodiment, the vectors function under both aerobic and anaerobic conditions, are super-infective, tumor-specific microorganisms useful for diagnosis or treatment of sarcomas, carcinomas, lymphomas or other solid tumor cancers, such as germ line tumors and tumors of the central nervous system, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, and melanoma.

Vectors useful for the methods of the present invention include but are not limited to *Borrelia burgdorferi, Brucella melitensis, Escherichia coli*, enteroinvasive *Escherichia coli, Legionella pneumophila, Salmonella typhi, Salmonella typhimurium*, Shigella spp., Streptococcus spp., *Treponema pallidum, Yersinia enterocohtica, Chlamydia trachomatis, Listeria monocytogenies, Mycobacterium avium, Mycobacterium bovis, Mycobacterium tuberculosis*, BCG, *Mycoplasma hominis, Rickettsiae quintana, Cryptococcus neoformans, Histoplasma capsulatum, Pneumocystis carnii, Eimeria acervulina, Neospora caninum, Plasmodium falciparum, Sarcocystis suihominis, Toxoplasma gondii, Leishmania amazonensis, Leishmania major, Leishmania mexacana, Leptomonas karyophilus*, Phytomonas spp., *Trypanasoma cruzi, Encephahtozoon cuniculi, Nosema helminthorum, Unikaryon legeri*.

As used herein, *Salmonella typhimurium* encompasses all Salmonella species. It has long been recognized that the various "species" of the genus Salmonella are in fact a single species by all acceptable criteria of bacterial taxonomy. The single species is now designated "*Salmonella enterica*". F. Neidhardt (ed.), *Escherichia coli* and Salmonella, 1996, Volume I, pp. xx, ASM Press, Wash. D.C.

An embodiment of the present invention is to provide methods for the isolation of super-infective, attenuated, tumor-specific mutants of microorganisms such as bacterial, fungal and protozoan parasites. Further, the present invention provides methods for use of these microorganisms in the diagnosis and treatment of malignant and/or metastatic solid tumor cancers, such as melanoma or colon cancer. Moreover, these mutant parasites may express specific gene products, some of which are secreted into the cytoplasm or vacuolar space of the infected cell.

The present invention provides methods for the isolation of super-infective target cell-specific microorganisms. In particular embodiments, the invention provides for the isolation and use of super-infective, tumor-specific strains of parasites such as the bacterium Salmonella spp., including *S. typhimurium*, the bacterium *Mycobacterium avium*, and the protozoan *Leishmania amazonensis*. The tumor-specific vectors can also contain suicide genes.

One embodiment of the present invention provides methods for the isolation of and compositions comprising super-infective, tumor-specific mutants of Salmonella spp., e.g., *Salmonella typhimurium*, and for their use in the diagnosis and treatment of sarcomas, carcinomas, melanomas, colon cancer, and other solid tumor cancers. Another embodiment of the present invention provides methods for the isolation of and compositions comprising super-infective, tumor-specific mutants of Salmonella spp. containing a suicide gene. In a specific embodiment, the suicide gene is thymidine kinase from *Herpes simplex* virus or cytosine deaminase from *Escherichia coli* or human microsomal p450 oxidoreductase.

Another embodiment of the present invention provides methods for the isolation of and compositions comprising super-infective, tumor-specific mutants of the protozoan, *Leishmania amazonensis* and for their use in the diagnosis and treatment of sarcomas, carcinomas, melanomas, colon cancer, and other solid tumor cancers.

Yet another embodiment of the present invention provides methods for the isolation of and compositions comprising super-infective, tumor-specific mutants of the bacterium *Mycobacterium avium* and for their use in the diagnosis and treatment of sarcomas, carcinomas, melanomas, colon cancer, and other solid tumor cancers.

Yet another embodiment of the present invention provides methods for attenuation of parasite vector toxicity so as to reduce the risk of septic shock or other complications in the host, i.e., the patient receiving vector-delivered gene therapy. Such methods include mutagenesis of parasites; isolation of parasite mutants with increased tumor specificity, increased specificity for suicide gene expression and concomitant reduced ability to infect normal host cells in the body; isolation of mutants with enhanced chemotactic abilities toward cancer cell secretory products; isolation of mutants with genetically altered lipopolysaccharide composition; and isolation of mutants with altered virulence genes so as to achieve specific survival of the parasitic vector in cancer cells as opposed to normal cells of the host body.

The present invention further encompasses use of microorganism vectors for diagnosis or treatment of solid tumor cancers.

The present invention may be understood more fully by reference to the following definitions, detailed description of the invention, illustrative examples of specific embodiments and the appended figures in which:

4. DEFINITIONS

Attenuation: Attenuation, in addition to its traditional definition in which a microorganism or vector is modified so that the microorganism or vector is less pathogenic, is intended to include also the modification of a microorganism or vector so that a lower titer of that microorganism or vector can be administered to a patient and still achieve comparable results as if one had administered a higher titer of the parental microorganism or vector. The end result of attenuation is that the risk of toxicity as well as other side-effects is decreased, when the microorganism or vector is administered to the patient.

Suicide gene: A suicide gene is defined as a gene that when delivered to a target cell and expressed by a vector of the present invention causes the death of the target cell and/or the vector.

Super-infective: A super-infective vector is defined as a vector which is able to attach and/or infect a target cell more readily as compared to the wild type vector. Depending on the population density of the inoculum, the ratio between super-infective vectors and wild type vectors detectably infecting a target cell approaches 4:1, preferably 30:1, more preferably 90:1. Most preferably, one is able to reduce the inoculum size and infection time so that only the super-infective vectors have time to attach to and/or infect cancer cells growing in cell culture in vitro or as tumors in vivo.

Tumor-specific: A tumor-specific vector is defined as a vector which is able to distinguish between a cancerous target cell and the non-cancerous counterpart cell so that the vector preferentially attaches to, infects and/or remains viable in the cancerous target cell.

BRIEF DESCRIPTION OF THE DRAWINGS

FIG. 1 depicts a DNA cassette system for expressing pro-drug converting enzymes. Each of the components is generated by PCR using primers dontaining specific restriction endonuclease sites NotI, NsiI, NcoI, SfiI or PacI that allow for simple interchange of individual components. For example, (A) is the coding sequence for pro-drug converting enzymes such as thymidine kinase, cytosine deaminase or human microsomal p450 oxidoreductase; (B) is a promoter, which is active in an inducible, constitutive or cell specific manner; (C) is a N-terminal secretion signal sequence, such as the β-lactamase signal sequence; and (D) is a C-terminal secretion signal sequence, such as the enteroinvasive *E. coli* hemolysin A signal sequence.

FIGS. 2A–B are photomicrographs of *Salmonella typhimurium* wild type strain ATCC No. 14028 infecting human melanoma cell line M2. A starting population of ATCC No. 14028 was subjected to 10 cycles of infection into and recovery from M2 melanoma cells before use in the infection assay shown in FIGS. 2A–B. FIG. 2A. Light micrograph of an infected melanoma cell. FIG. 2B. DAPI staining of the cell showing cell nucleus, (n), and numerous bacteria inside the cell, (arrow).

FIGS. 3A–C are photomicrographs of *Salmonella typhimurium* wild type strain ATCC No. 14028 during the process of internalization into human melanoma cell line M2. FIG. 3A. Phase contrast micrograph of a host cell. FIG. 3B. DAPI staining of the host cell showing the position of the bacteria, (arrow), and the host cell nucleus, (n). FIG. 3C. Lysosomal glycoprotein LAMP-1 antibody staining of the host cell showing co-localization of the bacteria with lysosomes and/or melanosomes.

FIGS. 4A–B. Expression of the *Herpes simplex* thymidine kinase gene containing a β-lactamase secretory signal sequence in *Salmonella typhimurium* super-infective clone 72. FIG. 4A. Immunoblot analysis of *Salmonella typhimurium* strains using an anti-TK monoclonal antibody. Lane 1: bacteria containing only the plasmid vector p279; Lane 2: strain 14028 wt (CDC6516-60) (MO) containing the cytoplasmicly expressed form of TK (pHETK2); Lane 3: strain 14028 clone 72 containing the cytoplasmicly expressed form of TK (pHETK2); Lane 4: strain 14028 wt (MO) containing the β-lactamase fusion form of TK (p5-3); Lane 5: strain 14028 clone 72 containing the β-lactamase fusion form of TK (p5-3); Lane 6: strain 14028 wt (MO) containing the β-lactamase fusion form of TK (p2lA-2); Lane 7: strain 14028 clone 72 containing the β-lactamase fusion form of TK (p21A-2). Relative molecular mass×$10^3$ is shown on the left. No antibody reactivity is seen in the "vector only" control (Lane 1). In each lane where the cytoplasmically expressed TK is present (Lanes 2 and 3) two major isoforms of the protein are seen; a higher molecular mass isoform containing a leader sequence and a lower molecular mass isoform wherein the leader sequence has been proteolytically cleaved off. In each lane where the bacteria express the TK gene β-lactamase signal sequence fusion (Lanes 4 to 7) two major isoforms of the protein are also seen: a higher molecular mass form containing the signal sequence and a lower molecular mass isoform wherein the signal sequence has been proteolytically cleaved off, which is the same apparent molecular mass as the processed form of the cytoplasmic enzyme.

FIG. 4B. Relative TK enzyme activity associated with each of the samples in Figure A. Enzyme activity is expressed as the total number of counts of $^{125}$IdC phosphorylated in a standard assay, Summers and Summers, 1977, J. Virol. 24:314–318. A small background is present in a bacterial extract from the vector only sample (Lane 1). Significantly higher levels of TK activity are observed in the wild type and the super-infective clone 72 containing the cytoplasmic form of TK pHETK2, Lanes 2 and 3. Similar levels are observed in both the wild type and super-infective clone 72 containing the β-lactamase signal sequence fusion isoform of TK p5-3, Lanes 4 and 5. Lower levels are observed in both the wild type and super-infective clone 72 containing the β-lactamase signal sequence fusion isoform of TK p21A-2, Lanes 6 and 7.

FIG. 4-C is a schematic of the different *Herpes Simplex* Virus thymidine kinase secretion and expression constructs.

FIG. 4-D is a schematic of the different human microsomal cytochrome p450 oxidoreductase expression constructs.

FIG. 4-E is a schematic of the *E. coli* cytosine deaminase secretion and expression construct.

FIG. 4-F is a graph showing the amount of 5-FC converted to 5-FU by different bacteria.

FIGS. 5A–B are photomicrographs of histologic sections from a Cloudman S91 melanoma/macrophage hybrid #48 growing subcutaneously in a DBA/2J mouse. The tumor was excised from a mouse that had been inoculated 2 days earlier with $3 \times 10^5$ c.f.u. *Salmonella typhimurium* super-infective clone #72 carrying the HSV TK gene, clone #72$^{5\text{-}3\text{-}2}$. FIG. 5A. A section stained with hematoxylin and eosin shows tumor cells with a central area of necrosis, denoted by arrows. FIG. 5B. A section stained with Brown-Brenn stain (tissue gram stain) shows gram negative bacteria in a necrotic area of the tumor, denoted by the arrow. When viewed under a light microscope, the bacteria stain pink/purple against a yellow background.

FIG. 6 is an electron micrograph of a section of a Cloudman S91 melanoma/macrophage hybrid #48 tumor excised from a DBA/2J mouse that had been inoculated i.p. 42 hours earlier with $4 \times 10^6$ *Salmonella typhimurium* super-infective clone 72. Visible in the micrograph are two *Salmonella typhimurium* bacteria, denoted by arrows, along with numerous melanosomes (m), sub-cellular organelles characteristic of melanoma cells. The co-localization of Salmonella and such melanosomes indicates that the bacteria are present in the cytoplasm of the melanoma cell. Magnification=21,000×.

FIG. 7 is a photomicrograph of a histologic section from a B16F1O melanoma growing subcutaneously in a C57BL/6J mouse. The tumor was excised from a mouse that had been inoculated 42 hours earlier with $1.8 \times 10^5$ c.f.u. *Salmonella typhimurium* super-infective clone #72 carrying the HSV TK gene. The sections were from the same tumor examined with the electron microscope as detailed in FIG. 8. The section was stained with Brown-Brenn stain (tissue gram stain) and shows gram negative bacteria in a necrotic area of the tumor, denoted by arrows. When viewed under a light microscope, the bacteria stain pink/purple against a yellow background.

FIG. 8 is an electron micrograph of a section from a B16F1O melanoma tumor excised from a C57BL/6J mouse that had been inoculated i.p. 42 hours earlier with $1.8 \times 10^5$ *Salmonella typhimurium* super-infective clone #72 carrying the HSV TK gene. The section was from the same tumor examined with the light microscope as detailed in FIG. 7. The micrograph shows numerous *Salmonella typhimurium* in extracellular spaces, denoted by arrows, and in an area of necrosis. A single bacterium is also seen within the cytoplasm of a dying melanoma cell. The cytoplasm of the dying melanoma cell also contains numerous black melanosomes (m), characteristic of the B16F1O melanoma. Magnification=9,750×.

FIGS. 9A–D depict growth of Cloudman S91 melanoma/macrophage hybrid #48 tumors in DBA/2J mice under various treatment conditions. Mice were inoculated s.c. in the flank region with $3 \times 10^5$ melanoma cells. The tumors were palpable 8–10 days later, and some of the mice were then further inoculated with *Salmonella typhimurium* super-infective clone #72 carrying the HSV TK gene. Twenty-four hours post inoculation with bacteria, some groups of the mice were further inoculated i.p. with 2.0 mg ganciclovir. Ganciclovir inoculations were repeated 6 times over a 5 day period. Points represent caliper measurements of tumors in 2 to 5 mice per treatment group at the days indicated. Measurements in mm were made of length, width, and height for each tumor and volumes were calculated in mm$^3$. Average tumor volumes for each group of mice were defined as 100% on day 0, the beginning day of treatment. (FIG. 9A). Control mice: no Salmonella; no ganciclovir (FIG. 9B). Ganciclovir only; (FIG. 9C). Salmonella only; (FIG. 9D). Salmonella+ganciclovir.

FIG. 10A shows a control mouse and FIG. 10B shows a *Salmonella typhimurium*-infected (7B) DBA/2J mouse. The mice were inoculated (s.c.) with Cloudman S91 melanoma/macrophage hybrid #48 tumor cells. Upon the appearance of palpable tumors some of the mice were inoculated (i.p.) with $3 \times 10^5$ c.f.u. *Salmonella typhimurium* clone 72 containing the HSV TK gene (clone #72$^{5\text{-}3\text{-}2}$), allowed to eat and drink ad libitum for 10 days, and then treated with Sulfatrim™ antibiotic in their drinking water for several more days and photographed. Tumors in the depicted mice were representative of the general state of tumor progression in mice in Salmonella-treated and untreated cages.

FIGS. 11A–B. FIGS. 11A–B depict a control (FIG. 11A) and a *Salmonella typhimurium*-infected (FIG. 11B) DBA/2J mouse. The mice were inoculated (s.c.) with Cloudman S91 melanoma/macrophage hybrid #48 tumor cells Upon the appearance of palpable tumors, some of the mice were inoculated with $3 \times 10^5$ c.f.u. *Salmonella typhimurium* clone #72 containing the HSV TK gene (clone #72$^{5\text{-}4\text{-}2}$). Control and Salmonella-infected mice were then injected (i.p.) with 2.0 mg ganciclovir a total of 5 times over a 4 day period. The mice were then treated with Sulfatrim™ antibiotic in their drinking water for several more days and photographed. The depicted mice are representative of the general state of tumor progression in mice, either in Salmonella-treated and untreated cages.

FIGS. 11(C–E) show the effect of ganciclovir on the growth of B16F10 melanomas in mice with and without inoculation of *Salmonella typhimurium* clone YS7211 (FIG. 11-1A); clone YS7213 (FIG. 11-1B); and clone YS7212 (FIG. 11-1C).

FIG. 11-F is a graph showing the growth of B16F10 melanoma cells in monolayer culture in the presence or absence of ganciclovir at 10 μg/ml or 25 μg/ml.

FIG. 11-G is a graph showing the effect of ganciclovir on the growth of B16F10 melanomas in mice following inoculation of *Salmonella typhimurium* clone YS7211 carrying the HSV thymidine kinase gene, YS7211/p5-3, with and without ganciclovir.

FIG. 11-H is a graph showing the effect of total amounts of ganciclovir on the growth of B16F10 melanomas in mice following inoculation with *Salmonella typhimurium* clone YS7211 carrying the HSV thymidine kinase gene, YS7211/p5-3.

FIG. 12A is an electron micrograph of a section from a HCT 116 human colon tumor excised from a BALB/c nu/nu mouse. The mouse had been inoculated i.p. 72 hours earlier with $2.8 \times 10^5$ c.f u. *Salmonella typhimurium* super-infective clone #72 containing the HSV TK gene, clone #72$^{5-3-2}$. Shown in the micrograph are numerous *Salmonella typhimurium* within the cytoplasm of a neutrophil associated with the tumor. Some of the bacteria are undergoing division as denoted by arrows. The neutrophil or polymorphonucleoleukocyte is characterized by its multi-lobed nucleus (n), (Magnification=21,000×).

FIG. 12-B is an electron micrograph showing numerous *Salmonella typhimurium*, denoted by arrows, in extracellular spaces as well as contained within a single cell, possibly a neutrophil, seen in the upper left. Also seen in the field are two unidentified cells that appear to be dying as indicated by the large intracellular space, along with cellular debris.

FIGS. 13A–B depict *Leishmania amazonensis* adhesion to human melanoma cell line M2. FIG. 13A. Phase contrast micrograph showing parasites attached to cell, (arrow). FIG. 13B. DAPI staining showing the parasite DNA, (arrows), and the host cell nucleus, (n).

FIGS. 14A–C are photomicrographs of *Leishmania amazonensis* during the process of internalization into human melanoma cell line M2. FIG. 14A. Phase contrast of a Leishmania trypomastigote, (arrow), entering a host cell. FIG. 14B. DAPI staining showing the position of the parasite, (arrow), and the host cell nucleus, (n). FIG. 14C. Lysosomal glycoprotein LAMP-1 antibody staining of the host cell showing co-localization of the bacteria and the lysosomes.

FIGS. 15 A–C are graphs showing growth of *Salmonella typhimurium* clone 72 and clone YS7212 in minimal Medium 56 supplemented with glucose only; Medium 56 with glucose plus adenine, vitamin B1, isoleucine, valine, and uracil; or Medium 56 with tumor extract (10%) only.

FIG. 15-D is a graph depicting growth of *Salmonella typhimurium* clones 72 and YS7212 following invasion into human M2 melanoma cells in culture.

6. DETAILED DESCRIPTION OF THE INVENTION

Figure 1:
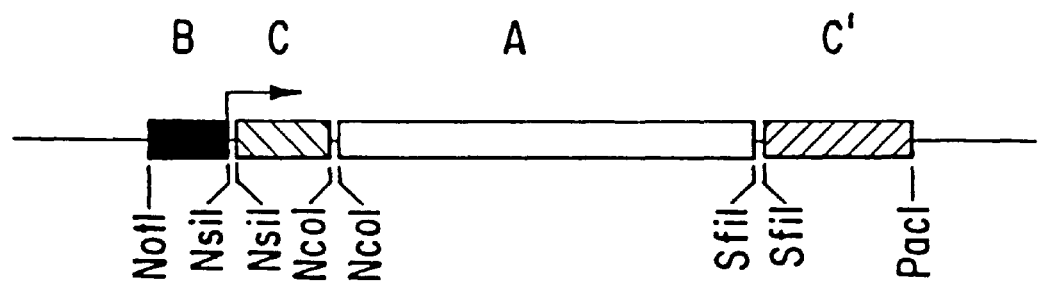
FIG. 1.

The present invention is directed to the isolation of novel therapeutic and diagnostic parasitic vectors for solid tumor cancers, such as sarcomas, carcinomas, lymphomas or other solid tumor cancers, for example, germ line tumors and tumors of the central nervous system, including, but not limited to, breast cancer, prostate cancer, cervical cancer, uterine cancer, lung cancer, ovarian cancer, testicular cancer, thyroid cancer, astrocytoma, glioma, pancreatic cancer, stomach cancer, liver cancer, colon cancer, melanoma and their use. Described, in detail below, are the novel intracellular parasite vectors; methods for the isolation of the novel vectors; genetic engineering of the isolated vectors; and methods for use of the novel vectors as well as other vectors in treatment or detection of solid malignant tumors, including metastatic tumors and tumor cells.

6.1. Novel Vectors and Methods For Their Isolation

The isolated vectors, which are for example, bacteria, fungi or protista, are able to differentiate between cancerous cells and non-cancerous counterpart cells. For example, the isolated vectors are able to differentiate melanoma cells from melanocytes or differentiate colon cancer cells from normal colon epithelial cells. Table I is a representative list, which is in no way meant to limit the present invention, of intracellular parasitic and pathogenic microorganisms which are useful as tumor-specific vectors for the present invention and/or for isolation of novel mutant strains which are super-infective and tumor-specific vectors for use in the present invention.

TABLE 1

REPRESENTATIVE LIST OF ORGANISMS USEFUL AS VECTORS

Gram negative bacteria

*Borrelia burgdorferi*
*Brucella melitensis*
*Escherichia coli*
enteroinvasive *Escherichia coli*
*Legionella pneumophila*
*Salmonella typhi*
*Salmonella typhimurium*
*Shigella* spp.
*Treponema pallidum*
*Yersinia enterocohtica*

Gram positive bacteria

BCG (*Bacillus Calmette-Guerin*)
*Chlamydia trachomatis*
*Listeria monocytogenies*
*Mycobacterium avium*
*Mycobacterium bovis*
*Mycobacterium tuberculosis*
*Mycoplasma hominis*
*Rickettsiae quintana*
*Streptococcus* spp.

Fungi

*Cryptococcus neoformans*
*Histoplasina capsulatum*
*Pneumocystis carnii*

Apicomplexans

*Eimeria acervulina*
*Neospora caninum*
*Plasmodium falciparum*
*Sarcocystis suihominis*
*Toxoplasma gondii*

Kinetoplastida

*Leishinania amazonensis*
*Leishmania major*

TABLE 1-continued

REPRESENTATIVE LIST OF ORGANISMS USEFUL AS VECTORS

*Leishmania mexacana*
*Leptomonas karyophilus*
Phytomonas spp.
*Trypanasoma cruzi*
Microsporidians

*Encephahtozoon cuniculi*
*Nosema helminthorum*
*Unikaryon legeri*

The bacterium *Salmonella typhimurium*, the bacterium *Mycobacterium avium*, and the protozoan *Leishmania amazonensis* are each particularly useful vectors for the present invention, since each of these organisms shows natural preference for attachment to and penetration into certain solid tumor cancer cells in tissue culture, as opposed to non-cancerous counterpart cells. Since these vectors, such as Salmonella, have a natural ability to distinguish between cancerous cells and their non-cancerous counterpart cells they are directly applicable to the methods for diagnosis or treatment according to the present invention. However, this tumor-specific ability, as well as, the ability to be super-infective as compared to the "wild type" parent strain may be enhanced and selected for by using the methods of the present invention described in Sections 6.1.1–6.1.4., infra.

6.1.1. Isolation By Cycling Through In Vitro Tissue Culture

One embodiment of the present invention is to isolate the novel vectors of the present invention by cycling a microorganism through a pre-selected target cell, preferably a solid tumor cancer cell, with one or more cycles of infection in in vitro tissue culture so that the cycled population and/or clonal isolates therefrom demonstrate enhanced infectivity of the target tumor cell as compared to the starting microbial population and enhanced selectivity as compared to the non-cancerous counterpart cell. The method entails selecting a parasite or pathogen and adding the microorganism to an in vitro tissue culture system of the particular type of solid tumor that one wishes to use as a target cell. For example, if one desires to target melanoma tumors, the target cell may be M2 human melanoma cells. After incubating the tumor cells and microorganisms together, which allows enough time for the microorganism to attach and/or infect the tumor cell, the tumor cell culture is washed with either buffer or medium which contains an antibiotic agent effective against the specific microorganism used. The antibiotic agent kills any microorganisms that have not attached to and infected the tumor cell. If desired, the infected tumor cell culture may be incubated further in medium containing antibiotic for varying times, depending on the type of population of microorganisms to be isolated. For example, for longer incubation times, the microorganism population isolated has enhanced survival and/or proliferative abilities inside the tumor cells as compared to the starting population of microorganisms. Additionally, the isolated populations can be cultured to isolate single colony clones using standard techniques.

The infected animal cells are collected and lysed, thus freeing the internalized microorganisms. The microorganism can then be isolated, for example, by centrifugation (2000×g for 4 minutes) and resuspending in fresh medium. The isolated microbial population may then be used for additional cycles of infection into and isolation out of the target tumor cell. The isolated microbial population may be placed first in appropriate growth medium for 1-2 doubling times before being subjected to additional infection cycles to insure their viability. The isolated microbial population may also be cultured so as to isolate and collect single colony clones. The isolated microorganisms may also undergo known in vitro techniques to determine their relative infective and selective abilities as compared to the "wild type" parent strain which did not undergo in vitro selection. For example, in side by side comparisons one may test the relative infectiveness of the isolated microorganism as compared to the "wild type" by using assays designed to quantitate the number of microorganisms which have attached to or invaded the target tumor cell and/or their ability to distinguish between cancerous and non-cancerous cells. In addition, parameters such as microorganism population density, may be varied in these in vitro assays which assists in determining what effect the overall concentration of inoculum of the clone or population being tested has on the ability of the microorganisms to differentiate between the target tumor cells and their non-cancerous counterparts.

For an illustrative example of super-infective, tumor-specific vectors isolated by cycling through in vitro tissue culture, see Section 7, infra.

6.1.2. Isolation By Cycling Through In Vivo Solid Tumors

Another embodiment of the present invention is to isolate the novel vectors of the present invention by cycling the microorganism through solid tumors in vivo. This procedure is performed using experimental tumor models in mammals such as, for example and not by way of limitation, B16 mouse melanoma cells which form melanoma tumors in C57B6 mice and HCT116 human colon carcinoma cell which form colon carcinomas in nu/nu and other immunocompromised mice. Additionally, fresh biopsies of tumor tissue which are obtained surgically from a cancer patient may be used to inoculate nu/nu, scid or other immunocompromised mice. These tumors in mice which have grown from inoculated cancer cells are used as in vivo targets for the isolation of super-infective and tumor-specific vectors in a similar manner as in vitro target cells. Any tumor growing in mice or any other animal may be used in the present invention as a target for the isolation of super-infective and tumor-specific vectors in vivo.

Once the tumor is established in the mouse, by, for example, inoculation of cancer cells sub-cutaneously or transplantation of a tumor mass, the selected microorganism is inoculated into the mouse. After a pre-determined infection time after inoculation in which the microorganism becomes co-localized with the tumor and/or infects the tumor cells, the mice are sacrificed, the tumors excised, weighed and homogenized. An aliquot may be diluted into the proper microorganism growth medium and incubated at the proper growth conditions for 1-2 population doublings to insure the recovery of viable microorganisms for successive inoculations into tumor bearing mice. Further, if the isolated population is to undergo successive inoculations in tumor bearing mice, upon each successive inoculation, the number of microorganisms in the inoculate and the time of infection may be reduced to increase the stringency of selection for tumor-specific isolates. Additionally, the isolated populations can be cultured to isolate single colony clones using standard techniques. The isolated microorganisms may be used also in in vitro assays to determine their relative infective and selective abilities as compared to the "wild type" parent strain which did not undergo an in vivo selection procedure.

6.1.3. Isolation By In Vitro Chemotaxis Using Medium Conditioned By the Target Tumor Cell Another embodiment of the present invention is to provide methods for isolating super-infective and/or tumor cell-specific vectors by chemotaxis so that the isolated microorganisms have increased chemotactic ability towards tumor cell secretory products. The method entails using capillary tubes which are loaded with either liquid control medium or medium that has been conditioned by the target tumor cell as described by Adler (1973, J. General Microbiology 74:77–91). Conditioned medium is medium in which the target cells have been grown and subsequently has been filtered to remove the cells. One end of the capillary is sealed in a flame; the capillary is then quickly passed several times through a flame and is immediately plunged open end down into a beaker containing either the conditioned or control medium. As the capillaries cool, the liquid is drawn up inside.

The loaded capillary tubes are inserted open end down into a centrifuge tube containing medium and a suspension of the pre-selected microorganism. After a pre-determined period of incubation at 37° C. in which the microorganism chemotacts into the capillary tubes, the capillary tubes are removed with forceps, the sealed ends are opened and the opened capillaries are transferred into centrifuge tubes containing nutrient medium appropriate for the particular microorganism. It is important that the upper tips of the capillary tubes are covered with an appropriate medium for the particular type of microorganism to assure quantitative recovery of the microorganism from the capillary tubes during centrifugation. The capillary tubes are centrifuged, for example, at 4000×g for 4 minutes, to force the microorganism out of the tube. The capillary tubes are removed, the microorganism resuspended, and an aliquot spread onto the appropriate medium in either solid or liquid form to allow for quantitation.

Significant increases in the number of microorganisms entering into the capillary tubes containing conditioned medium as compared to controls indicates a positive chemotactic response toward secreted products of the target cell found in the conditioned medium. The populations isolated by this in vitro technique can undergo successive chemotaxis assay isolation or be used to isolate single colony clones. These clones or populations can be compared to the "wild type" parent strain in their ability to distinguish between the target cancerous cell and the non-cancerous counterpart cell as well as for super-infective ability.

For an illustrative example of super-infective, tumor-specific vectors isolated by in vitro chemotaxis using tumor cell-conditioned medium, see Section 8, infra.

6.1.4. Isolation of Mutagenized Vectors

In any of the above-described methods for isolating super-infective, tumor-specific microorganisms, the "wild type" parent microorganism can be subjected first to mutagenesis before the microorganism is subjected to any isolation or selection procedure of the present invention. For example, bacteria are subjected to treatment with nitrosoguanidine and ultraviolet B irradiation so that the hereditary genetic material is modified resulting in the altered expression of genes, both qualitatively and quantitatively, in the microorganism. Other types of chemical and high-energy mutagenesis are well known in the art. For example, alkylating agents such as dimethyl nitrosamine or ethyl methane sulfonate, or intercalating agents, such as ethidium bromide. Other approaches include transposon mutagenesis to introduce genetic flocks or fusions of genes with new promoters. Any mutagen can be used in the present invention to create mutant strains of microorganisms which may then undergo any of the selection methods of the present invention.

For an illustrative example of mutagenesis, see Section 7.1, infra.

6.2. Genetic Manipulation of the Selected Vectors For Delivery of Genes and/Or Gene Products To the Target Solid Tumor Cells as Well as For Attenuation of Virulence

6.2.1. Genetic Manipulation For Delivery of Genes and/Or Gene Products To the Target Site After the selection processes described above in which one obtains a super-infective, tumor-specific vector, one can genetically engineer such vectors so that any desired gene or gene product is delivered to a target site, preferably the site of a solid tumor, more preferably, into the tumor cell itself, the necrotic areas of the tumor or into tumor-associated lymphocytes and macrophages. Additionally, one can genetically alter naturally occurring microorganisms which have a natural ability to infect tumor cells and/or be tumor-cell specific. These vectors are genetically engineered by a wide variety of methods known in the art, for example, transformation or electroporation. In a preferred embodiment of the present invention the vectors are engineered to deliver suicide genes to the target tumor cells. These suicide genes include pro-drug converting enzymes, such as *Herpes simplex* thymidine kinase (TK) and bacterial cytosine deaminase (CD). TK phosphorylates the non-toxic substrates acyclovir and ganciclovir, rendering them toxic via their incorporation into genomic DNA. CD converts the non-toxic 5-fluorocytosine (5-FC) into 5-fluorouracil (5-FU), which is toxic via its incorporation into RNA. Additional examples of pro-drug converting enzymes encompassed by the present invention include cytochrome p450 NADPH oxidoreductase which acts upon mitomycin C and porfiromycin (Murray et al., 1994, J. Pharmacol. Exp. Therapeut. 270:645–649).

Prodrug converting enzymes are being widely employed for use in gene therapy of malignant cancers (Vile and Hart, 1993, Cancer Res. 53:3860–3864; Moolten and Wells, 1990, J. Natl. Cancer Inst. 82:297–300; Wagner, et al., 1981, Proc. Natl. Acad. Sci. USA 78:1441–1445; Mullen, 1994, Cancer Res. 54:1503–1506; Huber et al., 1993, Cancer Res. 53:4619–4625; Waldman et al., 1983, J. Biol. Chem. 258:11571–11575; Mullen, et al., 1992, Proc. Natl. Acad. Sci. 89:33–37; Austin and Huber, 1993, Mol. Pharmacol. 43:380–387). Table 2 is an illustrative list of pro-drug converting enzymes (Bagshawe, 1995, Drug Dev. Res. 34:220–230).

Prodrug converting enzymes have been expressed in several bacteria. The *Herpes simplex* virus has been expressed in *E. coli* (Garapin, 1980, Proc. Natl. Acad. Sci. USA 78:815–819; Waldman et al., 1983, J. Biol. Chem. 258:11571–11575). Similarly, Simula et al., 1993, Toxicology 82:3–20, expressed the prodrug converting enzyme cytochrome p450 oxidoreductase in *Salmonella typhimurium* which confered sensitivity to mitomycin.

TABLE 2

REPRESENTATIVE PRO-DRUG CONVERTING ENZYMES FOR USE IN VECTOR THERAPY

| Enzyme | Pro-drug | Reference |
|---|---|---|
| Carboxypeptidase G2 | benzoic acid mustards | Bashawe et al., 1988; Springer et al., 1990 |
| | aniline mustards | Davies et al., 1994 |
| | phenol mustards | Springer et al. |
| Beta-glucuronidase | p-hydroxyaniline mustard glucuronide | Roffler et al., 1991 |
| | epirubicin-glucuronide | Halsma et al., 1992 Mitaku et al., 1994 |
| Penicillin-V-amidase | adriamycin-N phenoxyaceryl | Kerr et al., 1990 |
| Penicillin-G-amidase | N-(4'-hydroxyphenyl-acetyl)-palytoxin doxorubicin | Bignami et al., 1992 |
| | melphalan | Vrudhula et al., 1993 |
| β-lactamase | nitrogen mustard-cephalosporin β-phenylenediamine vinblastine derivative-cephalosporin | Alexander et al., 1991 |
| | cephalosporin mustard | Meyer et al., 1993 Svensson et al, 1993 |
| β-glucosidase | cyanophenylmethyl-β-D-gluco-pyranosiduronic acid | Rowlandson-Busza et al., 1991 |
| Nitroreductase | 5-(adaridin-1-yl-)2, 4-dinitrobenzamide | Knox et al., 1988; Somani and Wilman, 1994 |
| Carboxypeptidase A | methotrexate-alanine | Haenseler et al., 1992 |

Bagshawe et al., 1988, Br. J. Cancer 58:700–703.
Springer et al., 1990, J. Med. Chem. 33:677–681.
Davies et al., 1994, Ann. Oncol. 5 (Suppl 5):73(abstr).
Springer et al., 1994, A novel bisiodo-phenol mustard in antibody-directed enzyme pro-drug therapy (ADEPT). In: Programme of Eleventh Hammersmith Conference. Advances in the Application of Monoclonal Antibodies. London: Hammersmith Hospital (abstr).
Haisma et al., 1992(a), Cancer Immunol. Immunother. 34:343–348.
Roffler et al., 1991, Biochem. Pharmacol. 42:2062–2065.
Haisma et al., 1992(b), Br. J. Cancer 88:474–478.
Mitaku et al., 1994, Ann. Oncol. 5 (Suppl 5):76 (abstr).
Kerr et al., 1990, Cancer Immunol. Immunother. 31 :202–206.
Bignami et al., 1992, Cancer Res. 52:5759–5764.
Vrudhula et al., 1993, J. Med. Chem. 38:919–923.
Alexander et al., 1991, Tetrahedron Lett. 32:3296–3272.
Meyer et al., 1993, Cancer Res. 53:3956–3963.
Svensson et al., 1992, Bioconj. Chem. 3:176–181.
Rowlandson-Busza et al., 1991, Cytotoxicity following specific activation of amygladin. In: Monoclonal Antibodies, Epenetos AA (ed), London: Chapman & Hall, pp. 179–183.
Knox et al., 1988, Biochem. Pharmacol. 41:4661–4669.
Somani et al.; 1994, Ann. Oncol. 5 (Suppl 5):73 (abstr).
Haenseler, E., Esswein, A., Vitols, K. S., Montejano, V., Mueller et al., 1992, Biochemistry 31 :214–220.

However, pro-drug converting enzymes such as the TK and CD enzymes, when synthesized in bacteria such as Salmonella or *Escherichia coli*, are not normally secreted from the bacteria. Accordingly, the expression construct is designed such that the microorganism-produced gene products are secreted by the microorganism. Thus, TK or CD are able to generate phosphorylated acyclovir, ganciclovir, or 5-FU, within the target tumor cell cytoplasm and interstitial spaces of the target tumor. Secretion of TK and CD is achieved by introducing into the expression construct a secretory signal sequence, for example, from the β-lactamase gene (Talmadge et al., 1980, Proc. Natl. Acad. Sci. USA 77:3369–3373).

Alternate signal sequences, in addition to β-lactamase, are also encompassed by the present invention. Bacteria, for example, are known to have several means for secretion into the periplasm and the outside media. The most typical secretion sequences are N-terminal signal sequences containing hydrophobic transmembrane spanning domains. These sequences serve to guide the protein through the membrane and are removed as- or after the protein crosses the membrane. Prokaryotic and eukaryotic N-terminal signal sequences are similar and it has been shown that eukaryotic N-terminal signal sequences are capable of functioning as secretion sequences in bacteria. In a preferred embodiment, the gene encoding the enzyme β-lactamase (penicillinase) is used as the source of the signal sequence. This signal sequence is a well studied example of a bacterial enzyme which is secreted both into the periplasm and into the external media.

Further, some bacterial proteins utilize a different secretion signal which is located at the C-terminus. The entero-invasive *E. coli* hemolysin A (hlyA) is the best studied member of this group. It has been shown that the secretion signal is present in the last 60 amino acids of that protein and that transfer of this domain to other proteins can result in their direct secretion into the media when the accessory proteins from the hemolysin operon (hylC, A, B, & D) are present (Su et al., 1992, Microbial Pathogen. 13:465–476). An illustrative list of secreted proteins reviewed by Pugsley is presented in Table 3, (Pugsley A. P., 1988, Protein secretion across the outer membrane of gram-negative bacteria. In: Protein Transfer and organelle Biogenesis, R. C. Dand and P. W. Robbins (eds), Academic Press, Inc., Harcourt Brace Jovanovich, Publishers, San Diego, pp 607–652).

TABLE 3

SOURCES OF SECRETION SIGNALS FOR PRO-CONVERTING ENZYMES

| Protein | Organism | Location in Transfected *E. coli* and type of signal | Ref. No. |
|---|---|---|---|
| Chitinase | *Serratia marcescens* | released into medium N-terminal signal | 14 |
| α-Hemolysin | *E. coli* | released into medium C-terminal signal | 9 |
| Heat labile enterotoxin I | various *E. coli* strains | Similar to cholera toxin 2 subunits (A&B); N-terminal signal in both; primarily in periplasm | 12, 7, 29 |
| Heat-stable enterotoxin I | various *E. coli* strains | N-terminal signal peptide; secreted into the media | 11, 28 |
| Heat-labile enterotoxin II | various *E. coli* strains | N-terminal signal peptide | 17 |
| Pullulanase | *Kelbsiella pneumoniae* | Release into the medium; N-terminal signal peptide | 3, 27, 6 |
| Serine protease | *S. marcencens* | Secreted into the medium; N-terminal signal peptide | 31 |
| Pectate lyase | *Erwinia chrysanthemi* | Mainly in the periplasm | 15, 5 |
| Pectate lyase | *E. carotovara* | Periplasm | 18, 32 |
| Protease | *E. chrysanthemi* | Secreted into the medium | 30, 1 |
| Aerolysin | *Aeromonas hydrophila* | Periplasm, N-terminal signal sequence (processed) | 13 |
| Phospholipase C | *Pseudomonas aeruginosa* | not secreted by *E. coli* N-terminal signal sequence | 4, 19, 26 |
| Exotoxin A | *P. aeruginosa* | not secreted by *E. coli* | 10 |
| Cholera toxin | *Vibrio cholerae* | Mainly periplasmic; 2 subunits | 25, 20 |
| Hemolysin | *V. cholerae* | Periplasm | 21 |
| DNase | *V. Cholerae* | Periplasm | 22, 8 |
| Thermostable Hemolysin | *V. parahaemolyticus* | Periplasm N-terminal signal peptide | 24 |
| IgA protease | *Haemolphilis influenzae* | Periplasm | 2 |

TABLE 3-continued

SOURCES OF SECRETION SIGNALS FOR
PRO-CONVERTING ENZYMES

| Protein | Organism | Location in Transfected E. coli and type of signal | Ref. No. |
|---|---|---|---|
| IgA protease | Nisseria gonorrhoeae | Secreted into the medium | 16 |
| Pertussis toxin | Bordetella pertussis | Periplasm; 5 subunits all with N-terminal signal peptides | 23 |

1. Barras et al., 1986, FEMS Microbiol. Lett. 34:343–348.
2. Bricker et al., 1983, Proc. Natl. Acad. Sci. USA 80:2681–2685.
3. Chapon et al., 1985, J. Bacteriol. 164:639–645.
4. Coleman et al., 1983, J. Bacteriol. 153:909–915.
5. Collmer et al., 1985, J. Bacteriol. 161:913–920.
6. d'Enfert et al., 1987, EMBO J. 6:3531–3538.
7. DaRas et al., 1980, Nature 288:499–501.
8. Focareta et al., 1985, FEMS Mcrobiol. Lett. 29:161–166.
9. Goebel et al., 1984, Structure, function and regulation of the plasmid-encoded hemolysin determinant of E. coli. In Plasmids in Bacteria, D. R. Hehnski, S. N. Cohen, D. B. Cloewell, D. A. Jackson, and A. Hollaender (eds), pp. 791–805, Plenum, New York.
10. Gray et al., 1984, Proc. Natl. Acad. Sci. USA 81:2645–2649.
11. Guzmin-Verduzco et al., 1983, J. Bacteriol. 154:146–151.
12. Hirst et al., 1984, Proc. Natl. Acad. Sci. USA 81:7752–7756.
13. Howard et al., 1986, Mol. Gen. Genet. 204:289–295.
14. Jones et al., 1986, EMBO J. 5:2377–2383.
15. Keen et al., 1984, J. Bacteriol. 159:825–831.
16. Koomey et al., 1982, Proc. Natl. Acad. Sci. USA 79:7881–7885.
17. Lee et al., 1983, Infect. Immun. 42:264–268.
18. Lei et al., 1985, Gene 35:63–70.
19. Lory et al., 1983, Gene 22:95–101.
20. Mekalanos et al., 1983, Nature 306:551–557.
21. Mercuric et al., 1985, Mol. Gen. Genet. 200:472–475.
22. Newland et al., 1985, Infect. Immun. 47:691–696.
23. Nicosia et al., 1986, Proc. Natl. Acad. Sci. USA 83:4631–4635.
24. Nishibuchi et al., 1985, J. Bacteriol. 162:558–564.
25. Pearson et al., 1982, Proc. Natl. Acad. Sci. USA 79:2976–2980.
26. Pritchard et al., 1986, J. Bacteriol. 167:291–298.
27. Pugsley, A. P., 1988, Protein secretion across the outer membrane of gram-negative bacteria. In: Protein Transfer and Organelle Biogenesis, R. C. Dand and P. W. Robbins (eds), Academic Press, Inc., Harcourt Brace Jovanovich, Publishers, San Diego, pp 607–652.
28. So et al., 1980, Proc. Natl. Acad. Sci. USA 77:4011–4015.
29. Spicer et al., 1982, J. Biol. Chem. 257:5716–5721.
30. Wandersman C. (unpublished results cited in Pugsley, 1988).
31. Yanigida et al., 1986, J. Bacteriol. 166:937–944.
32. Zink et al., 1985, Appl. Environ. Microbiol. 49:714–717.

In another embodiment of the present invention, the desired genes expressed from the expression constructs are under the specific regulatory control of certain types of promoters. These promoters may be either constitutive, in which the genes are continually expressed, inducible, in which the genes are expressed only upon the presence of an inducer molecule(s) or cell-type specific control, in which the genes, including but not limited to suicide genes, are expressed only in certain cell types. Further, expression of foreign genes including prodrug converting enzymes frequently alters the phenotype of the bacteria. Therefore, it would be an advantage to drive the expression of a prodrug converting enzyme under exogenous control. This would allow exploitation of the bacterial phenotypes such as tumor targeting and amplification, after which time it would be beneficial to express the prodrug enzyme. Inducible promoters drive gene expression under specific conditions. Furthermore, exogenously inducible promoters respond to specific stimuli including chemical signals which can be artificially introduced. It would be an advantage to drive the expression of a prodrug enzyme using an exogenously introduced agent which is approved for use in humans. The "SOS" response of bacteria (Friedberg et al., In: DNA Repair and Mutagenesis, pp. 407–455, Am. Soc. Microbiol. Press, 1995) is a response inducible by numerous agents including chemotherapeutic alkylating agents such as mitomycin (Oda et al., 1985, Mutation Research 147:219–229; Nakamura.et al., 1987, Mutation Res. 192:239–246; Shimda et al., 1994, Carcinogenesis 15:2523–2529) which is approved for use in humans. Promoter elements which belong to this group include umuC, sulA and others (Shinagawa et al., 1983, Gene 23:167–174; Schnarr et al., 1991, Biochemie 73:423–431). The sulA promoter includes the ATG of the sulA gene and the following 27 nucleotides as well as 70 nucleotides upstream of the ATG (Cole, 1983, Mol. Gen. Genet. 189:400–404). Therefore, it is useful both in expressing foreign genes and in creating gene fusions for sequences lacking initiating codons.

In one embodiment, for example, the expression of the gene is controlled by a bacterial promoter which is activated in specific target cells. In a preferred mode of this embodiment, the bacterial promoter is activated primarily in specific target cells. In another embodiment, for example, the expression of the gene is controlled by a bacterial promoter which is activated only in specific tumor cells. An illustrative example of an expression construct which expresses a gene under the control of a promoter with the necessary secretion signal sequence is diagrammed in FIG. 1.

In a preferred embodiment of the present invention, the expression of the gene is under the control of a promoter which is active only in the target cell. Microorganism promoters that are specifically or preferentially active in a target tumor cell are isolated by a number of different methods. For example, one method is using IVET (in vivo expression technology) promoter trap procedure for isolating specifically induced genes. This procedure is carried out by taking, for example, a random pool of Salmonella typhimurium DNA insertions generated by Sau3A restriction enzyme and cloning the fragments into the promoter trap vector pIVET (Slauch et al., 1994, Methods Enzymol. 235:481–492; Mahan et al., 1993, Science 259:686–688). The cloning site is at the position of the promoter for the purA gene which is required for the synthesis of cyclic AMP. This representative pool is transfected back into Salmonella typhimurium and an integration event is induced which results in replacement of the endogenous purA gene. The population of bacteria carrying an integrated IVET plasmid is allowed to infect an animal bearing a solid tumor of the cell type of choice and after 24 hours bacteria are isolated from the tumor. Only those bacteria that received a plasmid whose random piece of Sau3A restricted DNA acts as a promoter within the tumor cells is capable of surviving. In addition to controlling the transcription of purA, the Sau3A restricted DNA promoter also controls the expression of the β-galactosidase gene. Two types of promoters are isolated which allow the survival of bacteria within tumors, constitutive and regulated. The constitutive promoter continues to control the positive expression of both genes, inside and outside of the tumor. Whereas the regulated promoter is no longer active in cells other than the target cell.

Another method for identifying promoters that are active in tumors is to identify tumor-specifically induced microbiological gene products using two dimensional gel electrophoresis. For example, to determine which gene products are specifically or preferentially expressed in melanoma cells rather than macrophages, the method entails three parallel infections which proceed in tandem: (1) $5 \times 10^7$ clonal microorganisms are allowed to infect $5 \times 10^6$ melanoma cells, (2) $5 \times 10^7$ clonal microorganisms are allowed to infect $5 \times 10^6$ macrophages, and (3) $5 \times 10^7$ clonal microorganisms are maintained in growth phase in LB broth. After a 30 minute infection the cells are washed with DMEM with 10 μg/ml gentamicin (for melanoma cells), RPMI 1640 with 10 μg/ml gentamicin (for macrophages) and LB without gentamicin (for free microorganisms). After two hours the cells are pretreated with 50 mg/ml cyclohexamide to inhibit host cell protein synthesis for 15 minutes. The cells are then washed and placed in labeling medium (minus methionine) containing 75 μCi/ml $^{35}$S-methionine for 30 minutes, followed by 1 hour in normal medium. The cells are then harvested, denatured in 7M urea buffer and subjected to isoelectrofocusing (IEF) followed by sodium dodecylsulfate (SDS) polyacrylamide gel electrophoresis (PAGE) and analysis by autoradiography. Gene products specifically expressed in melanoma cells appear as protein spots from microorganism-infected melanomas but not from microorganism-infected macrophages or from free microorganisms. The microorganismal genes that are specifically expressed are cloned from a λgt11 expression library using antiserum prepared from proteins derived from preparative IEF and SDS-PAGE gels. Subsequent cloning from a cosmid library results in DNA fragments containing the promoter elements for the tumor-specific expressed gene product.

Yet another method for isolating promoters which are specifically or preferentially activated in the target tumor cells is transposon mutagenesis. Transposon mutagenesis results in a pool of random mutants which can be tested for their ability to survive in epithelial cells but not in target tumor cells. Mutants are first tested for their continued ability to persist in epithelial cells. Mutants no longer able to survive will be selected against. Surviving mutants are picked at random and placed in a numbered array using 96 well plates. The target tumor cells are grown in 96 well plates and individually infected with a microorganism at a microorganism to host ratio of about 10:1 for 30 minutes, followed by washing and treatment with 10 μg/ml gentamicin. After 24 hours the plates are rinsed and stained with 0.4% trypan blue to determine the ratio of living cells(clear) to dead cells (blue) using a 96 well plate reader. Microorganisms which are unable to survive within the target tumor cell are recovered from the original numbered plate. The genes are then cloned using the transposon as a genetic marker to isolate the DNA containing the tumor-specific expressed gene and its promoter.

The vectors which can express the various pro-drug or "suicide genes" when given to the host should not confer antibiotic resistance to the host and more importantly the bacteria should remain as sensitive to as many antibiotics as possible. Therefore, these vectors should not carry any antibiotic resistance markers. This can pose a problem in maintaining the expression vectors in the bacteria in absence of selective pressure. However, the are a number of methods in which the vectors can be stably maintained without resorting to antibiotic resistance. For example, one such method is the construction of chromosomally integrated vectors expressing pro-drug converting enzymes or other "suicide genes" as described by Donnenberg, 1991, Am. Soc. Microbiol., Annual Meeting, Abstract B-111, p.4; Donnenberg and Kaper, 1991, Infect. Immun. 59:4310–4317; and Ried and Collmer, 1987, Gene 57:239–246. Another method is the construction of stable episomal plasmids encoding "suicide genes" or pro-drug converting enzymes using a balanced lethal system. Such balanced lethal systems are defined by the fact that the vector encodes for a function that compensates for a deficiency in the bacteria, such that the presence of the vector is essential for the survival of the bacteria. Such a system is described by Galan et al., 1990, Gene 94:29–35. This system has the advantage over chromosomal integration in that the plasmids are multicopy and, therefore, achieve higher expression levels.

6.2.2. Genetic Manipulation For Attenuation of Virulence

Many of the microorganisms encompassed by the present invention are causative agents of diseases in humans and animals. For example, sepsis from gram negative bacteria is a serious problem because of the high mortality rate associated with the onset of septic shock (R. C. Bone, 1993, Clinical Microbiol. Revs. 6:57–68). Therefore, to allow the safe use of these vectors in both diagnostics and treatment of humans and animals, the microorganism vectors are attenuated in their virulence for causing disease. In the present invention, attenuation, in addition to its traditional definition in which a microorganism or vector is modified so that the microorganism or vector is less pathogenic, is intended to include also the modification of a microorganism or vector so that a lower titer of that derived microorganism or vector can be administered to a patient and still achieve comparable results as if one had administered a higher titer of the parental microorganism or vector. The end result is to reduce the risk of toxic shock or other side effects due to administration of the vector to the patient. Such attenuated microorganisms are isolated in a number of techniques. Such methods include use of antibiotic-sensitive strains of microorganisms, mutagenesis of the microorganisms, selection for tumor-specific, super-infective microorganism mutants in culture or in tumor-bearing animals, selection for microorganism mutants that lack virulence factors necessary for survival in normal cells, including macrophages and neutrophils, and construction of new strains of microorganisms with altered cell wall lipopolysaccharides. For example, in Section 6.1 et seq. where methods are described for the isolation of super-infective, tumor-specific vectors, these same methods are also methods for isolating attenuated vectors; super-infective, tumor cell-specific vectors are by definition attenuated. As the vectors are highly specific and super-infective, the difference between the number of infecting bacteria found at the target tumor cell as compared to the non-cancerous counterparts becomes larger and larger as the dilution of the microorganism culture is increased such that lower titers of microorganism vectors can be used with positive results.

Further, the microorganisms can be attenuated by the deletion or disruption of DNA sequences which encode for virulence factors which insure survival of the microorganisms in the host cell, especially macrophages and neutrophils, by, for example, homologous recombination techniques and chemical or transposon mutagenesis. For example, a number of these virulence factors have been identified in Salmonella. Many, but not all, of these studied virulence factors are associated with survival in macrophages such that these factors are specifically expressed within macrophages due to stress, for example, acidification, or are used to induced specific host cell responses, for example, macropinocytosis, Fields et al., 1986, Proc. Natl. Acad. Sci. USA 83:5189–5193. Table 4 is an illustrative list of Salmonella virulence factors which, if deleted by homologous recombination techniques or chemical or transposon mutagenesis, result in attenuated Salmonella.

TABLE 4

REPRESENTATIVE VIRULENCE FACTORS FOR *SALMONELLA TYPHIMURIUM* AND OTHER BACTERIA

| Virulence Factor or Loci, Specific Stress Overcome or Stimulated Response | Reference |
|---|---|
| Acidification | Alpuche-Aranda et al., 1992 |
| 5'-adenosine monophosphate | Biochenko and Levashev, 1987 |
| Cytolysin | Libbey et al., 1994 |
| Defensin resistance loci | Fields et al., 1989 |
| DNAK | Buchmeier and Hefferon, 1990 |
| Fimbriae | Ernst et al., 1990 |
| GroEL | Buchmeier and Hefferon, 1990 |
| Induced Macropinocytosis | Alpuche Aranda, et al., 1994 |
| | Ginocchio et al., 1992 |
| | Jones et al., 1993 |
| Inv loci | Betts and Finlay, 1992 |
| | Galon and Curtis III |
| | Ginocchio et al., 1992 |
| Lipoprotein | Stone et al., 1992 |
| LPS | Gianeiella et al., 1973 |
| | Stone et al., 1992 |
| Lysosomal fusion inhibition | Ishibashi et al., 1992 |
| Macropage survival loci | Fieldsetal., 1989 |
| Oxidative stress (Sox; in *E. coli*) | Nunoshiba et al., 1993 |
| PhoP and PhoQ | Behlau and Miller, 1993 |
| | Groisman et al., 1993 |
| | Miller et al., 1989 |
| Pho activated genes (pag; e.g., pagB and pagC) | Abshire and Neidhardt, 1993 |
| | Hefferon et al., 1992 |
| | Miller et al., 1992 |
| | Miller et al., 1989 |
| | Pulkkinen and Miller, 1991 |
| | Stone et al., 1992 |
| PhoP and PhoQ regulated genes (prg) | Miller et al., 1989 |
| | Behlau and Miller, 1993; 1994 |
| Porins | Tufano et al., 1988 |
| Serum resistance peptide | Hackett et al., 1987 |
| Virulence factors | Abshir and Neidhardt, 1993 |
| | Loos and Wassenaar, 1994 |
| | Mahan et al., 1995 |
| | Sansonetti, 1992 |
| Virulence plasmid | Gulig and Curtiss, 1987 |
| | Rhen et al., 1993 |
| | Riikonen et al., 1992 |
| spvB (virulence plasmid) | Fierer et al., 1993 |
| traT (virulence plasmid) | Rhen and Sukupolvi, 1988 |
| ty2 | Elsinghorst et al., 1989 |

Abshiro et al., 1993, J. Bacteriol. 175:3734–3743
Alpuche-Aranda et al., 1992, Proc. Natl. Acad. Sci. USA 89:10079–83
Alpuche-Aranda et al., 1994, J. Exp. Med. 179:601–6088
Baumler et al., 1994, Infect. Immun. 62:1623–1630
Behlau et al., 1993, J. Bacteriol. 175:4475–4484
Belden et al., 1994, Infect. Immun. 62:5095–5101
Betts et al., 1992, Can. J. Microbiol. 38:852–7
Boichenko et al., 1987, Bull. Eksp. Biol. Med. 103:190–2
Boichenko et al., 1988, Zh. Mikrobiol. Epidemiol. Emmunobiol. 7:9–11
Boichenko et al., 1985, Zh. Mkrobiol. Epidemiol. Immunobiol. 12:67–9
Bowe et al., 1994, Methods Enzymol. 236:509–26
Buchmeier et al., 1989, Infect. Immun. 57:1–7
Buchmeier et al., 1990, Science 248:730–732
Buchmeier et al., 1995, J. Cldn. Invest. 95:1047–53
Buchmeier et al., 1993, Mol. Microbiol. 7:933–936
Dragunsky et al., 1989, J. Biol. Stand. 17:353–60
Emoto et al., 1993, J. Immunol. 150:3411–3420
Ernst et al., 1990, Infect. Immun. 58:2014–2016
Elsinghorst et al., 1989, Proc. Natl. Acad. Sci. USA 86:5173–5177
Fields et al., 1986, Proc. Natl. Acad. Sci. USA 83:5189–93
Fields et al.,1989, Science 243:1059–62
Fierer et al., 1993, Infect. Immun. 61:5231–5236
Gianella et al., 1973, J. Infect. Dis. 128:69–75
Galan et al., 1989, Microb. Pathog. 6:433–443
Galan et al., 1990, Infect. Immun. 58:1879–1885
Ginocchio et al., 1992, Proc. Natl. Acad. Sci. USA 89:5976–5980
Gulig et al., 1987, Infect. Immun. 55:2891–901
Hackett et al., 1987, J. Infect. Dis. 1 55:540–549
Heffeman et al., 1992, J. Bacteriol. 174:84–91
Ishibashi et al., 1992, Microb. Pathog. 13:317–323
Libby et al., 1994, Proc. Natl. Acad. Sci. USA 91:489–493
Loos et al., 1994, Immun. Infekt. 22:14–19
Mahan et al., 1995, Proc. Natl. Acad. Sci. USA 92:669–673
Miller et al., 1989, Proc. Natl. Acad. Sci. USA 86:5054–5058
Miller et al., 1992, Infect. Immun. 60:3763–3770
Nunoshiba et al., 1993, Proc. Natl. Acad. Sci. USA 90:9993–9997
Pollack et al., 1986, Nature 322:834–836
Pulkkinen and Miller, 1991, J. Bacteriol. 173:86–93
Rhen et al., 1993, Mol. Microbiol. 10:45–56
Rhen et al., 1988, Microb. Pathog. 5:275–285
Riikonen et al., 1992, Microb. Pathog. 13:281–291
Sansonetti, 1992, Rev. Prat. 42:2263–2267
Stone et al., 1992, J. Bacteriol. 174:3945–3952
Tufano et al., 1988, Eur. J. Epidemiol. 4:110–114

Yet another method for the attenuation of the isolated vectors is to modify substituents of the microorganism which are responsible for the toxicity of that microorganism. For example, lipopolysaccharide (LPS) or endotoxin is primarily responsible for the pathological effects of bacterial sepsis. The component of LPS which results in this response is lipid A (LA). Elimination or mitigation of the toxic effects of LA results in an attenuated bacteria since 1) the risk of septic shock in the patient would be reduced and 2) higher levels of the bacterial vector could be tolerated. *Rhodobacter (Rhodopseudomonas) sphaeroides* and *Rhodobacter capsulatus* each possess a monophosphoryl lipid A (MLA) which does not elicit a septic shock response in experimental animals and, further, is an endotoxin antagonist. Loppnow et al., 1990, Infect. Immun. 58:3743–3750; Takayma et al., 1989, Infect. Immun. 57:1336–1338.

Known similarities in lipid metabolism and genetic organization of lipid metabolic genes between *Rhodobacter sphaeroides* and other gram negative bacteria and the ability of Rhodobacter genes to complement *E. coli* mutations (Benning and Somerville, 1992(A), J. Bacteriol. 174:6479–6487; 1992(B), J. Bacteriol. 174:2352–2360; Carty et al., 1994, FEMS Microbiol. Lett. 118(3):227–231) demonstrate that, for example, Salmonella and other bacteria can be genetically altered to produce MLA, thereby reducing its potential of inducing septic shock. A preferred embodiment of the present invention is a Salmonella spp. strain that expresses MLA rather than LA and also expresses HSV TK under the control of a tumor-specific promoter.

As an illustrative example, the generation of MLA producing *Escherichia coli* or *Salmonella typhimurium* entails constructing a DNA gene library composed of 10 kB fragments from *Rhodobacter sphaeroides* which is generated in λgtll or pUC19 plasmids and transfected into *E. coli*. Clones which produce MLA are positively selected by using an antibody screening methodology to detect MLA, such as ELISA. In another example one generates a cosmid library composed of 40 kB DNA fragments from *Rhodobacter sphaeroides* in pSuperCos which is then transfected into *Salmonella typhimurium*. Clones which produce MLA are positively selected by using an antibody screening methodology to detect MLA, such as ELISA.

Yet another example for altering the LPS of Salmonella involves the introduction of mutations in the LPS biosynthetic pathway. Several enzymatic steps in LPS biosynthesis and the genetic loci controlling them in both *E.coli* and

*Salmonella typhimurium* have been identified (Raetz, 1993, J. Bacteriol. 175:5745–5753 and references therein). Several mutant strains of *Salmonella typhimurium* and *E. coli* have been isolated with genetic and enzymatic lesions in the LPS pathway. One such mutant, firA is a mutation within the gene that encodes the enzyme UDP-3-O(R-30 hydroxymyristoyl)-glycocyamine N-acyltransferase, that regulates the third step in endotoxin biosynthesis (Kelley et al., 1993, J. Biol. Chem. 268:19866–19874). *Salmonella typhimurium* and *E.coli* strains bearing this type of mutation produce a lipid A that differs from wild type lipid A in that it contains a seventh fatty acid, a hexadecandic acid (Roy and Coleman, 1994, J. Bacteriol. 176:1639–1646). Roy and Coleman demonstrated that in addition to blocking the third step in endotoxin biosynthesis, the firA$^-$ mutation also decreases enzymatic activity of lipid A 4' kinase that regulates the sixth step of lipid A biosynthesis.

Once the strain has been attenuated by any of the methods known in the art, the stability of the attenuated phenotype is important such that the strains do not revert to a more virulent phenotype during the course of treatment of a patient. Such stability can be obtained, for example, by providing that the virulence gene is disrupted by deletion or other non-reverting mutations on the chromosomal level rather than epistatically or that the "suicide gene" is stably integrated into the bacterial chromosome.

Another method of insuring the attenuated phenotype is to engineer the bacteria such that it is attenuated in more than one manner, e.g., a mutation in the pathway for lipid A production, such as the firA$^-$ mutation (Hirvas et al., 1991, EMBO J. 10:1017–1023) and one or more mutations to auxotrophy for one or more nutrients or metabolites, such as uracil biosynthesis, purine biosynthesis, and arginine biosynthesis as described by Bochner, 1980, J. Bacteriol. 143:926–933. In a more prefered embodiment of the invention, the bacterial vector which selectively targets tumors and expresses a pro-drug converting enzyme is auxotrophic for uracil, aromatic amino acids, isoleucine and valine and synthesizes an altered lipid A.

6.3. In Vitro Cancer Diagnostics and in Vivo Treatment of Solid Tumors Using Isolated Vectors and Other Vectors

6.3.1. In Vitro Diagnostics

An embodiment of the present invention is to provide methods for use of the vectors of the present invention in in vitro diagnostic assays and diagnostic kits for the detection of solid tumor cancers, including but not limited to melanoma. Also, the kits may comprise tumor-specific non-attenuated vectors. The In vitro diagnostic assays and kits are based on the enhanced specificity towards a cancerous cell rather than its non-cancerous counterpart cell of a vector. For example, and not by way of limitation, a putative solid tumor is biopsied from a patient. The tumor biopsy is minced and digested to a suspension of single cells. Aliquots of the suspension and a non-cancerous counterpart or control cell are cultured and infected with a tumor-specific vector according to the present invention.

After an incubation period, the number of tumor-specific microorganisms which attached to and/or infected the biopsied cells as compared to the non-cancerous counterpart or control cells is determined by any method known to those skilled in the art. A higher number of vectors found associated with the target cell as compared to the non-cancerous counterpart or control cells indicates that the target cell is cancerous, for example, about 5–10 times as many vectors will infect a tumor cell compared to a non-cancerous control cell. A non-cancerous counterpart or control cell is the normal cell from which the tumor cell is derived, for example, for melanoma cells the non-cancerous counterpart or control cell is melanocyte cells, for colon cancer the counterpart cell is colon epithelial cells. In one embodiment the ratio is determined as the number of vectors/target cell. In another embodiment, after infection, the cells are fixed and treated with a stain or antibody which recognizes DNA so that the vector DNA present in the target cell cytoplasm is visualized. The presence of DNA in the target cell cytoplasm indicates that the biopsied target cells are cancerous. In one embodiment of the present invention the diagnostic method comprises exposing a sample of cells which are suspected of being cancer cells to a tumor-specific vector or microorganism. The method also comprises exposing a sample of non-cancerous counterpart cells to the tumor-specific vector or microorganism as a comparative control. After incubating for a time period in which the microorganisms can attach to and/or infect cancer cells, the infectivity of the microorganism or vector for the cells suspected of being cancerous and the non-cancerous counterpart control cells can be compared.

The diagnostic kits of the present invention comprise an effective amount of a tumor-specific vectors. The kits can further comprise an appropriate amount of non-cancerous control cells. The vector and/or cells may be supplied either frozen, lyophilized or growing on solid or in liquid medium. The diagnostic kits can further comprise inert ingredients and other kit components such as vials, packaging components and the like, which are well known to those skilled in the art.

In certain embodiments, the vectors useful for the methods of diagnosis of the present invention can further comprise tumor-specific, attenuated or non-attenuated vectors. In other embodiments, the kits of the present invention can comprise tumor-specific, attenuated or non-attenuated vectors.

For illustrative examples of in vitro diagnostics of solid tumor cancers, including but not limited to melanoma, see Sections 22, 25 and 26.

6.3.2. In Vivo Treatment of Solid Tumors

The vectors for use in in vivo cancer treatment are a subset of the vectors of the present invention. The vectors for in vivo treatment have been attenuated such that, when administered to a host, the vector has been made less toxic to the host and easier to eradicate from the host's system. In a preferred embodiment, the vectors are super-infective, attenuated and specific for a target tumor cell. In a more preferred embodiment, the vectors are also sensitive to a broad range of antibiotics.

In addition, the isolated vectors can encode "suicide genes", such as pro-drug converting enzymes or other genes, which are expressed and secreted by the vector in or near the target tumor. The gene can be under the control of either constitutive, inducible or cell-type specific promoters. In a preferred embodiment, a suicide gene is expressed and secreted only when a vector has invaded the cytoplasm of the target tumor cell, thereby limiting the effects due to expression of the suicide gene to the target site of the tumor.

In a preferred embodiment, the vector, administered to the host, expresses the HSV TK gene. Upon concurrent expression of the TK gene and administration of ganciclovir to the host, the ganciclovir is phosphorylated in the periplasm of the microorganism which is freely permeable to nucleotide triphosphates. The phosphorylated ganciclovir, a toxic false DNA precursor, readily passes out of the periplasm of the microorganism and into the cytoplasm and nucleus of the host cell where it incorporates into host cell DNA, thereby causing the death of the host cell.

Another embodiment of the present invention is to provide methods of treatment of solid tumor cancers with isolated attenuated vectors of the present invention. For example, a patient is diagnosed with a solid tumor cancer by any method known in the art, including the in vitro diagnostic methods of the present invention. The vector used in the treatment may already be isolated using the methods of the present invention with target cell lines or using model tumors in mice of the target tissue. In another embodiment, the biopsied tumor cells are used in the selection assay for isolating a vector which is super-infective and tumor-specific for the tumor of the patient. In a preferred embodiment the vector is genetically modified, for example, to lack virulence factors, express a suicide gene or both as described in Section 6.2.2. In addition, the isolated vector is analyzed for sensitivity to antibiotics to insure the eradication of the vector from the patient's body after successful treatment or if the patient experiences complications due to the administration of the isolated vector.

When administered to a patient, e.g., an animal for veterinary use or to a human for clinical use, the vectors can be used alone or may be combined with any physiological carrier such as water, an aqueous solution, normal saline, or other physiologically acceptable excipient. In general, the dosage would range from about 1 to $1\times10^8$ c.f.u./kg, preferably about 1 to $2\times10^2$ c.f.u./kg.

The vectors of the present invention can be administered by a number of routes, including but not limited to: orally, topically, injection including, but limited to intravenously, intraperitoneally, subcutaneously, intramuscularly, intratumorally, i.e., direct injection into the tumor, etc.

The following series of examples are presented by way of illustration and not by way of limitation on the scope of the invention.

7. EXAMPLE

Isolation of Super-Infective, Tumor-Specific *Salmonella typhimurium* in Vitro 7.1. Mutagenesis Before Isolation of Super-Infective, Tumor-Specific Clones A culture of *Salmonella typhimurium* strain #14028 was grown exponentially at 37° C. in minimal medium 56 plus glycerol (0.5%) to $OD^{600}=0.3$, then chilled on ice. An aliquot was removed so that the culture could be titered for colony forming units (c.f.u.) on LB agar plates. The culture was washed and resuspended in Na citrate (0.1M, pH 5.5), incubated with fresh nitrosoguanidine (NG, 50 µg/ml, 20 minutes, 37° C.), washed once by centrifugation, resuspended in medium 56, chilled, and again an aliquot was removed so that the culture could be titered for c.f.u. on LB agar plates. Another aliquot of the NG treated bacteria was diluted (1:5) into LB broth and grown to stationary phase for storage frozen at −80° C. in 12% glycerol.

The remaining bacteria were irradiated with ultraviolet light, dose=50J/m2, λ=254 nm). An aliquot was removed and the cells were then titered for c.f.u. on LB agar plates, with another aliquot diluted 1:4 into LB broth, grown to stationary phase, and stored frozen at −80° C. in 12% glycerol.

The mutagenesis procedures produced an increase in the number of mutations in the strain by four criteria: 1) decreased survival of the bacteria following mutagenesis (nitrosoguanidine=6-fold; ultraviolet B irradiation=400-fold); 2) increased frequency of auxotrophic (nutritional requiring) mutants to (2%); 3) increased frequency of maltose mutants to (2%); 4) increased frequency of galactose⁻ mutants to (0.5%).

7.2. Isolation of Super-Infective *Salmonella Typhimurium* Clones #70 and #71 Specific For Cancer Cells A population of *Salmonella typhimurium* wild type strain #14028 was mutagenized as described in Section 7.1 with nitrosoguanidine and UV irradiation. Briefly, the bacteria were grown exponentially at 37° C. in minimal medium 56 plus glycerol to $OD^{600}=0.3$, chilled on ice, washed, resuspended in Na citrate with 50 µg/ml nitrosoguanidine and incubated for 20 minutes at 37° C. The bacteria were washed once by centrifugation and resuspended in medium 56. The bacteria were then irradiated with UV light at a dose of 50J/m², λ=254 nm.

Prior to infection by Salmonella, human M2 melanoma cells were inoculated into Corning Tissue Culture flasks (25 cm²) at approximately $2\times10^5$ cells/flask in 4 ml DMEM cell culture medium containing penicillin (100 units/ml), and streptomycin (100 µ/ml), and incubated overnight in a 37° C., gassed (5%CO2), humidified incubator. The next day the cells were rinsed twice with prewarmed Dulbecco's Minimal Essential medium supplemented with 10% fetal bovine serum (DMEM/FBS) and no antibiotics.

The mutated population of *Salmonella typhimurium* was cultured on LB agar overnight at 37° C. or in a liquid culture. The following day the bacteria were transferred with a platinum wire loop to LB broth or to DMEM/FBS, adjusted in concentration to $OD^{600}=0.1$ (approximately $2\times10^8$ c.f.u./ml), and subjected to further growth at 37° C. on a rotator. Following growth to the desired population density (monitored at an optical density of 600 nm) the bacteria were diluted to a concentration of $10^6$ c.f.u./ml in DMEM/FBS, and incubated at 37° C. an additional 20 minutes.

The mutagenized bacterial population was subjected to a single cycle of infection into- and isolation from human M2 melanoma cells in culture. Portions of the mutagenized population were grown clonally on agar and 20 clones of *Salmonella typhimurium* were separately isolated and tested for their individual infectivity toward human M2 melanoma cells. The bacteria were added to animal cell cultures in 25 cm² Corning Tissue Culture flasks at 4 ml/flask, and incubated with the animal cells in a gassed ($5\%CO^2/95\%$ air), humidified incubator at 37° C. After a 15 minute incubation with the animal cells the bacteria-containing medium was poured off and the cultures were rinsed gently with warmed DMEM/FBS (4 ml) containing gentamicin sulfate (20 µg/ml), an antibiotic that kills extracellular but not intracellular bacteria. The gentamicin sulfate-containing medium was poured off, fresh DMEM/FBS/gentamicin sulfate medium was added, and the cells were incubated for 60 minutes at 37° C. Following the 60 minute incubation with gentamicin sulfate, the medium was poured off, the flasks were rinsed 1× with DMEM/FBS (without gentamicin sulfate), and 1 mM EDTA or an EDTA/trypsin solution (Sigma Chemicals, 1×) in $Ca^{++}/Mg^{++}$ free physiological saline (4 ml) was added. After incubating with EDTA or EDTA/trypsin for 20 minutes at 37° C., the flasks were shaken to suspend the animal cells, and aliquots were removed for quantitation. Animal cells were quantitated in a Coulter Counter™ size-dependent particle counter (Coulter Electronics, Inc.) and bacteria were quantitated by plating aliquots on LB agar, incubating at 37° C., and counting colonies. Quantitation was expressed as the number of infecting (gentamicin resistant) bacteria/$10^6$ animal cells.

Two clones, "70" and "71", were found to be super-infective of melanoma cells, with infection capacities 5–10-fold greater than the mutagenized wild type strain (data not shown). Clones 70 and 71 were also assessed for their relative specificity of the following human cells in culture:

M2 melanoma cells and normal human melanocytes; "CaCo" colon cancer cells and normal human colon epithelium #1790 as depicted in Table 4(A).

TABLE 4(A)

SPECIFIC INVASION OF *S. TYPHIMURIUM* INTO MELANOMA VS MELANOCYTES AND COLON CANCER VS COLON EPITHELIUM IN CELL CULTURE: CLONES "70" AND "71"[+]

| Human Cell Line | Infecting Salmonella/$10^6$ human cells: | | | |
|---|---|---|---|---|
| | Clone 70 | (ratio)* | Clone 71 | (ratio)* |
| normal melanocytes | 1.4 ± 0.2 33 $10^6$ | | 1.2 ± 0.3 × $10^6$ | |
| M2 melanoma | 7.3 ± 2.0 × $10^6$ | (5.2) | 5.7 ± 0.7 × $10^6$ | (4.8) |
| colon epithelium (#1790) | 1.5 ± 0.1 × $10^6$ | | 0.8 ± 0.2 × $10^6$ | |
| colon carcinoma (CaCo) | 7.2 ± 2.0 × $10^6$ | (4.8) | 2.3 ± 0.3 × $10^6$ | (2.9) |

*cancer cell:normal counterpart cell
[+]Results represent averages ± SD for triplicate infections.

The bacterial clones #70 and #71 showed strong invasion preference for melanoma and colon cancer cells over that for normal melanocytes and normal colon epithelial cells.

7.3. Isolation of *Salmonella Typhimurium* Super-Infective Clone #72 By Cycling in Vitro Cell Culture Salmonella wild type strain #14028 was mutagenized with nitrosoguanidine and ultraviolet B irradiation as described in Section 7.1. A starting population of 5×$10^8$ mutagenized bacteria was grown to $OD^{600}$=0.450, diluted in DMEM/FBS to a concentration of 5×$10^7$ c.f.u./ml, and allowed to infect human M2 melanoma cells for 15 minutes. Infecting bacteria were isolated from the melanoma cells, and again allowed to infect fresh, uninfected populations of melanoma cells. The $2^{nd}$ round of infecting bacteria were again isolated and subjected to further cycles of infection into, and isolation from, human M2 melanoma cells. After the completion of 4 such cycles, the population of melanoma-cycled bacteria which is designated $14028^{pop-1}$ was then plated on agar and 100 individual clones were picked and tested for their ability, compared to wild type bacteria, to infect M2 melanoma cells. The results of the selection process on $14028^{pop-1}$ and selected population sub-clones are detailed in Table 5.

Additionally, an aliquot of $14028^{pop-1}$ was subjected to two further cyclings in M2 melanoma cells. This 6×-cycled population was then subjected to 7 cycles of negative selection against normal human melanocytes. The 6×-cycled population was added to a culture of normal human melanocytes and incubated for 15 minutes. The supernatant was collected and was then added back to a fresh culture of normal human melanocytes. This negative selection procedure was carried out 7 times. This 6×-7× cycled population was again added to M2 melanoma cells, allowed to infect the melanoma cells for 15 minutes, and the bacteria were then collected from the M2 cells. This 6×-7×-1× cycled population was designated $14028^{pop-2}$.

The mixed population of 4 times cycled *Salmonella typhimurium*, designated $14028^{pop-1}$, showed a 3-fold increased infectivity of melanoma cells over that of the starting mutagenized population of wild type bacteria. Of the 100 clones isolated from population $14028^{pop-1}$ of Salmonella, two clones, #6 and #72, were found to be significantly super-infective of melanoma cells. The remaining bacterial clones showed infectivity that was similar to or below that of the wild type strain. In the experiment presented in Table 5, clone #6 was about 25-fold, and clone #72 was about 55-fold more infective than the mutagenized wild type strain during a 15 minute infection period. *Escherichia coli*, strain K-12, #CSH 101, was at least two orders of magnitude less infective than wild type *Salmonella typhimurium*, thus, demonstrating the natural ability of *S. typhimurium* to infect certain animal cells.

TABLE 5

INFECTION OF M2 HUMAN MELANOMA CELLS WITH VARIOUS ISOLATED *SALMONELLA TYPHIMURIUM* POPULATIONS IN CULTURE[+]

| Salmonella Strain | Infecting Bacterial/$10^6$ | melanoma cells (% wild type) |
|---|---|---|
| Wild type *S. typhimurium* #14028 (mutagenized) | 3.8 ± 3.0 × $10^4$ | 100 |
| $#14028^{pop-1}$ | 1.1 ± 0.4 × $10^5$ | 290 |
| Clone #6 | 8.6 ± 1.0 × $10^6$ | 2260 |
| Clone #72 | 2.1 ± 0.2 × $10^6$ | 5500 |
| *E. coli* K-12 | <$10^2$ | <1 |

[+]Results represent averages ± SD for triplicate infections.

Over several such experiments shown in Table 5, the infectivity of clone #72 toward melanoma cells varied from 5- to 90-fold over that of the wild type strain. This variation seemed to depend on the bacterial growth density prior to infection of melanoma cells. Therefore, the effect of population density on relative infectivity between wild type and clone #72 was determined.

Wild type *S. typhimurium* and super-infective clone #72 were grown as a lawn on LB agar plates. Portions of the cultures were removed with a platinum loop and inoculated into LB broth at a concentration of approximately 2×$10^8$ c.f.u./ml ($OD^{600}$=0.1). The cultures were then placed on a rotator at 37° C. and optical densities were monitored as a function of population density. At the optical densities indicated, aliquots of bacteria were removed, diluted in melanoma growth medium (DMEM/10% FBS) to a density of 1×$10^6$ c.f.u./ml, and allowed to infect human M2 melanoma cells. Infectivity assays were carried out as described. The results are shown in Table 6.

TABLE 6

INFECTIVITY OF WILD TYPE *S. TYPHIMURIUM* AND SUPER-INFECTIVE CLONE #72 TOWARDS HUMAN MELANOMA CELLS: EFFECT OF BACTERIAL POPULATION DENSITY[+]

| Optical Density: | Salmonella/$10^6$ melanoma | | Infectivity ratio: |
|---|---|---|---|
| (600 nm) | Clone #72 | Wild type | (Clone 72:wild type) |
| 0.200 | -0- | -0- | (no infectivity) |
| 0.300 | 9.0 × $10^3$ | -0- | (infinite) |
| 0.400 | 5.0 × $10^4$ | -0- | (infinite) |
| 0.500 | 4.5 × $10^5$ | 5.0 × $10^3$ | 90:1 |
| 0.600 | 1.2 × $10^6$ | 3.7 × $10^4$ | 32:1 |
| 0.700 | 2.3 × $10^6$ | 2.5 × $10^5$ | 9:1 |
| 0.800 | 3.2 × $10^6$ | 5.6 × $10^5$ | 6:1 |
| 0.900 | 3.6 × $10^6$ | 7.3 × $10^5$ | 5:1 |

[+]Results represent averages of duplicate experiments. Variations between duplicates were < ± 15%.

The results demonstrate that infectivity of both bacterial strains was highly dependent on bacterial population density prior to infection, however, clone #72 was proportionately more infective than the wild type strain at low population densities.

Figure 2A:
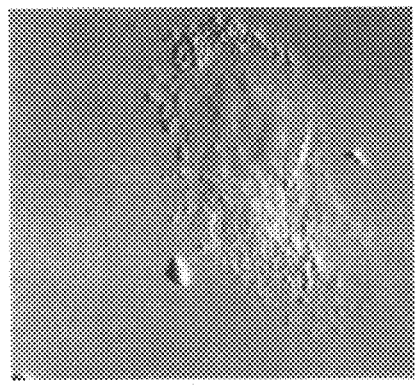
FIGS. 2A–B.
Figure 2B:
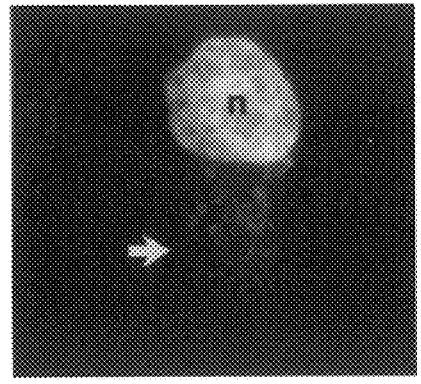
Figure 3A:
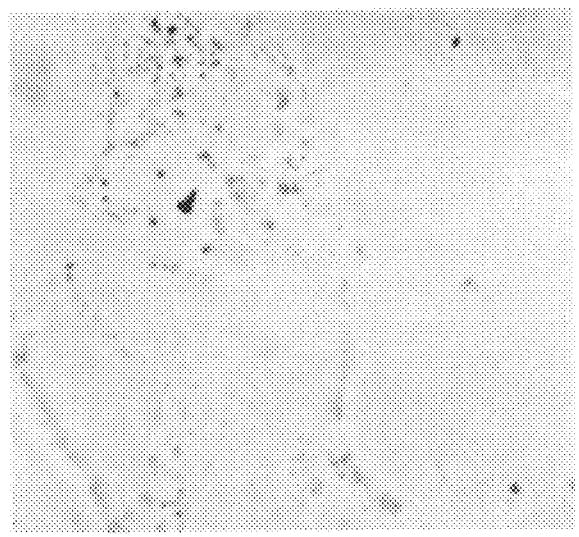
FIGS. 3A–C.
Figure 3B:
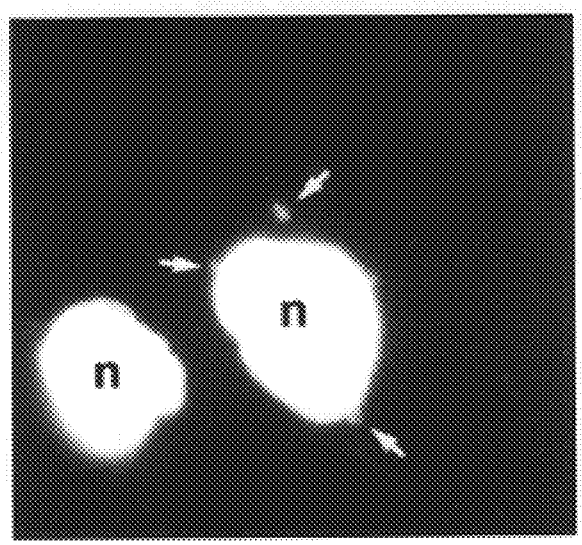
Figure 3C:

The results shown in Tables 5 and 6 were also confirmed by phase and light microscopy which revealed super-- infectivity of a 10× melanoma-cycled population of *Salmonella typhimurium* designated "M10" as shown in FIGS. 2 and 3. It was also found that wild type strain 14028 and clone 72 infected human M2 melanoma cells equally well when grown under anaerobic conditions prior to infection. However, when the strains are grown under aerobic conditions, strain 14028 was strongly suppressed in infectivity, whereas clone 72 remained induced. Thus, clone 72 was infective under either anaerobic or aerobic growth conditions and superinfective compared to wild type under aerobic growth conditions.

7.4. Preferential Selectivety of S. Typhimurium For Cancer Cells: Wild Type Strain vs. Super-Infective Clone #72

Super-infective *Salmonella typhimurium* clone #72 isolated in Section 7.3 was compared to the non-mutagenized wild type strain #14028 for relative infectivity of human M2 melanoma cells, normal human melanocytes, colon cancer cells and normal colon epithelium. The results are shown in Table 7.

TABLE 7

TUMOR SPECIFICITY OF WILD TYPE *S. TYPHIMURIUM* AND SUPER-INFECTIVE CLONE #72 TOWARD VARIOUS NORMAL AND CANCEROUS CELLS IN CULTURE[+]

| Animal Cell Line | Infecting Salmonella/$10^6$ animal cells | | | |
|---|---|---|---|---|
| | wild type | (ratio)* | Clone #72 | (ratio)* |
| normal melanocyte (foreskin, human) | $1.2 \pm 0.7 \times 10^4$ | | $2.7 \pm 0.4 \times 10^5$ | |
| M2 human melanoma | $2.5 \pm 0.6 \times 10^4$ | (2.1) | $1.7 \pm 1.1 \times 10^6$ | (6.3) |
| normal colon epithelium (1790, human) | $6.6 \times 0.8 \times 10^3$ | | $5.2 \pm 3.0 \times 10^5$ | |
| colon cancer (HTB 39, human) | $3.0 \pm 2.0 \times 10^4$ | (4.6) | $9.5 \pm 3.0 \times 10^5$ | (1.8) |
| "normal" fibroblast (3T3, mouse) | $1.8 \pm 1.5 \times 10^4$ | | $5.5 \pm 1.4 \times 10^5$ | |
| transformed macrophage (J774, mouse) | $2.4 \pm 0.6 \times 10^4$ | (1.3) | $4.6 \pm 0.8 \times 10^6$ | (8.4) |

[+]Results represent averages ± SD for triplicate infections.
*cancer cell:normal counterpart cell Each of the two bacterial strains showed invasion preference for human cancer cells over normal cells. Clone #72 was super-infective in all cases when compared to the wild type strain. Further, clone #72 showed a significantly higher degree of invasion specificity for human melanoma cells over normal melanocytes than the wild type strain did.

7.5. Infectivity of *Salmonella typhimurium* Wild Type Strain 14028 and Superinfective Clone 72 Toward Various Human Carcinomas in Culture In another series of experiments, the relative infectivities of clone 72 and wild type strain 14028, toward a variety of human carcinomas growing in culture, was determined. The experimental protocol used is described in Section 7.2. Results are presented in Table 7(A).

TABLE 7(A)

INFECTIVITY OF *SALMONELLA TYPHIMURIUM* WILD TYPE AND SUPERINFECTIVE CLONE 72 TOWARD VARIOUS HUMAN CARCINOMAS IN CULTURE

| | | Salmonella/$10^6$ Human Cells | | |
|---|---|---|---|---|
| Cell Line | Origin of Primary Tumor | Wildtype: 14028 | Clone # 72 | Ratio 72:140 28 |
| M2 | melanoma | $4.0 \pm 3.8 \times 10^4$ | $4.2 \pm 3.5 \times 10^5$ | 11:1 |
| HTB57 | lung | $2.8 \pm 1.3 \times 10^3$ | $4.5 \pm 2.1 \times 10^4$ | 16:1 |
| HTB183 | lung | $1.0 \pm 0.3 \times 10^5$ | $4.1 \pm 1.8 \times 10^5$ | 4:1 |
| HTB54 | lung | $2.1 \pm 0.7 \times 10^4$ | $1.7 \pm 0.2 \times 10^5$ | 8:1 |
| A549 | lung | $3.7 \pm 5.6 \times 10^4$ | $4.5 \pm 4.9 \times 10^5$ | 12:1 |
| CRL1740 | prostate | $2.3 \pm 0.4 \times 10^5$ | $1.8 \pm 0.2 \times 10^5$ | 8:1 |
| CRL1611 | kidney | $3.2 \pm 1.2 \times 10^5$ | $1.8 \pm 0.3 \times 10^5$ | 6:1 |
| HTB52 | liver | $1.8 \pm 0.3 \times 10^5$ | $2.6 \pm 0.8 \times 10^5$ | 1.4:1 |
| MCF7 | breast | $7.3 \pm 2.6 \times 10^4$ | $3.6 \pm 0.9 \times 10^5$ | 5:1 |

Results represent averages ± SD for n = 3–9 separate infections.

Both the wild type strain 14028 and clone #72 were able to infect each of the human cancer cells tested in culture. In all cases, clone 72 was superinfective compared to the wild type strain.

However, human lung line HTB57 was significantly less receptive to *Salmonella typhimurium* infectivity when compared to other cancer cell lines tested. In yet another series of experiments, the human lung line HTB57 was implanted into mice. In 10 of 10 nu/nu mice implanted with $1 \times 10^7$ HTB57 cells, no tumor "takes" were observed, even after several months. Whether or not these cells were receptive to Salmonella infection when grown as tumors was not determined.

7.6. Discussion

In summary, the results demonstrate the following: a) infectivity of *S. typhimurium* is dependent upon population density of the bacteria and b) super-infective clone #72 differs from the wild type strain in its increased infectivity of melanoma cells at all bacterial population densities and especially at low population densities under aerobic growth conditions. The ability to infect at low bacterial population densities is an advantage in the use of clone #72 as a tumor-specific vector, since it would allow for a lower c.f.u. of bacteria inoculated into the cancer patient, thus reducing the risk of septic shock in the patient. Additionally, the results demonstrate methods for the isolation of super-infective, tumor-specific mutants of *S. typhimurium*. Such mutants are represented by clones #6, #70, #71 and #72 that were isolated via enrichment procedures for melanoma infectivity by the bacteria. The results further demonstrate that wild type *S. typhimurium* exhibits specificity for human cancer cells over normal human cells in culture. Further, although clone 72 was originally selected for superinfectivity toward human melanoma cell line M2, it was additionally found to be superinfective toward human colon cancer cells and transformed mouse macrophages, when compared to the wild type strain 14028 (see Table 7). The expression of super-infectivity and tumor-specificity of isolated mutant clones represent attenuation of the bacteria and present distinct advantages for the use of such Salmonella clones as tumor-specific vectors in the diagnosis and therapy of human cancer.

8. EXAMPLE

Selection For *Salmonella typhimurium* Mutants With Chemotactic Abilities Toward Melanoma Secretory Products in Vitro The melanoma cells were an artificially-produced hybrid line isolated from a polyethylene glycol induced fusion between Cloudman S91 mouse melanoma cells and peritoneal macrophages from a DBA/2J mouse. The hybrid cell line used herein was termed Cloudman S91 melanoma/macrophage hybrid #48. The hybrid cell line formed rapidly growing metastasizing tumors in DBA/2J mice, Pawelek et al., 1995, J. Invest. Dermatol. 104:605. $5 \times 10^6$ Cloudman S91 melanoma/macrophage hybrid #48 cells were cultured at 30° C. in a gassed, humidified incubator in 75cm$^2$ culture flasks in DMEM/FBS culture medium containing 10% fetal bovine serum and no antibiotics. Control flasks containing DMEM/FBS but no melanoma cells were incubated in parallel. After 72 hours, the media were removed, aseptically filtered through 0.45μ filters, and stored at 4° C.

*Salmonella typhimurium* super-infective clone #72 described above was subjected to mutagenesis with nitrosoguanidine and UV. The mutagenesis procedures produced an increase in the number of mutations in Clone #72 similar to that shown earlier when the wild type strain #14028 was mutagenized. This mutagenized population of clone 72 ("$72^{mut}$") was further used to select for mutants with enhanced chemotactic abilities toward melanoma cell secretory products, i.e., melanoma-conditioned culture media.

Procedures for loading capillary tubes with potential chemotactic attractants were modified from Adler (Adler, 1973, J. General Microbiology 74:77–91). Control and melanoma-conditioned culture media described above, were loaded into 2λ capillary tubes (MICROCAPS™, capillary tubes, Drummond Scientific Co.) as described by Adler. The capillaries were handled with forceps. One end was sealed in a flame; the capillary was then quickly passed several timers through the flame and immediately plunged open end down into a 10 ml beaker containing 1 ml control or melanoma conditioned culture medium. As the capillary cooled (about 10 minutes), liquid was drawn in about 1 cm.

*Salmonella typhimurium*, growing at 37° C. in LB were collected by centrifugation and resuspended in control DMEM/FBS culture medium containing a concentration of $10^8$ c.f.u./ml. Aliquots (200 μl, $2 \times 10^7$ c.f.u.) were pipetted into 1.5 ml microfuge tubes. Loaded capillary tubes (described above) were then inserted open end down into the Beckman microfuge tubes containing the *Salmonella typhimurium*, and the assay was begun by incubating at 37° C. After 30 to 60 minutes, the capillary tubes were removed with forceps, the sealed ends were broken off with wire cutters, and the capillaries were transferred to 15 ml conical centrifuge tubes containing 3 ml LB broth. It was important that the upper tips of capillary tubes were covered with LB broth in order to assure quantitative recovery of the bacteria via the centrifugation step described as follows. The capillaries within the centrifuge tubes were then centrifuged (1000×g for 4 minutes) to force the bacteria out of the capillaries. The bacteria were resuspended by vortexing, and aliquots were spread onto LB agar plates for quantitation, Significant increases in the number of bacteria entering the capillaries containing melanoma-conditioned media compared to control-conditioned media indicated a chemotactic response of the bacteria to melanoma-secreted products.

Aliquots of mutagenized super-infective *Salmonella typhimurium*, "$72^{mut}$", described above were placed on a rotor at 37° C., grown to an optical density of 0.4–0.6 at a wavelength of 600 nm, and subjected to the chemotaxis procedures described above. The chemotaxis cycling procedure was repeated 4 times through successive challenges with melanoma-conditioned culture medium. The population obtained after 4 cycles was designated #$72^{pop-2}$. After the 4th cycling, aliquots of the mixed populations of bacteria were frozen in glycerol. Additional aliquots of the mixed population of *Salmonella typhimurium* obtained from the fourth cycling were then compared to an uncycled mixed population of mutagenized clone 72 ("$72^{mut}$") for relative chemotactic abilities toward control and melanoma-conditioned culture medium. The results are shown in Table 8.

TABLE 8

EVIDENCE FOR POSITIVE CHEMOTACTIC RESPONSES OF *S. TYPHIMURIUM* TO CONDITIONED GROWTH MEDIUM OF CULTURED MELANOMA CELLS[+]

| | Bacteria/Capillary Tube: | | |
|---|---|---|---|
| Salmonella Strain | Control Medium | Conditioned Medium | Ratio: |
| #$72^{mut}$ (mutagenized, no cycling) | $1.2 \times 10^3 \pm 0.2$ | $4.4 \times 10^3 \pm 2.7$ | 3.7:1 |
| #$72^{pop-2}$ (mutagenized, cycled cycled 4×) | $0.5 \times 10^3 \pm 0.1$ | $1.8 \times 10^3 \pm 0.4$ | 3.6:1 |

[+]Results represent average ± S.D for quadruplicate capillary tubes.

Both populations of bacteria tested showed positive chemotactic responses to melanoma-conditioned culture medium over control-conditioned medium, displaying an approximate 4:1 preference for the melanoma-conditioned medium. Although the chemotactic response of population #$72^{pop-2}$ was not statistically significant as compared to the chemotactic response of population #$72^{mut}$ for melanoma conditioned medium, the chemotactic response of population #$72^{pop-2}$ was significantly reduced as compared to the chemotactic response of population #$72^{mut}$ for control medium. Thus, the propensity of population #$72^{pop-2}$ to enter capillary tubes containing control medium was significantly reduced. These results suggest that population #$72^{pop-2}$ is less efficient in motility generally, however, upon exposure to melanoma-conditioned medium, population #$72^{pop-2}$ showed a chemotactic response equivalent to the control population.

Whatever the mechanisms for the different chemotactic phenotypes expressed by the #$72^{mut}$ and #$72^{pop-2}$ populations of bacteria in Table 8, the results demonstrate that the phenotypes can be altered via the selection procedure of exposing bacteria to successive challenges of melanoma-conditioned media. It is likely that the mixed populations of mutagenized, chemotactically cycled bacteria isolated in these experiments contain a number of diverse mutants expressing likewise diverse phenotypes for the chemotactic response to melanoma cell-conditioned medium.

9. EXAMPLE

Isolation of Tumor-Specific Mutants of *Salmonella typhimurium* By Cycling in Vivo in Tumor-Bearing Mice Tumor cells inoculated into DBA/2J mice from Cloudman S91 melanoma/macrophage hybrid cell line #48 were used as the target tumor for the selection of attenuated, tumor-specific *Salmonella typhimurium*. Super-infective *Salmonella typhimurium* clone #72 was mutagenized with nitrosoguanidine and UVB as described in Section 7.1 producing a mutagenized population derived from clone #72. The mutagenesis procedures produced an increase in the number of mutations in clone #72 similar to that shown earlier when the wild type strain #14028 was mutagenized. Cloudman melanoma/macrophage hybrid #48 cells were inoculated (s.c.) into DBA/2J mice at a concentration of $10^6$ cells in 0.1 ml saline/inoculated site and a total of 4 sites/mouse in the shoulder and flank regions. After 8–10 days, palpable tumors developed, and the mice were inoculated (i.p.) with the mutagenized Salmonella population derived from super-infective clone #72. After 2 hours of infection, the mice were sacrificed, the tumors removed, weighed, and homogenized in a teflon homogenizer in 5 vol (vol/wt) LB broth. An aliquot of the homogenate was then diluted about 1:4 in LB broth, placed on a rotator at 37° C., and incubated through 1–2 population doublings, should be monitored at $OD^{600}$, in order to ensure the recovery of viable bacteria for successive inoculations into tumor-bearing mice. The procedure was repeated through 4 cycles of infection into mice, followed by recovery from tumors. At the beginning of each cycle, the number of bacteria inoculated and the time of infection was reduced from the previous cycle in order to increase the stringency of selection for tumor-specific mutants. The resultant population recovered after 4 cycles was designated #$72^{pop-1}$. The results of this procedure are detailed in Table 9 below.

TABLE 9

SELECTION FOR MELANOMA-SPECIFIC *SALMONELLA TYPHIMURIUM* IN TUMOR-BEARING MICE

| Infection Cycle | Total # Bacteria Inoculated/mouse | Infection Time | Total # Bacteria Recovered in Tumors* |
|---|---|---|---|
| 1 | $1 \times 10^{10}$ | 120 min | $2.1 \times 10^7$ |
| 2 | $1 \times 10^9$ | 80 min | $1.6 \times 10^6$ |
| 3 | $6 \times 10^8$ | 60 min | $1.7 \times 10^6$ |
| 4 | $2 \times 10^6$ | 40 min | $1.4 \times 10^5$ |

*Infecting Salmonella were pooled from 4–8 separate tumors for each cycle

These results demonstrate that infecting bacteria can be recovered from tumors in vivo. These results also demonstrate that in vivo cycling results in an enriched population since fewer bacteria were isolated than were inoculated.

10. EXAMPLE

Proliferation of *Salmonella typhimurium* Within Melanoma Cells

Proliferation of a gene-delivering vector within target tissue can both amplify the gene within the target tissue as well as allow one to reduce the titer of inoculated vector, thus reducing the risk of septic shock in the host. The following examples demonstrate that *Salmonella typhimurium* proliferates in melanoma cells.

Proliferation Within Cultured Human M2 Melanoma Cells

It was found that *Salmonella typhimurium* proliferated within human M2 melanoma cells in culture with doubling times of about 30 to 60 minutes as illustrated below. Wild type Salmonella strain #14028 and super-infective clone #72 were separately introduced into the culture media of human M2 melanoma cells $2\times10^5$ melanoma cells/25 cm$^2$ tissue culture flask at $10^6$ bacterial c.f.u./ml culture medium. After 1 hour, gentamicin (20 μg/ml) was added to kill external, but not internalized bacteria, and melanoma cells were harvested and assayed for the number of internalized bacteria at the time points indicated. The results are presented in Table 10.

TABLE 10

PROLIFERATION OF *SALMONELLA TYPHIMURIUM* WILD TYPE STRAIN #14028 AND CLONE #72 WITHIN CULTURED HUMAN M2 MELANOMA CELLS[+]

| Salmonella Strain | Time (h) | Salmonella/ $10^6$ Melanoma Cells | Fold Increase |
|---|---|---|---|
| #14028 wild type | 1 | $6.8 \times 10^5$ | — |
|  | 2 | $1.8 \times 10^6$ | 2.6× |
|  | 4 | $1.8 \times 10^7$ | 26× |
|  | 6 | $5.4 \times 10^7$ | 79× |
| Clone #72 | 1 | $5.8 \times 10^6$ | — |
|  | 2 | $8.0 \times 10^6$ | 1.4× |
|  | 4 | $3.2 \times 10^7$ | 5.5× |
|  | 6 | $1.4 \times 10^8$ | 24× |

[+]The numbers represent averages for duplicate and triplicate determinations, with the variation between replicates < ± 25%.

10.2. Proliferation Within Melanoma Tumors Grown in Mice

DBA/2J mice were inoculated s.c. in four areas (left and right shoulders and flanks) with $10^6$ Cloudman S91 melanoma/macrophage hybrid #48 cells. After the appearance of palpable tumors (8–10 days) the mice were further inoculated (i.p.) with $2\times10^8$ *Salmonella typhimurium*. The Salmonella strains tested were wild type #14028 and super-infective clone #72. At 4 hours and 21 hours post-inoculation with bacteria, mice were bled orbitally, and then euthanized by anesthesia with metofane. Tumors and livers were removed aseptically, rinsed with sterile NaCl (0.9%), weighed, and homogenized in LB broth at a ratio of 5:1 (vol:tumor wt). Bacteria were quantitated by plating the homogenates onto LB plates, incubating overnight at 37° C., and counting bacterial colonies. Numbers represent averages± S.D. The results for the 4 hour and 21 hour incubations of the bacteria in mice are detailed in Tables 11(A) and 11(B).

TABLE 11

A. DISTRIBUTION OF *SALMONELLA TYPHIMURIUM* 4 HOURS FOLLOWING INOCULATION (I.P.) INTO CLOUDMAN S91 MELANOMA-BEARING DBA/2J MICE

| Salmonella Strain | Salmonella/ ml Blood | Salmonella/ gm tumor (wet wt) | Salmonella/ gm liver (wet wt) | Tumor/ Liver |
|---|---|---|---|---|
| wild type | $6 \times 10^6$ | $8.9 \pm 2.5 \times 10^4$ (n = 4) | $3.6 \times 10^6$ | 1:4 |
| clone 72 | $2 \times 10^6$ | $3.5 \pm 3.3 \times 10^4$ (n = 4) | $2.4 \times 10^5$ | 1:7 |

B. DISTRIBUTION OF *SALMONELLA TYPHIMURIUM* 21 HOURS FOLLOWING INOCULATION (I.P.) INTO CLOUDMAN S91 MELANOMA-BEARING DBA/2J MICE

| Salmonella Strain | Salmonella/ ml Blood | Salmonella/ gm tumor (wet wt) | Salmonella/ gm liver (wet wt) | Tumor/ Liver |
|---|---|---|---|---|
| wild type | $1.0 \times 10^4$ | $1.3 \pm 0.8 \times 10^9$ (n = 4) | $4.4 \times 10^6$ | 300:1 |
| clone 72 | $6.7 \times 10^3$ | $2.1 \pm 2.7 \times 10^9$ (n = 4) | $5.2 \times 10^5$ | 4000:1 |

At 4 hours post-inoculation of Salmonella, there were fewer bacteria in the tumors than in the blood stream and the liver for both wild type clone 14028 and clone 72. However, by 21 hours, Salmonella were found in great abundance in the tumors so that the ratio of bacteria/g tissue in tumors was 4,000:1 over that in the liver for super-infective mutant clone 72. After 21 hours post-inoculation of bacteria, the number of Salmonella in the tumors was similar for both the wild type Salmonella strain and clone 72, and was far greater than the total number of Salmonella originally inoculated, indicating that both wild-type and clone 72 strains of bacteria proliferated within the tumors. Thus, the ability of *Salmonella typhimurium* to infect melanoma cells and proliferate within them was expressed both in cell culture as seen in Table 10 and in tumors growing in mice as seen in Tables 11A and 11B.

The wild-type strain 14028 showed higher infectivity in liver than did clone 72. The higher infectivity of liver by the wild-type Salmonella was consistent with the observed greater lethality of the wild type stain toward DEA/2J mice than that produced by clone 72 at high bacterial inocula ($>10^9$ c.f.u./mouse, data not shown). Similar results were observed with C57BL\6J mice bearing B16F10 melanomas as seen in Table 18, Section 15.2. Together, these results demonstrate that selection for strains of bacteria or other parasites with enhanced tumor specificity in vitro yields mutant strains with attenuated host toxicity in vivo.

10.3. Distribution of *Salmonella Typhimurium* in Tumor-Bearing Mice

The following experiments demonstrate that Salmonella can localize to and proliferate within a tumor of an animal bearing either multiply-implanted subcutaneous melanoma tumors or naturally occurring metastases.

10.3.1. Distribution of Salmonella Following Direct Inoculation Into Cloudman S91 Melanoma Tumors DBA/2J mice were inoculated s.c. in four areas (left and right shoulders and flanks) with $10^6$ Cloudman S91 melanoma/macrophage hybrid site. Palpable tumors appeared 8–10 days post-inoculation, representative animals were selected, and 2 of the 4 tumors (right shoulder and left flank) were directly inoculated with *Salmonella typhimurium* super-infective clone #72 at c.f.u.'s of $7\times10^4$ or $7\times10^6$ bacteria/tumor. At 21 hours post-inoculation, mice were euthanized with metofane. Tumors and livers were removed, aseptically, rinsed with sterile NaCl (0.9%), weighed, and homogenized with NaCl at a ratio of 5:1 (vol:tumor wt). Bacteria were quantitated by plating the homogenates onto LB plates, incubating overnight at 37° C., and counting bacterial colonies. The results are shown in Table 12.

TABLE 12

DISTRIBUTION OF *SALMONELLA TYPHIMURIUM* CLONE 72 IN CLOUDMAN S91 MELANOMA-BEARING MICE 21 HOURS FOLLOWING DIRECT INOCULATIONS INTO TUMORS

| Inoculum/ tumor | Salmonella/ g tumor (wet wt) | Salmonella/ g liver (wet wt) | Tumor/Liver |
|---|---|---|---|
| $7.2 \times 10^4$ | | | |
| Tumor 1* | $1 \times 10^9$ | $3.0 \times 10^5$ | 3,300:1 |
| Tumor 2 | $3 \times 10^7$ | | 100:1 |
| Tumor 3 | $1 \times 10^8$ | | 330:1 |
| $7.2 \times 10^6$ | | | |
| Tumor 1* | $4 \times 10^9$ | $5.0 \times 10^6$ | 800:1 |
| Tumor 2 | $3 \times 10^9$ | | 600:1 |
| Tumor 3 | $3 \times 10^7$ | | 6:1 |

*inoculated tumor

In summary, two days post-inoculation of super-infective *Salmonella typhimurium* clone #72 directly into specificized tumors, the Salmonella could be found in distal, non-inoculated tumors. The amounts of Salmonella found in the tumors far exceeded the amounts of Salmonella inoculated into the mice, proving that the Salmonella proliferated within the tumors. The results demonstrate that *Salmonella typhimurium* can proliferate within a tumor, exit that tumor via the circulatory system, travel to a distant tumor, and proliferate within that distant tumor.

10.3.2. Distribution of Salmonella Into Cloudman S91 Melanoma Metastases

This experiment shows that the bacteria should be able to target naturally-occurring metastases of solid tumors.

$1\times10^5$ Cloudman S91 melanoma cells were inoculated s.c. in the tail of a DBA/2J mouse. After approximately four weeks, a soft tissue metastasis (~0.5 g) developed with no visible evidence of a primary tumor in the tail. *S. typhimurium* clone 72 at $2\times10^5$ c.f.u. was inoculated i.p. The mouse was sacrificed 48 hours post-inoculation, and the liver and tumor were removed, homogenized in Luria broth, and quantitated for *S. typhimurium* by serial dilutions on LB agar plates.

The results shown in Table 12(A) demonstrate that *Salmonella typhimurium* clone 72 can target and proliferate within a metastatic tumor.

TABLE 12(A)

DISTRIBUTION OF *SALMONELLA TYPHIMURIUM* CLONE 72 IN A DBA/SJ MOUSE WITH A SOFT-TISSUE MELANOMA METASTASIS*

| Tissue | Salmonella/g tissue | Tumor/Liver |
|---|---|---|
| Liver | $3.1 \times 10^6$ | — |
| Tumor | $3.2 \times 10^9$ | 1000:1 |

*Results represent determinations from a single animal.

11. EXAMPLE

Antibiotic Sensitivity of Wild Type *Salmonella Typhimurium* Strain 14028 and Super-Infective Mutant Clone 72

11.1. Sensitivity Tested in Vitro

Wild type *Salmonella typhimurium* strain 14028 and super-infective mutant clone 72 were tested for antibiotic susceptibility and were each found to be sensitive to 12 different antibiotics currently used in treating bacterial infections. The bacteria were tested according to the standard protocol to determine antibiotic sensitivity as seen in clinical laboratories, so that a patient is not given an antibiotic to which the microorganism is resistant. The bacteria were tested for antibiotic susceptibility by subjecting them to the DISC DIFFUSION SUSCEPTIBILITY TECHNIQUE KIT™ antibiotic sensitivity assay kit (Remel Corp., Lenexa, Ks.). The data are presented in Table 13.

TABLE 13

| ANTIBIOTIC SENSITIVITY | | |
|---|---|---|
| | Wild Type: | Clone 72: |
| Ampicillin | S | S |
| Cefoperazone | S | S |
| Ceftazidime | S | S |
| Cefuroxime | S | S |
| Gentamicin | S | S |
| Mezlocillin | S | S |
| Cefazolin | S | S |
| Ciprofloxacin | S | S |
| Unasyn | S | S |
| Ceftriaxone | S | S |
| TMP/SMX | S | S |

11.2. Sensitivity Tested in Vivo

Susceptibility of *Salmonella typhimurium* cloned 72 to antibiotics was further tested by injecting mice i.p. with bacteria, treating half of the mice with the antibiotic enrofloxacin, and observing the effects of enrofloxacin, an active analog of ciprofloxacin, on the survival of the mice.

Six week old C57B6 female mice were inoculated i.p. with $10^5$ cfu *Salmonella typhimurium* clone 72. After four days following inoculation with bacteria, three of the mice were further inoculated i.p. with 100 μg/0.1 ml BAYTRIL™ (enrofloxacin), and their drinking water was supplemented with 25 μg/ml BAYTRIL™. After 4 days, all the mice were given fresh drinking water without BAYTRIL™. After a total of 21 days, all surviving mice were euthanized and the experiment was terminated. The results are shown below in Table 13(A).

TABLE 13(A)

SURVIVAL OF C57B6 MICE INJECTED WITH *SALMONELLA TYPHIMURIUM* CLONE 72 ± BAYTRIL ® (enrofloxacin) IN DRINKING H$_2$O

| Conditions | Avg. time of Death ± S.D. |
|---|---|
| no antibiotic | 9.3 ± 5 days |
| enrofloxacin (days 4–10 post-inoculum) | >21 days |

Mice receiving bacteria only and no antibiotic died after an average of 9 days following inoculation. Mice receiving bacteria followed by antibiotic treatment survived at least 21 days and showed no symptoms of Salmonella toxicity when the experiment was terminated. Thus, the results clearly demonstrate that mice can be rescued from Salmonella-mediated death by treatment with the antibiotic enrofloxacin. These results are consistent with those presented in Table 13 demonstrating antibiotic sensitivity of *Salmonella typhimurium* strains 14028 and clone 72 by the DISC DIFFUSION SUSCEPTIBILITY TECHNIQUE KIT™ antibiotic sensitivity assay kit.

The results further underscore the advantage of using antibiotic-sensitive bacteria as vectors in human tumor therapy, since the bacteria can be eliminated by introduction of antibiotics when desired.

12. EXAMPLE

Enhanced Expression of Bacterial Promoters in Melanoma Cells

In a preferred embodiment of the present invention an isolated super-infective vector, such as *Salmonella typhimurium* clone 72$^{5-3-2}$ which carries the HSV TK gene, the gene is specifically induced in cancerous target cells as opposed to normal cells in the host body. It has been shown that there is a higher relative induction of several Salmonella promoter genes, including pagB and pagC, (Miller et al., 1989, Proc. Natl. Acad. Sci. USA 86:5054–5058; Miller et al., 1992, Infect. Immun. 60:3763–3770; Alpuche Aranda et al., 1992, Proc. Natl. Acad. Sci. USA 89:10079–10083) when the bacteria invade macrophages as opposed to epithelial cells. In order to test whether these promoters are also activated when Salmonella invade melanoma cells, we used Salmonella-bearing promoter constructs fused to the β-galactosidase reporter gene.

Human melanoma M2 cells, (Cunningham et al, 1992, Science, 255:325–327) human epithelial 1790 cells and mouse macrophage cell line J774 cells (American Type Culture Collection) were seeded at a density of 1×10$^6$ host cells in 25 cm$^2$ Corning tissue culture flasks. The cells were infected with 5×10$^7$ *Salmonella typhimurium* #14028/ml DMEM culture medium for 1 hour, washed with fresh medium, and further cultured for 6 hours with 50 μg/ml gentamicin added to the culture medium in order to kill the external but not the internalized Salmonella. The melanoma cells were then harvested by scraping them from the substratum in isotonic 1 mM EDTA solution. The cells were pelleted, resuspended in PBS and an aliquot was removed for quantitation of the bacteria found within the melanoma cells. The remainder of the melanoma cells were assayed for β-galactosidase activity.

Three *Salmonella typhimurium* clones were used: i) strain 14028 in which β-galactosidase was constitutively expressed; ii) strain 14028 in which β-galactosidase was expressed through activation of the pagB promoter; iii) strain 14028 in which β-galactosidase was expressed through activation of the pagC promoter. Thus, through measurements of β-galactosidase activity, analyses of bacterial pagB and pagC promoter induction in melanoma cells were carried out. The results are detailed in Table 14.

TABLE 14

ENHANCED EXPRESSION OF BACTERIAL PROMOTERS PAGB AND PAGC IN CULTURED HUMAN MELANOMA M2 CELLS[+]

| | Promoter-Induced Activity: Constitute Activity | |
|---|---|---|
| Cell Line | pagB | pagC |
| human epithelial | 1.3:1 | 7.2:1 |
| mouse transformed macrophage | 2.9:1 | 17:1 |
| human melanoma | 3.8:1 | 31:1 |

[+]relative activation of pagB and pagC was assessed through expression of promoter-inducible β-galactosidase activity.

Both the pagB and pagC Salmonella promoters were induced in human melanoma cells. Levels of induction in melanoma cells were greater than seen in either the epithelial or macrophage cell lines. These data demonstrate that the pagB or pagC promoter could be used to express genes, such as HSV TK or *E. coli* cytosine deaminase, in a melanoma cell-specific manner.

13. EXAMPLE

Cloning and Expression of Prodrug Converting Enzymes

The following sections demonstrate useful systems for expression of prodrug-converting enzymes useful for the methods and compositions of the present invention.

13.1. Cloning and Expression of *Herpes Simplex* Virus Thymidine Kinase in *Salmonella typhimurium*

Herpes simplex thymidine kinase (HSV TK) is known to be an effective pro-drug converting enzyme in the inhibition of melanoma tumor growth (Bonnekoh et al., 1995, J. Invest. Derm. 104:313–317). Accordingly, procedures were carried out to insert an HSV TK gene with the β-lactamase signal sequence into both *Salmonella typhimurium* wild type strain 14028 and super-infective tumor-specific mutant clone 72 which is derived from the wild type strain.

*Herpes Simplex* Thymidine Kinase Cloning By PCR

Plasmid DNA of the vector pHETK2 (Garapin et al., 1981, Proc. Natl. Acad. Sci. USA 78:815–819) was prepared by alkaline lysis, phenol/chloroform extraction and ethanol precipitation. PCR primers based on the complete sequence for the *Herpes simplex* thymidine kinase (McKnight, 1980, Nuc. A. Res. 8:5949–5964) were: forward 5'-GATCATGCATGGCTTCGTACCCCGGCC-3' (SEQ ID NO:1) and reverse 5'-CTAGATGCATCAGTGGCTAT-GGCAGGGC-3', (SEQ ID NO:2) which corresponds to bases 310–328 (forward) and 1684–1701 (reverse) of the published sequence, with an added sequence of GATCAT-GCAT (portion of SEQ ID NO:1) or CTAGATGCAT (portion of SEQ ID NO:2) (NsiI site and spacer) at the 5' end of each primer. Each reaction mixture contained 50 ng DNA template, 10 pmoles of each primer, 100 mM deoxynucleotide triphosphates, 1.5 mM Mg$^{++}$ and 0.5 unit's. Taq polymerase (Perkin Elmer Cetus, Norwalk, Conn.). Amplification was performed by 35 cycles of 94° C. for 1 minute; 50° C. for 15 seconds; 55° C. for 1 minute; and 72° C. for 2 minutes. The amplified DNA was purified and was cloned into either pBluescript II KS+ and sequenced with T3 and T7 primers to confirm the correct DNA had been cloned or was cloned into p279 cut with Pst1 which provides the β-lactamase signal sequence (Talmadge et al., 1980, Proc. Natl. Acad. Sci. USA 77:3369–3373). Transformants were screened using a probe generated from the original template by random priming (Boehringer Mannheim, Indianapolis, Ind.) using [α-$^{32}$P]dCTP. Positive clones were further screened by immunoblot.

SDS-PAGE and Immunoblot

Sodium dodecyl sulfate-polyacrylamide gel electrophoresis (SDS-PAGE) was performed on bacterial lysates according to Weber and Osbom, 1975, Proteins and sodium dodecyl sulfate: Molecular mass determination on polyacrylamide gels and related procedures. In: H. Neurath and R. Hill (eds) The Proteins, Third Edition, vol. 1, Academic Press, New York pp. 179–223. Immunoblots were performed according to Towbin et al., 1979, Proc. Natl. Acad. Sci. USA 76:4350–4354. Primary anti-TK antibodies were generally used at a 1:1000 dilution. Secondary antimouse antibodies were alkaline phosphatase-conjugates (Promega, Madison, Wis.) used at a 1:7,500 dilution, followed by nitroblue tetrazolium (NBT) and 5-bromo-4-chloro-indolyl phosphate (BCIP) colorimetric detection (Promega).

Thymidine Kinase Assay

Bacterial lysates were prepared by pelleting 1 ml of log-phase bacterial culture for 30 seconds at 12,000×g in a microfuge centrifuge. The pellet and supernatant were retained separately and the supernatant was further cleared by centrifugation for 10 min at 12,000×g. The pellet was further treated by resuspension in 100 μl of phosphate buffered saline containing 1 mg/ml lysozyme and 1% (v/v) Triton X-100 and subjected to three cycles of rapid freezing and thawing. The resulting material was clarified by centrifugation at 12,000×g for 2 minutes. Thymidine kinase activity was assayed using a modified version of the assay described by Summers and Summers, 1977, J. Virol. 24:314–318. The reaction mix was incubated at 37° C. for 1 hour and then bound to DE81 paper (Whatman), washed, and the associated radioactivity determined in a gamma counter.

Salmonella Transformation

Transformation of Salmonella strains was performed by electroporation as described by O'Callaghan and Charbit, 1990, Mol. Gen. Genet. 223:156–158. Plasmids transfected into Salmonella included pHETK2 (Garapin et al., 1981, Proc. Natl. Acad. Sci. USA 78:815–819) p279 (Talmadge et al., 1980, Proc. Natl. Acad. Sci. USA 77:3369–3373) and two independent isolates of β-lactamase fusions, p5-3 and p21A-2 (See FIG. 4-C for a diagram of p5-3 and p21A-2 where these plasmids are designated "pTK Sec 1". *Salmonella typhimurium* strains transfected were the wild type 14028 and the super-infective clone 72.

Two independent β-lactamase-TK gene fusion constructs were isolated and expressed in *Salmonella typhimurium* 14028 wild type and clone 72. An immunoblot analysis and corresponding enzyme activity assay are presented in FIGS. 4A and 4B. All three TK-containing vectors, the cytoplasmically expressed pHETK2 and the β-lactamase fusions p5-3 and p21A-2, were detectable by immunoblot and enzyme assay. Relatively little enzyme activity was recovered from the culture supernatants. Since the immunoblot analysis shows processing of the signal sequence, secretion into the periplasmic space of the *Salmonella typhimurium* is expected.

13.2. Systems For Expression of *Herpes Simplex* Thymidine Kinase Using Various Promoters and Secretion Signals A number of constructs were made to express TK using other promoters and other secretion signals.

13.2.1. Expression as a Staphylococcus Protein a Fusion Under the LacI Promoter

*Herpes simplex* thymidine kinase was amplified by PCR as described in Section 13.1 above and cloned into the PstI site of pBluescript. This TK clone was subcloned from bluescript to the BamHI and HindIII cite of the secretion vector pEZZ18 (Promega, Madison, Wis.; Nilsson and Abrahamsen, 1990, Methods in Enzymology 185:144–161). This resulted in an in-frame fusion with Staphylococcus protein A under the lacI promoter. This plasmid was designated pTK-Sec2 and is diagramed in FIG. 4-C. Plasmid pTK-Sec2 expresses thymindine kinase as determined by an immunoblot.

13.2.2. Cloning of the Serratia Marcesens Chitinase Signal Sequence and Promoter The promoter and signal sequence of Serratia marcesens chitinase I (Jones et al., 1986, EMBO J. 5:467–473) was cloned by PCR. The forward and reverse primers had the following sequence: CTAGACTAGTTTGTCAATAATGA-CAACACCC (forward) (SEQ ID NO:3) and GATCG-GATCCTTGCCCGGCGCGGCGGCCTG (reverse) (SEQ ID NO:4) which contain SpeI and BamHI sites, respectively. The resulting product was cloned into pSP72 and confirmed by DNA sequencing. This plasmid was designated pSP-CHT and is also diagramed in FIG. 4-C.

13.2.3. Expression as a Chinase Signal Sequence Fusion Under the Control of the Chitinase Promoter

*Herpes simplex* thymidine kinase in pBluescript was subcloned into the pSP-CHT vector using BamHI and HindIII. This results in an in-frame fusion with the chitinase signal sequence under the chitinase promoter. This plasmid was designated pTK-Sec3 and is also diagramed in FIG. 4-C. Plasmid pTK-Sec3 expresses thymindine kinase as determined by an immunoblot.

13.3. Expression of P450 Oxidoreductase prodrug Converting Enzyme in Bacteria Using an Exogenously Inducible Promoter The sulA promoter element (GENBANK #V00358; Cole 1983) was cloned from *E. coli* genomic DNA by PCR using forward (CTAGAAGCTTATAAGGGTTGATCTTTGTTGTC) (SEQ ID NO:5) and reverse (GTACGATATCCAG-AACGATGTGCATAGCCTG) (SEQ ID NO:6) primers which incorporate the HindIII and EcoRV restriction sites respectively. The PCR conditions were 35 cycles of 95° C., 1 minute; 55° C. 1 minute; and 72° C. for 1 minute. The product was cloned into pSP72 and sequenced with the T7 primer to confirm that the correct DNA had been obtained. The cloned DNA fragment was 100% identical to the published sequence.

The NADPH-dependent cytochrome p450 oxidoreductase (p450 OR) CDNA clone in the EcoRI site of pBluescript that lacks the first initiating ATG (deletion of the first 11 nucleotides) of the cDNA described by Yamano et al., 1989, Molecular Pharmacol. 35:83–88, was fused with the sulA promoter and initiating sequence by cloning the sulA promoter obtained as described above into the HindIII and EcoRV site of the p450 oxidoreductase gene. The resulting fusion consists of the sulA promoter, including the sulA ATG (methionine) and subsequent 9 amino acids (YTSGYAHRS) (SEQ ID NO:7) as well as six amino acids which follow introduced from the DNA polylinker and PCR primers (SGYRIP) (SEQ ID NO:8) followed with the second amino acid of p450 OR, which is G. This construct, pSP-SAD4-5 is diagramed in FIG. 4-D.

13.4. Effect of Expression of P450 Oxidoreductase Conversion of Prodrug On Bacterial Growth It has been previously shown (Shiba et al., 1959, Nature 183:1056–1057) that some strains of bacteria are sensitive to low levels of mitomycin. Therefore, to compare the sensitivity of a specific bacterial strain with and without the sulA::p450 OR expression plasmid the following experiment was performed. If the construct is functional, the presence of the p450 OR gene is expected to result in increased activation of mitomycin resulting in decreased growth of the bacteria. The sulA::p450 OR expression plasmid used in this experiment is similar to pSP-SAD4-5 (Section 13.3) except that it is in a pbluescript (pBS) backbone and has the β-galactosidase transcription unit. This construct is also diagramed in FIG. 4-D. The pBS plasmid, with and without the expression construct, was transfected into Escherichia coli DH5α by electroporation and clones containing the correct plasmids were obtained and confirmed by plasmid isolation and DNA restriction analysis. For each of the two plasmid-bearing strains, a fresh, 4 hr (late log) culture was diluted 1:100 into LB with 100 µg/ml ampicillin to select for the presence of the plasmid and grown at 37° C. at 250 rpms. Mitomycin C was added to the cultures in amounts of 0.0, 0.1 and 0.5 µg per ml.

Optical density was determined at 600 nm using a Perkin Elmer double beam spectrophotometer at 2 and 18 hour time points. The results are presented in Table 14(A).

TABLE 14A

GROWTH OF BACTERIAL CULTURES IN THE PRESENCE OF MITOMYCIN C

| Plasmid | $OD_{600}$ t = 2 hours post drug Amount of Mitomycin C (µg/ml) added | | |
|---|---|---|---|
| | 0 | 0.1 | 0.5 |
| pBS | 0.052 | 0.050 | 0.053 |
| sulA::p450 OR | 0.037 | 0.030 | 0.024 |

| Plasmid | $OD_{600}$ t = 18 hours post drug Mitomycin C (µg/ml) added | | |
|---|---|---|---|
| | 0 | 0.1 | 0.5 |
| pBS | 2.33 | 2.23 | 1.93 |
| sulA::p450 OR | 2.26 | 0.34 | 0.071 |

Comparison of the growth of the E. coli strain DH5α containing pBS and sulA::p450 OR in the absence of drug at the 2 and 18 hour time points shows that the presence of the construct partially inhibits the rate of growth but does not inhibit attaining a high final OD at 18 hours. These data also show that bacteria carrying the pBS backbone plasmid alone are only partially inhibited at the higher mitomycin concentration. However, those carrying the sulA::p450 construct show significant inhibition at both early and late time points at both mitomycin concentrations. These data indicate a strong dose response to mitomycin conferred by the presence of the sulA::p450 construct.

13.5. Expression of Cytosine Deaminase in *Salmonella typhimurium*

*E. coli* cytosine deaminase (CD) has been shown to be an effective prodrug-converting enzyme useful for gene therapy (Hirschowitz et al., 1995, Human Gene Therapy 6:1055–1063; Huber et al., 1993, Cancer Res. 53:4619–4626; Huber et al., 1994, Proc. Natl. Acad. Sci. USA 91:8302–8306; Moolten, 1994, Cancer Gene Ther. 1:279–287; Mullen et al., 1992, Proc. Natl. Acad. Sci. USA 89:33–37; Mullen et al., 1994, Cancer Res. 54:1503–1506; Trihn et al., 1995, Cancer Res. 55:4808–4812). CD functions by converting the non-toxic 5-fluorocytosine (5-FC) to the toxic compound 5-fluorouracil (5-FU). Salmonella possess an endogenous CD, however, its expression is catabolite repressed (West and O'Donovan, 1982, J. Bacteriol. 149:1171–1174). A CD expression vector using the constitutively active β-lactamase promoter to ensure expression of CD within tumors was cloned as described below.

Cloning and Expression of CD

PCR primers based on the complete sequence for *E. coli* cytosine deaminase (Huber et al., 1993, Cancer Res. 53:4619–4629) were forward: 5'-GATCATGCATGTGGAGGCTAACAGT-3' (SEQ ID NO:9) and reverse: 5'-CTAGATGCATCAGAC-AGCCGCTGCGAAGGC-3' (SEQ ID NO:10), corresponding to the published sequence, with the added sequence GATCATGCAT (portion of SEQ ID NO:9) or CTAGATG-CAT (portion of SEQ ID NO:10) which is a NsiI site and spacer at the 5' end of each primer. Each 25 µl reaction mixture contained 50 ng DNA template, 10 pmoles of each primer, 100 mM deoxynucleotide triphosphates, 1.5 mM Mg and 0.5 units Taq polymerase (Perkin Elmer Cetus, Norwalk, Conn.). Amplification was performed by 35 cycles of 94° C. for 1 minute; 50° C. for 15 seconds; 55° C. for 1 minute; and 72° C. for 2 minutes. The amplified DNA was purified on an agarose gel and the band of correct size was cloned into 1) pBluescript II KS+ and sequenced with T3 and T7 primers to confirm the correct DNA had been cloned and 2) p279 cut with PstI which provides the β-lactamase signal sequence and the constitutive β-lactamase promoter. This second construct was designated pCD-Sec1 and is diagramed in FIG. 4-E. Transformants were screened using a [α-$^{32}$P] dCTP-labeled oligonucleotide probe. Positive clones were further screened by immunoblot using anti-CD antibodies described below.

Primary Antibodies to Cytosine Deaminase

CD was subcloned from pBluescript into PGEX I and expressed using IPTG. The expressed protein was found to be insoluble and present in inclusion bodies. CD-glutathione-S-transferase (GST) fusion protein was purified from inclusion bodies by washing in 0.1% w/v Triton X-100, repelleted and resuspended in SDS-PAGE sample buffer. The material was separated on a 3 mm preparative 10% polyacrylamide gel and excised after visualization with 3M potassium acetate at 4° C. The purifed bands were homogenized and injected i.p. into DBA2J mice with Freund's complete (day 0) and incomplete (day 14) adjuvant. After 6 weeks the mice were bled and the ability of the serum antibodies to bind to cloned CD confirmed by Immunoblot.

SDS-PAGE and Immunoblot

SDS-polyacrylamide gel electrophoresis (SDS-PAGE) was performed on bacterial lysates according to Weber and Osbom, 1975, Proteins and sodium dodecyl sulfate: Molecular mass determination on polyacrylamide gels and related procedures. In:H. Neurath and R. Hill (eds) The Proteins, Third Ed., Vol. I, Academic Press, New York, pp. 179–223. Immunoblots were performed according to Towbin et al., 1979, Proc. Natl. Acad. Sci. USA 76:4350–4354. Primary anti-CD antibodies described above were generally used at a 1:500 dilution. Secondary anti-mouse antibodies were alkaline phosphatase-conjugates (Promega, Madison, Wis.) used at a 1:7,500 dilution, followed by nitroblue tetrazolium (NBT) and 5-bromo-4-chloro-indolyl phosphate (BCIP) calorimetric detection (Promega, Madison, Wis.).

CD Enzyme Assay

Bacterial lysates were prepared by pelleting 50 ml of overnight bacterial culture at 3000×g for 10 minutes and resuspending them in 2.5 ml of PBS. The cells were sonicated and the debris removed by pelleting in a microfuge at 12,00×g for 10 minutes. The enzyme assay performed was modified from Mullen et al., 1992, Proc. Natl. Acad. Sci. USA:89:33–37. 10 $\mu$l of cell extract was incubated with 1 $\mu$l [$H^3$]-5FC (1 $\mu$CI/$\mu$l) a 37° C. 1 $\mu$l was spotted on a Kodak 13254 microcrystalline nitrocellulose TLC plate, Eastman Kodak, Rochester N.Y., and separated using 95:5 Butanol-:water with unlabeled 5FC and 5FU markers. The plates were cut based upon separation of the marker lanes and quantified using a liquid scintillation counter.

Salmonella Transformation

Transformation of Salmonella strains was performed by electroporation as described by O'Callaghan and Charbit, 1990, Mol. Gen. Genet. 223:156–158. Plasmids transfected into Salmonella were p279 and pCD-Sec1. *Salmonella typhimurium* strains transfected were strains YS721, YS7211, YS7212 and YS7213 which are described infra in Section 18. *E. coli* strains transfected were strains DH5α and KL498 (Δcod).

Biodistribution of Salmonella Carrying the CD Expression Construct

*Salmonella typhimurium* clone YS7212 carrying the CD expression construct pCD-Sec1 was grown in LB media to an $OD_{600}$ of 0.8. An aliquot of $1.0 \times 10^6$ bacteria were inoculated i.p. into C57/B6 mice which had been implanted with $2 \times 10^5$ B16 melanoma cells 16 days prior to the bacterial infection. At two days post bacterial infection, mice were sacrificed and tumors and livers assayed for the presence of the bacteria by homogenization and plating of serial dilutions.

The expressed protein product of pCD-Sec1 bound to the anti-CD anti-serum by immunoblot analysis. When this clone was transferred to the *E. coli* strain KL498 which lacks CD, it was found to confer a high degree of enzyme expression as determined by the conversion of 5FC to 5FU, as shown in FIG. 4-F. FIG. 4-F also demonstrates that the cloned CD-expression plasmid gives higher levels of conversion than the *E. coli* strain MG1655 which expresses the wild type haploid cod gene which encodes for endogenous CD.

14. EXAMPLE

Proliferation of *Salmonella typhimurium* Clone #72$^{5-3-2}$ in Melanoma Tumors in Mice In a similar set of experiments as in Section 10.2, DBA/2J mice (approximately 10 weeks) were inoculated (s.c.) with $3 \times 10^5$ Cloudman S91 melanoma/macrophage hybrid #48 cells in each of 4 sites over the right and left shoulders and flanks. Tumors were palpable 10–12 days post inoculation of tumor cells from tissue culture into mice. After two weeks post-inoculation of tumor cells (s.c.), tumor-bearing mice were additionally inoculated (i.p.) with $2 \times 10^5$ c.f.u. of *S. typhimurium* clone 72 containing the HSV TK gene with the β-lactamase signal sequence which is designated 72$^{5-3-2}$. After 2 and 10 days of bacterial infection without antibiotic treatment, representative tumor-bearing animals were sacrificed and their tumors and livers were homogenized and quantitated for c.f.u. of Salmonella per gram of tissue. In addition, individual clones of bacteria were isolated from the liver and tumor homogenates 10 days post-infection and tested for the genetic markers xyl$^{neg}$ (inability to metabolize xylose, characteristic of clone #72) and tet$^{res}$ (resistance to the antibiotic tetracycline). The genotype of the inoculated *Salmonella typhimurium* clone #72$^{5-3-2}$ was xyl$^{neg}$ and tet$^{res}$. The tet$^{res}$ clones of Salmonella were assumed to carry the HSV TK gene, since the HSV TK gene was carried on a plasmid that carried the tet$^{res}$ marker.

The results are presented in Tables 15 and 16. After 2 days of infection, the tumors contained an average of $1.5 \times 10^9$ Salmonella/g tumor and $2.0 \times 10^5$ Salmonella/g liver, with an average ratio of tumor:liver of about 7,500:1.

TABLE 15

DISTRIBUTION OF *SALMONELLA TYPHIMURIUM* 2 DAYS FOLLOWING INOCULATION (I.P.) INTO CLOUDMAN S91 MELANOMA-BEARING DBA/2J MICE

| Tissue | Salmonella/g Tissue | Tumor/Liver |
|---|---|---|
| Liver (n = 2) | $2.0 \times 10^9$ | — |
| Tumor (n = 4) | $1.5 \pm 0.9 \times 10^9$ | 7,500:1 |

After 10 days of infection (Table 16), the tumors contained an average of $2.9 \times 10^9$ Salmonella/g tumor and $2.7 \times 10^5$ Salmonella/g liver, a ratio of 11,000:1 (tumor:liver), similar to the distribution of bacteria seen 1–2 days post-infection. These results demonstrate that once inoculated (i.p.) into tumor-bearing mice, Salmonella enter the circulatory system, infect the tumor cells, proliferate within the tumors, and exist there in a compartmentalized fashion.

TABLE 16

DISTRIBUTION OF *SALMONELLA TYPHIMURIUM* 10 DAYS FOLLOWING INOCULATION (I.P.) INTO CLOUDMAN 691 MELANOMA-BEARING DBA/2J MICE

| Tissue | Salmonella/gm Tissue | Tumor/Liver | xylose | tetracycline |
|---|---|---|---|---|
| Liver | $2.7 \times 10^5$ | — | neg | 9/10 res |
| Tumor | | | | |
| #1 | $4.2 \times 10^9$ | 16,000:1 | neg | 3/7 res |
| #2 | $3.1 \times 10^9$ | 12,000:1 | neg | 7/8 res |
| #3 | $1.3 \times 10^9$ | 4,800:1 | neg | 8/8 res |
| Average | $2.9 \times 10^9$ | 11,000:1 | | |

The results further demonstrate that 10 days post-infection, all of the bacterial clones examined were xyl$^{neg}$, proving their genetic relationship to the inoculated clone #72$^{5-3-2}$, and that 27/33 clones remained tet$^{res}$, demonstrating high degree of retention (82%) of the HSV TK containing plasmid within the host bacteria. In experiments not shown here, the same plasmid was found to be 100% retained after 42 hours of infection in tumor-bearing mice.

In a continuation of the above experiments summarized in Tables 14, 15 and 16, the Salmonella infections in melanoma-bearing mice were continued for a total of 4 weeks. To alleviate the symptoms of Salmonella poisoning (shaking, matted hair) the animals were placed on antibiotics for the final two weeks. Such antibiotic treatments consisted of the inclusion in the mouse drinking water of SULFATRIM™ Pediatric Suspension (Schein Pharmaceutical, Inc.; sulfamethoxazole 40 mg/ml, trimethoprim 8 mg/ml) at a final concentration of 15 ml SULFATRIM™/500 ml drinking water. At termination of the experiment, the surviving mice were sacrificed by euthanasia, and the tumors and livers were removed. Portions of the tissues (1–2 mm$^3$) were fixed in formalin and stained for histological examination. The remaining portions were weighed, homogenized in 5 ml LB broth/g tissue, and the number of Salmonella were quantitated on LB agar plates. Results are presented in Table 17.

TABLE 17

DISTRIBUTION OF *SALMONELLA TYPHIMURIUM* 4 WEEKS FOLLOWING INOCULATION (I.P.) INTO MELANOMA-BEARING DBA/2J MICE

| Tissue | Salmonella/g tissue | Tumor/Liver |
|---|---|---|
| Liver | $5.1 \times 10^7$ | — |
| Tumor | | |
| #1 | $2.2 \times 10^9$ | 43:1 |
| #2 | $9.4 \times 10^9$ | 18:1 |
| #3 | $2.3 \times 10^9$ | 45:1 |
| #4 | $2.0 \times 10^8$ | 6:1 |
| Average | $1.4 \pm 1 \times 10^9$ | 28:1 |

The excised melanoma tumors averaged less than 1 gram in weight compared to 5–10 gm tumors in control animals at death (data not shown). It was found that these tumors contained an average of $1.4 \times 10^9$ Salmonella/g tumor, similar to the number of tumor-infecting bacteria seen at 1, 2, and 10 days post-inoculation. However, the number of Salmonella in the liver increased during the 4 week infection, so that the average ratio of bacteria in tumor over liver was reduced to 28:1 compared to the ratios obtained with infection periods of up to 10 days as seen in Tables 14, 15 and 16.

15. EXAMPLE

Microscopic Detection of *Salmonella typhimurium* in Melanomas in Vivo 15.1. Detection of *Salmonella typhimurium* Within Cloudman S91 Melanomas Growing in DBA/2J Mice In order to study the histopathology of Salmonella infection in the tumor-bearing mice, representative melanoma tumors were removed from euthanized mice with or without Salmonella infection. Portions of the tissues (1–2 mm$^3$) were fixed in formalin, embedded and sectioned, and the sections stained with either hematoxylin and eosin, or tissue gram stain for histological examination. Results of these studies are shown in FIGS. 5A–B.

Figure 5A:
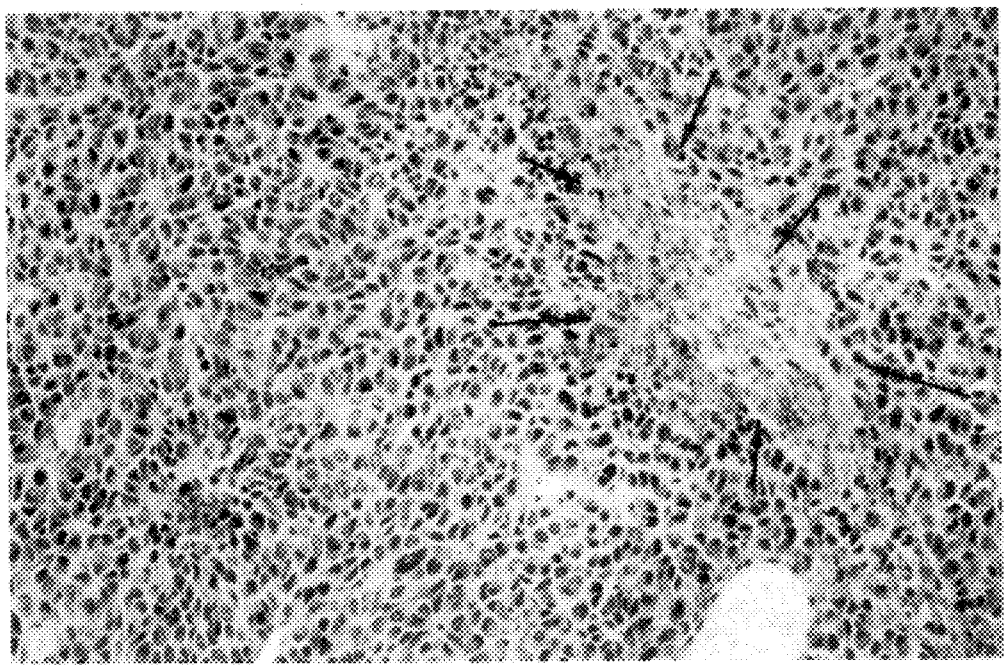
FIGS. 5A–B.
Figure 5B:
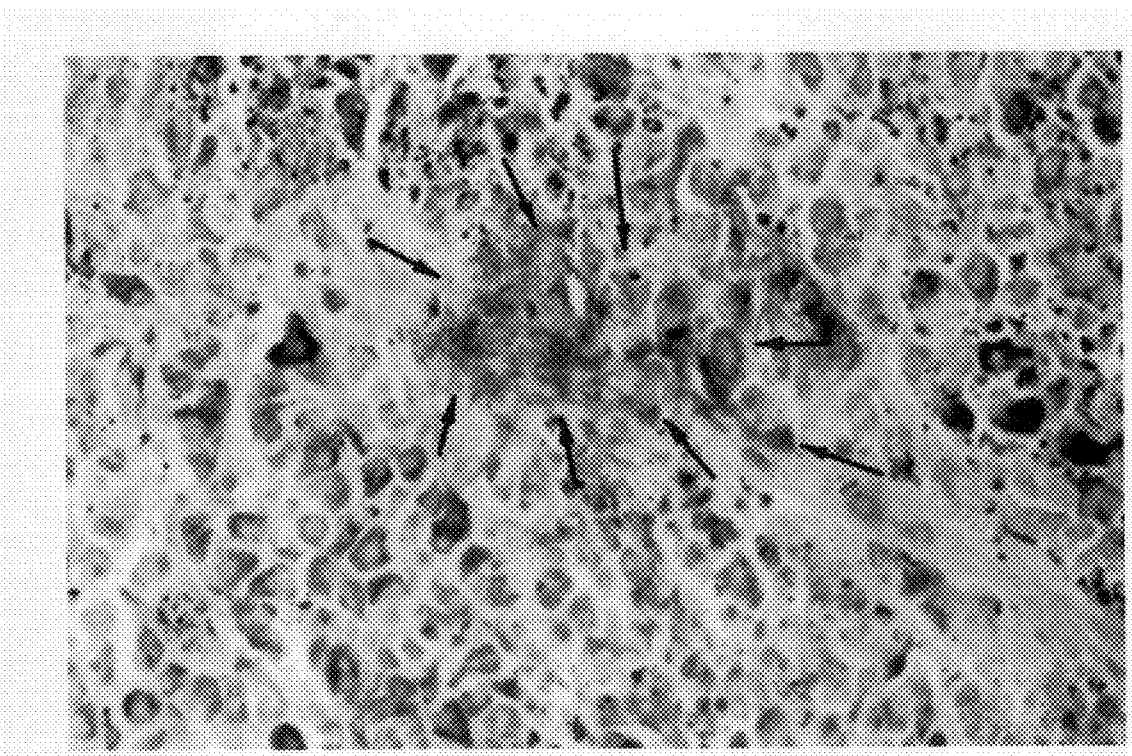

FIGS. 5A–B are photomicrographs of histological sections from a Cloudman S91 melanoma/macrophage hybrid #48 melanoma growing subcutaneously in a DBA/2J mouse. The tumor was excised from a mouse that had been inoculated 2 days earlier with $3 \times 10^5$ c.f.u. *Salmonella typhimurium* super-infective clone 72 carrying the HSV TK gene, $72^{5-3-2}$. A portion of the tumor was weighed, immersed in LB at 5 ml/g tumor, homogenized with a ground glass homogenizer, and the tumor homogenate was plated onto LB-Agar culture plates at various dilutions in order to quantitate the amount of *Salmonella typhimurium* in the tumor. Quantitation of the bacteria revealed that the tumor contained $1.4 \times 10^9$ Salmonella/g. FIG. 5A. A section stained with hematoxyn and eosin shows a cross-section of the tumor with an area of necrosis, denoted by the arrow. FIG. 5B. A section stained with tissue gram stain shows gram negative bacteria in an area of necrosis area of the tumor. When viewed with the light microscope, the bacteria stain pink/purple against a yellow background. Salmonella-infected necrotic areas were surrounded with dead tumor cells that did not stain with tissue gram stain but which could be detected through melanin-containing melanosomes (see FIG. 6). These results show that the necrotic areas of solid tumors are accessible to Salmonella when the bacteria are introduced into a tumor-bearing host via the circulatory system.

In an additional set of analyses, sections of Cloudman S91 melanoma/macrophage hybrid #48 melanoma tumors growing in a Salmonella-infected mouse were examined with the electron microscope. To initiate the experiment, a mouse was inoculated s. c. with $8 \times 10^5$ tumor cells. A palpable tumor mass was detected 11 days later, at which time the mouse was inoculated i.p. with $3.6 \times 10^6$ c.f.u. of *S. typhimurium* super-infective clone #72. Forty-two hours post-inoculation, the mouse was sacrificed by metofane anesthesia. The tumor was excised using aseptic techniques. Quantitation of the bacteria within the tumor revealed that the tumor contained approximately $7.5 \times 10^9$ *S. typhimurium*/g upon excision at 42 hours. In contrast, the concentration of *S. typhimurium* in the liver from the same mouse was approximately $2.0 \times 10^7$/g, a ratio of bacteria in tumor to liver of approximately 400:1.

A second portion of the tumor was cut into 1–2 mm$^3$ pieces and fixed in ½ strength Karnovsky's fixative for 6 hours at 4° C., followed by washing in cacodylate buffer overnight. The tumor tissue was post-fixed with 1% $OsO_4$ and 1.5% potassium ferrocyanide in cacodylate buffer for 2 hours and embedded in Spurr's resin. Ultrathin sections were stained with uranyl acetate and lead citrate. They were viewed with a Zeiss 109 electron microscope.

Figure 6:
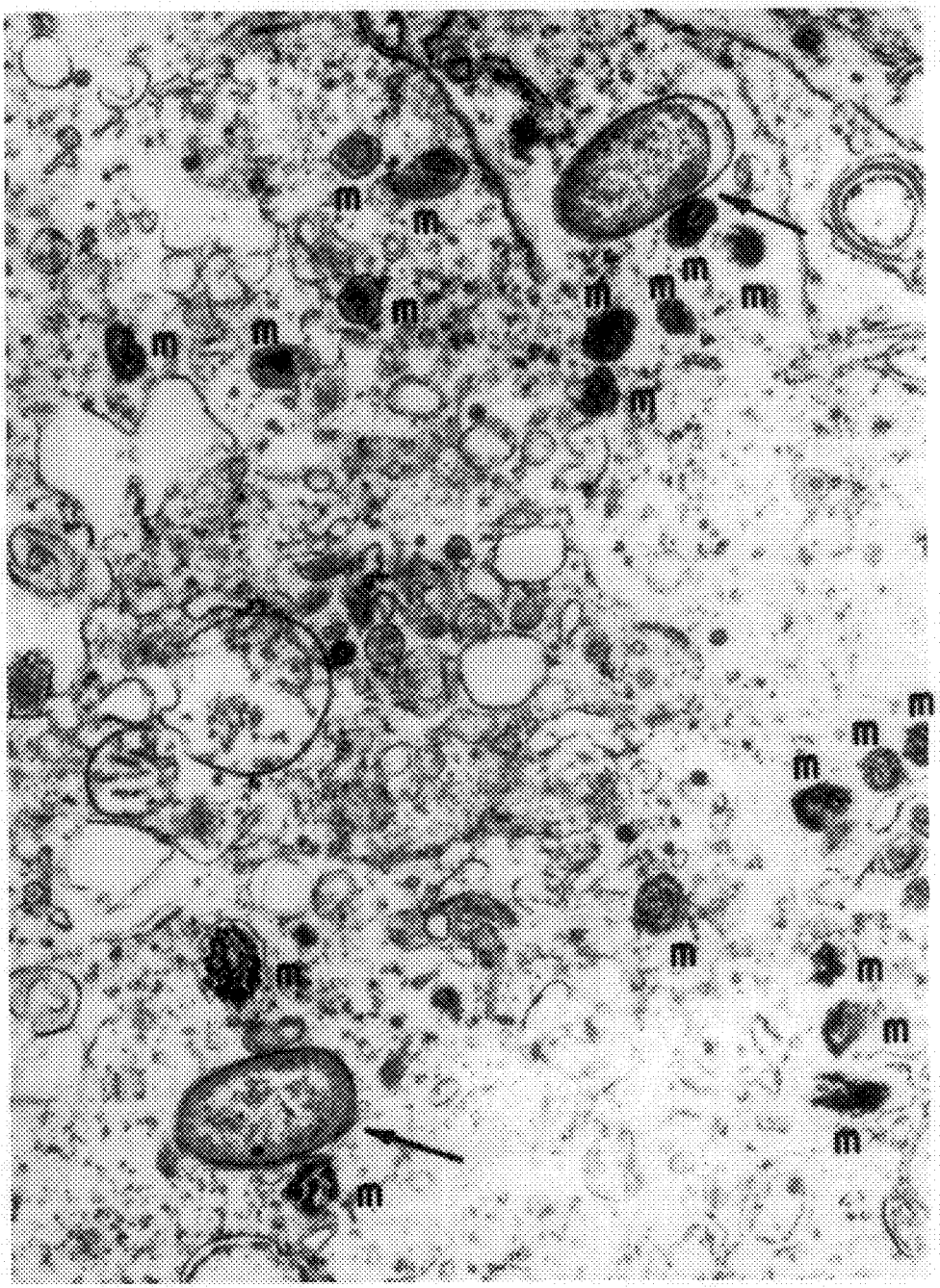
FIG. 6.

Shown in FIG. 6 is an electron micrograph of a field within a melanoma tumor that includes two separate *S. typhimurium* along with numerous melanosomes, which are specialized subcellular organelles present in the cytoplasm of melanoma cells. The presence of bacteria along with the melanosomes provides proof that the *S. typhimurium* entered the cytoplasm of the melanoma cell via the bloodstream of the mouse. The *S. typhimurium* in the electron micrograph appear identical to those shown previously. in intestinal epithelial cells following an experimental infection of the mouse, Takeuchi, 1967, Am. J. Pathol. 50:109–1361.

In summary, i) examination with the light microscope revealed that *Salmonella typhimurium* exists in the necrotic areas of Cloudman S91 melanomas growing in infected DBA/2J mice; and ii) examination with the electron microscope revealed that *Salmonella typhimurium* also exists within the cytoplasm of melanoma tumor cells.

15.2. Distribution of *Salmonella typhimurium* Within Mouse B16F10 Melanoma Tumors Grown In C57BL/6J Mice C57BL/6J mice (11–13 weeks old) were inoculated s.c. in two sites (shoulder and flank), with $3.5 \times 10^5$ B16F10 mouse melanoma cells per site. After the appearance of palpable tumors (approximately 2 weeks) the animals were further inoculated i.p. with about $10^5$ bacteria of the following three strains: i) wild type *Escherichia coli* K-12 strain #CSH 101; ii) *Salmonella typhimurium* strain 14028; and iii) mutant *Salmonella typhimurium* super-infective clone 72 carrying the HSV thymidine kinase gene, $72^{5-3-2}$. After about 2 days of infection, mice were euthanized by anesthesia with metofane. Tumors and livers were removed aseptically, rinsed with sterile 0.9% NaCl, weighed, and homogenized in LB broth at a ration of 5:1 (vol. broth:wt. tumor). Prior to homogenization, 1–2 mm³ pieces of tissue were removed from representative tumors, fixed with ½ strength, Karnovsky's fixative, and processed for analysis with the electron microscope. Bacteria in the homogenates were quantitated by plating onto LB plates, incubating overnight at 37° C., and counting bacterial colonies.

Results were as follows: i) wild type *E. coli* were found in relatively low numbers in both the tumor and liver of the inoculated animals at concentrations averaging $<10^3$/g tumor and $<10^2$/g liver. ii) wild type *S. typhimurium* were found in significantly higher numbers than *E. coli* in both tumor and liver, with infecting bacteria ranging from $2 \times 10^7$ to $6 \times 10^8$ c.f.u./g tumor, and $4 \times 10^6$ c.f.u./g liver. One of the two C57BL/6J mice inoculated with the wild type *S. typhimurium* strain died, possibly from septic shock. iii) *S. typhimurium* super-infective clone 72 were also found in significantly higher numbers than *E. coli* in both tumor and liver, further, the number of clone 72 *S. typhimurium*/g liver was significantly lower than the number of wild type *S. typhimurium*/g liver. The results are detailed below in Table 18.

TABLE 18

DISTRIBUTION OF *SALMONELLA TYPHIMURIUM* AND *ESCHERICHIA COLI* 2 DAYS FOLLOWING INOCULATION (I.P.) INTO C57B6 MICE BEARING B16F10 TUMORS

| Bacterial Strain | Mouse | Tissue | Bacteria/ gm Tissue | Tumor/Liver |
|---|---|---|---|---|
| *E. coli* K-12 (CSH #101) | A | Liver | 355 | — |
| | | Tumor #1 | 1200 | 4:1 |
| | | Tumor#2 | 50 | 1:7 |
| | A' | Liver | 100 | — |
| | | Tumor#1 | 50 | 1:7 |
| *S. typhimurium* (14028 wild type) | B | Liver | $4.3 \times 10^6$ | — |
| | | Tumor #1 | $2.3 \times 10^7$ | 5:1 |
| | | Tumor #2 | $6.0 \times 10^8$ | 136:1 |
| | B' | (dead) | — | — |
| *S. typhimurium* (clone #$72^{5-3-2}$) | C | Liver | $2.0 \times 10^4$ | — |
| | | Tumor #1 | $1.0 \times 10^8$ | 5,000:1 |
| | | Tumor #2 | $1.2 \times 10^5$ | 6:1 |
| | C' | Liver | $8.5 \times 10^4$ | — |
| | | Tumor #1 (2.5 g) | $9.3 \times 10^8$ | 11,000:1 |

In summary, *Salmonella typhimurium* displays natural capabilities over *Escherichia coli* in its ability to infect and proliferate within B16F10 melanoma tumors. Furthermore, super-infective clone $72^{5-3-2}$ displays superior qualities to its wild type parental strain 14028 in its reduced infection of liver in C57BL/6J mice, i.e., the wild-type strain 14028 showed greater infectivity toward liver than did clone $72^{5-3-2}$ The higher infectivity of liver by the wild-type Salmonella was consistent with the observed greater lethality of the wild type stain toward DBA/2J mice and the greater infectivity of liver in DBA/2J mice than that produced by clone 72 as seen in Table 11B. Together, the results in Tables 11B and 18 provide the first evidence that selection for strains of bacteria or other parasites with enhanced tumor specificity in vitro can yield mutant strains with attenuated host toxicity in vivo.

Figure 7:
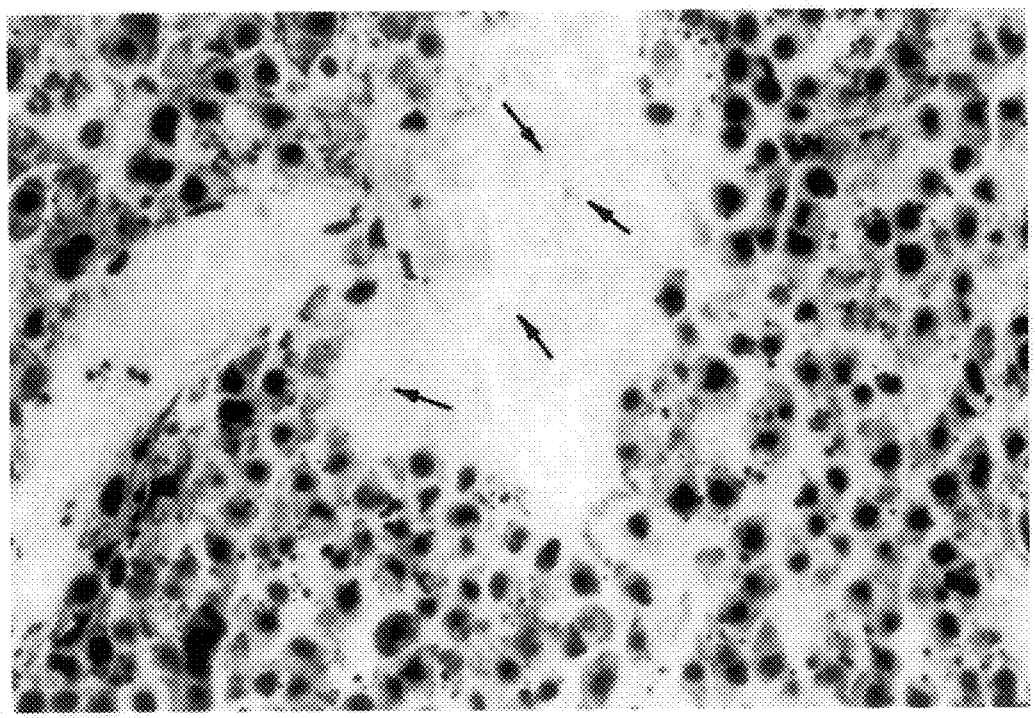
FIG. 7.

15.3. Microscopic Detection of *Salmonella typhimurium* Within B16F10 Melanomas Growing in C57BL/6J Mice Representative B16F10 melanoma tumors were removed from euthanized mice with or without Salmonella infection. Portions of the tissues (1–2 mm³) were fixed informalin, embedded and sectioned, and the sections stained with either hematoxylin and eosin, or tissue gram stain for histological examination. Results of these studies are shown in FIGS. 7A–B. FIGS. 7A and 7B are light micrographs of histological sections from a B16F10 melanoma growing subcutaneously in a C57BL/6J mouse. The tumor was excised from a mouse that had been inoculated 2 days earlier with $2 \times 10^5$ c.f.u. *Salmonella typhimurium* super-infective clone, $72^{5-3-2}$ carrying the HSV TK gene. Quantitation of the bacteria within the tumor revealed that the tumor contained approximately $9 \times 10^8$ c.f.u. *S. typhimurium*/g upon excision 2 days post-infection with bacteria. In contrast, the concentration of *S. typhimurium* in the liver from the same mouse was approximately $2.0 \times 10^5$/g, a ratio of bacteria in tumor to liver of approximately 400:1. FIG. 7: A section stained with tissue gram stain shows gram negative bacteria in an area of necrosis within the tumor. The infected necrotic area is surrounded by dead melanoma cells that do not stain with the tissue gram stain but which appear brown in color due to the presence of melanized melanosomes. When viewed with the light microscope, the bacteria stain pink/purple against a yellow background. The results show that necrotic areas of B16 melanoma tumors are accessible to Salmonella when the bacteria are introduced into a tumor-bearing host via the circulatory system.

A second portion of the above-described tumor was cut into 1 mm³ pieces and fixed in ½ strength Karnovsky's fixative for 6 hours at 4° C., followed by washing in cacodylate buffer overnight. The tumor tissue was post-fixed with 1% $OsO_4$ and 1.5% potassium ferrocyanide in cacodylate buffer for 2 hours, and embedded in Spurr's resin. Ultrathin sections were stained with uranyl acetate and lead citrate. They were viewed with a Zeiss 109 electron microscope as depicted in FIG. 8.

Figure 8:
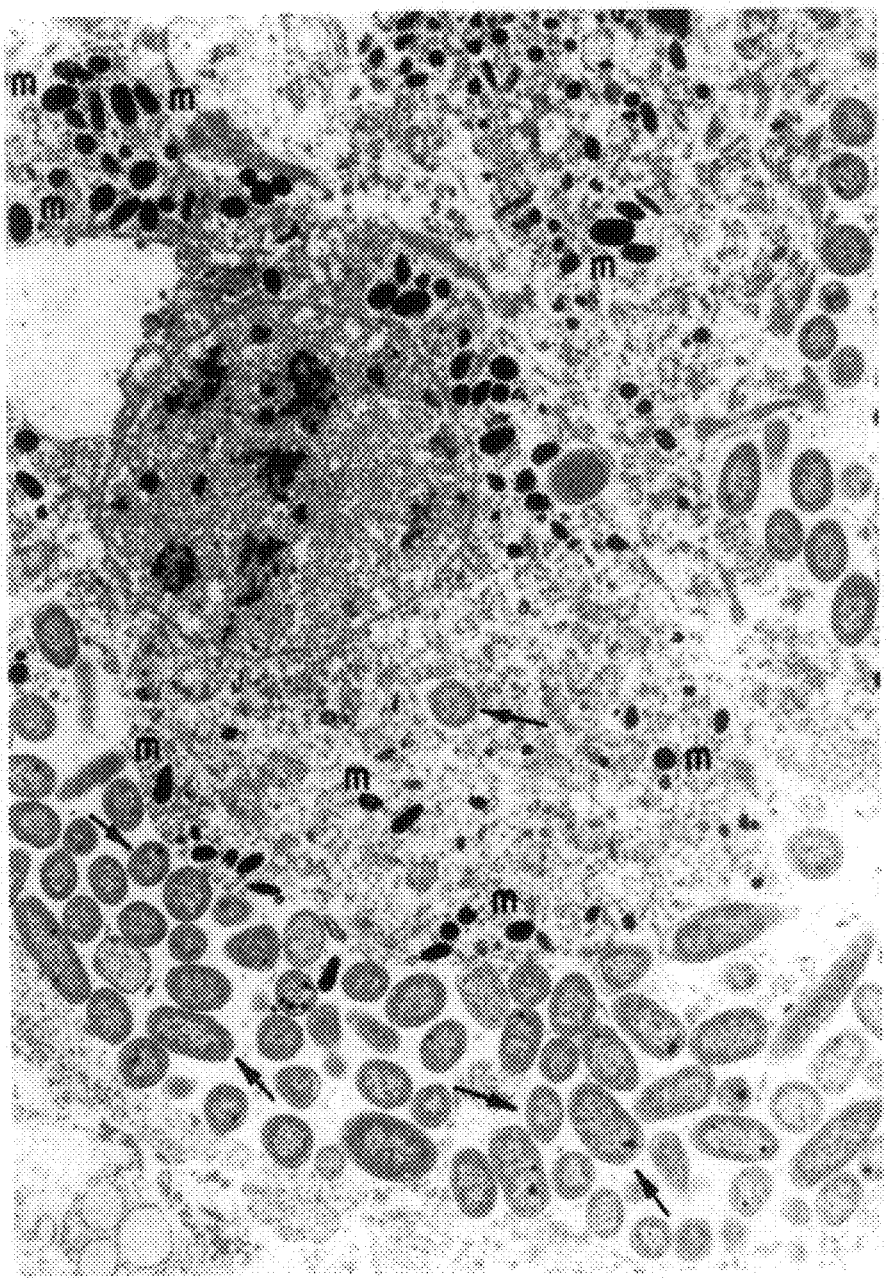
FIG. 8.

The electron micrograph in FIG. 8 shows numerous *Salmonella typhimurium* in extracellular spaces, denoted by arrows, in an area of necrosis. A single bacterium is also seen within the cytoplasm of a dying melanoma cell. The cytoplasm of the dying melanoma cell also contains numerous black melanosomes, characteristic of the B16F10 melanoma.

The *S. typhimurium* in the electron micrograph appear identical to those shown previously in intestinal epithelial cells following an experimental infection of the mouse, Takeuchi, 1967, Am. J. Pathol. 50:109–136.

In summary, i) examination with the light microscope revealed that *Salmonella typhimurium* exist abundantly in the necrotic areas of B16F10 melanomas growing in infected B16F10 mice; and ii) examination with the electron microscope revealed that *Salmonella typhimurium* also exist within the cytoplasm of tumor cells. Salmonella were also observed in tumor-associated neutrophils.

16. EXAMPLE

Use of Super-infective Tumor-specific Gene-delivering *Salmonella typhimurium* For Treatment of Mice Bearing Melanoma Tumors

16.1. Treatment of Cloudman 591 Melanoma

Figure 4A:
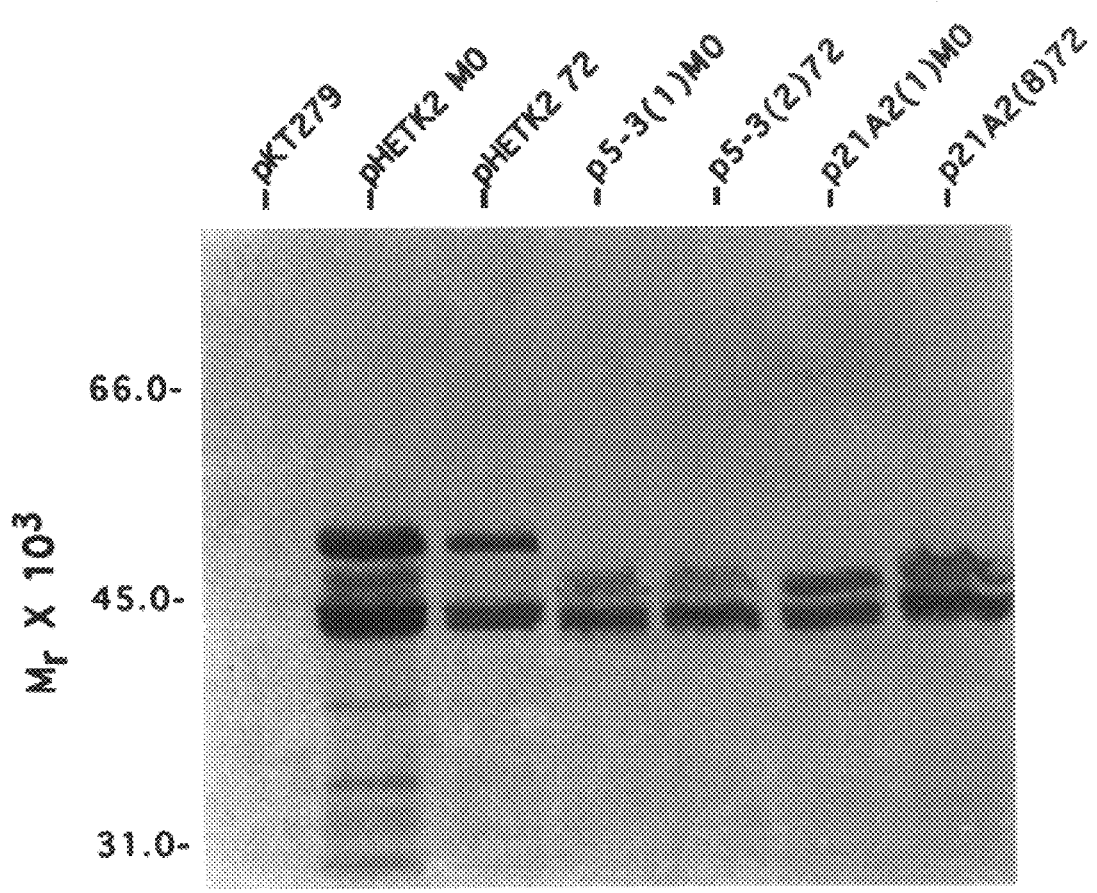
FIGS. 4A–4F relate to producing converting enzyme expression constructs and expression using the same.
Figure 4B:
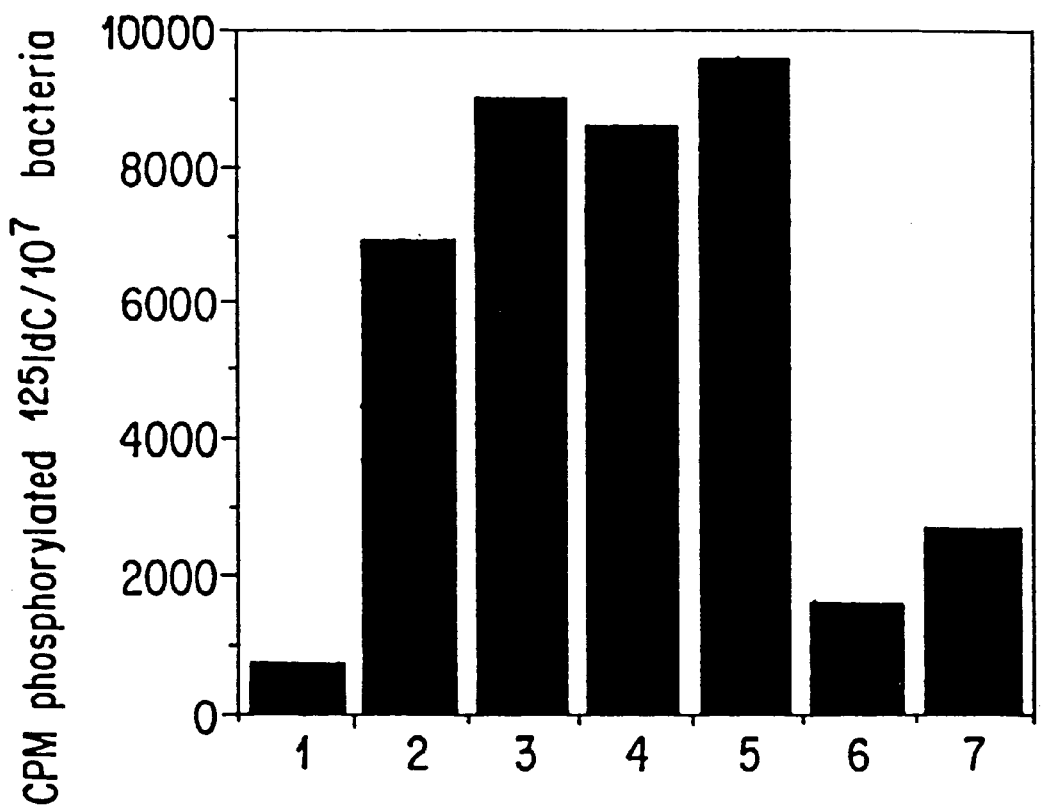
Figure 4C:
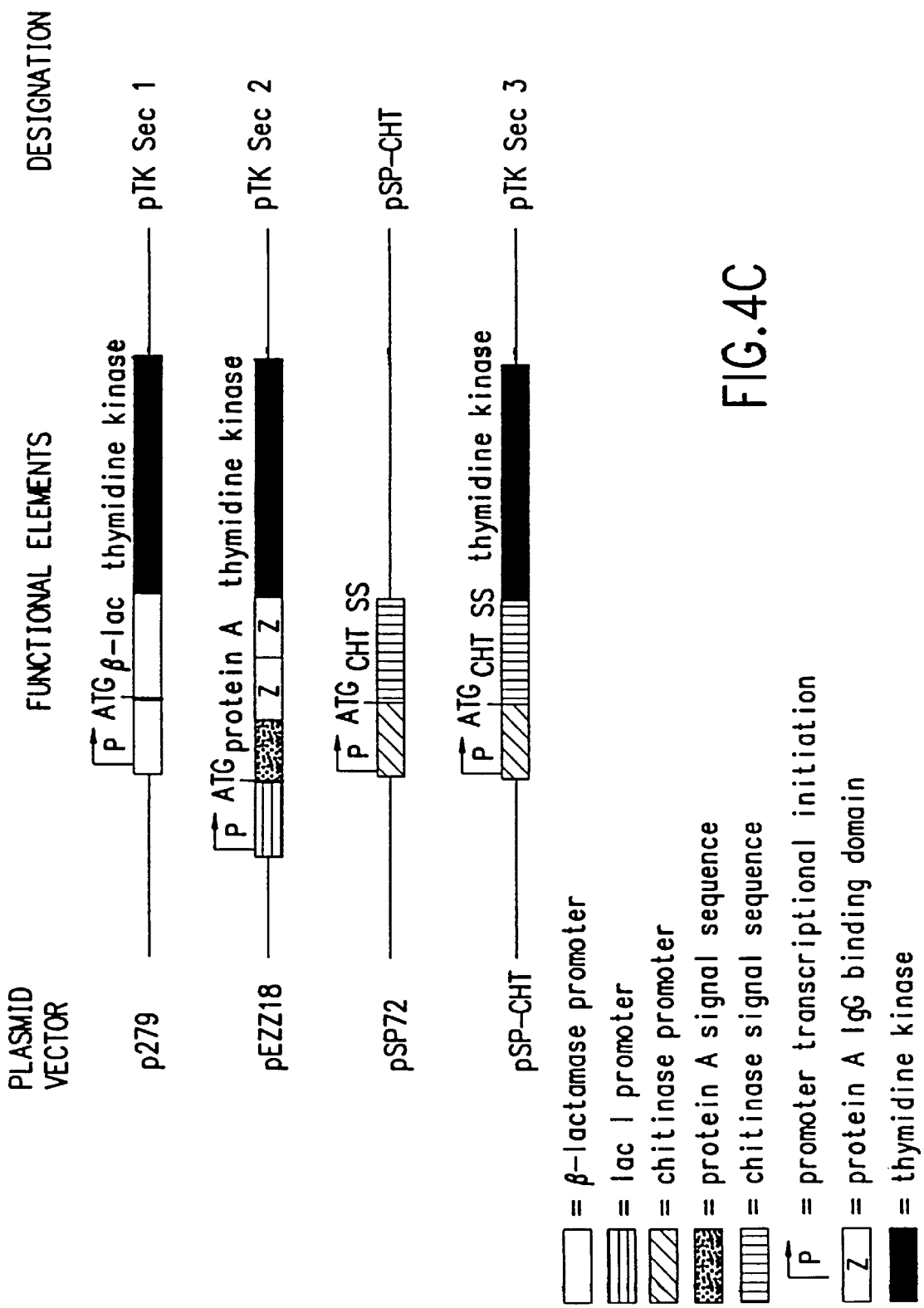
Figure 4D:
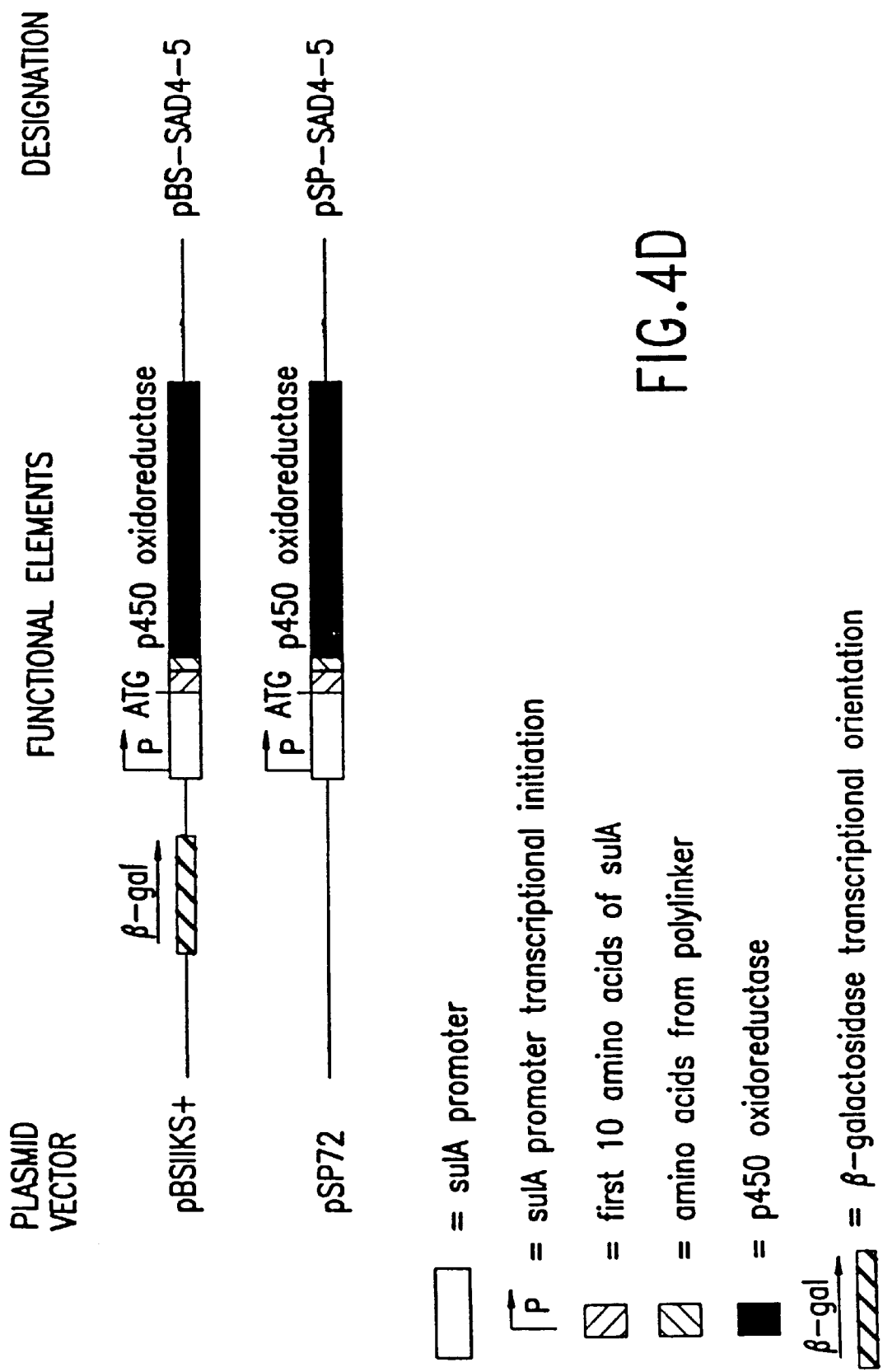
Figure 4E:
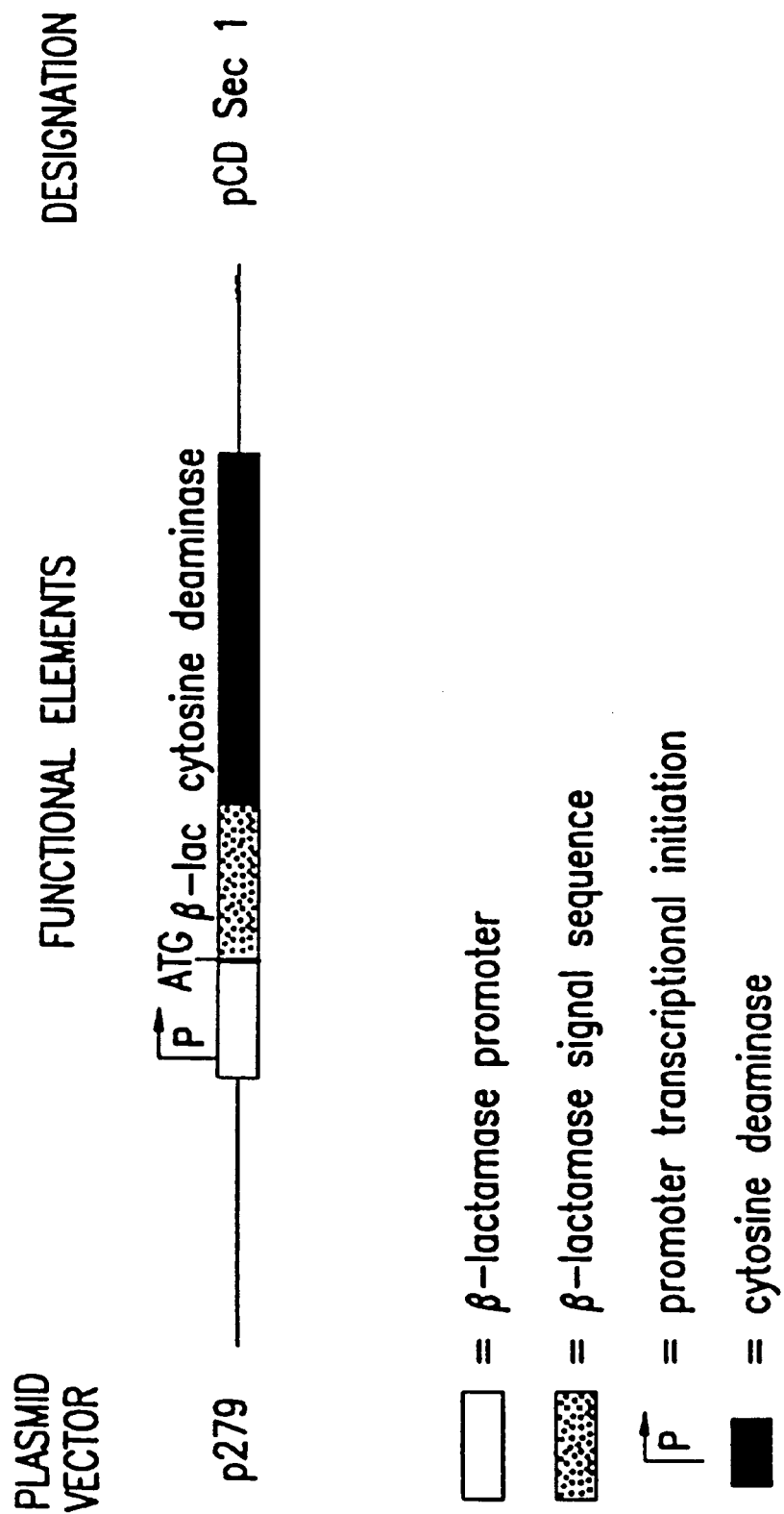
Figure 4F:
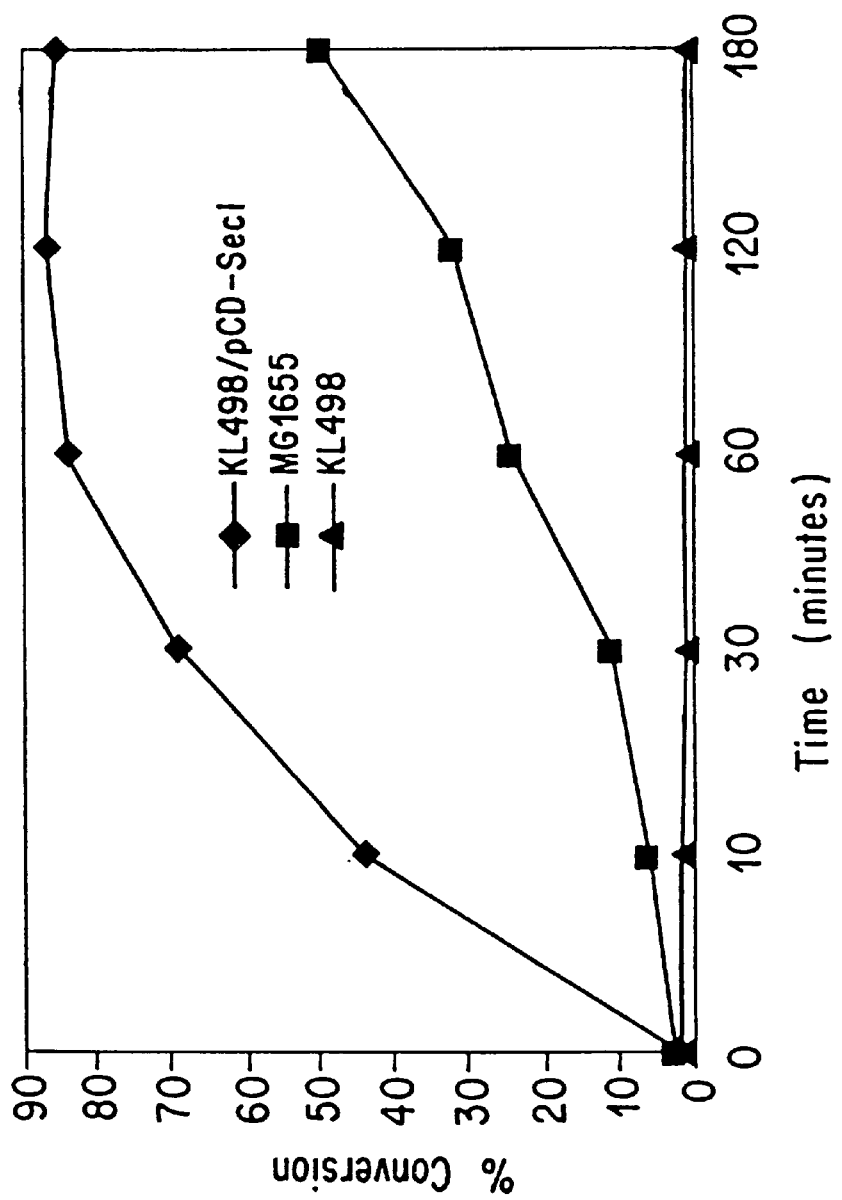

*Salmonella typhimurium* super-infective mutant $72^{5\text{-}3\text{-}2}$, constitutively expressing the Herpes simplex virus thymidine kinase gene with the β-lactamase signal sequence, was used for gene therapy of melanoma in mice (see FIG. 4C). DBA/2J mice (approximately 10 weeks) were inoculated (s.c.) with $3\times10^5$ Cloudman S91 melanoma/macrophage hybrid cells in each of 4 sites over the right and left shoulders and flanks. Tumors were palpable 10–12 days post-inoculation of tumor cells.

After two weeks post-inoculation of tumor cells, tumor-bearing mice were further inoculated (i.p.) with $2\times10^5$ c.f.u. of *S. typhimurium* clone 72 containing the HSV thymidine kinase gene with the β-lactamase secretory signal sequence which is designated $72^{5\text{-}3\text{-}2}$. Twelve hours after inoculation of the bacteria, some of the mice were, further inoculated (i.p.) with 2.5 mg ganciclovir sodium (CYTOVENE™, ganciclovir sodium Syntex Laboratories, Palo Alto, Calif.) in isotonic saline. These same mice received this dosage of ganciclovir four times over a 3 day period. Control tumor-bearing mice also received ganciclovir but no bacteria. Another set of tumor-bearing mice was inoculated with bacteria, but received no ganciclovir. At various times appropriate groups of mice, treated as above, were also given the antibiotic Sulfatrim™ Pediatric Suspension (Schein Pharmaceutical, Inc.; sulfamethoxazole 40 mg/ml, trimethoprim 8 mg/ml) at a concentration of 15 ml Sulfatrim™/500 ml drinking water.

Figure 9:
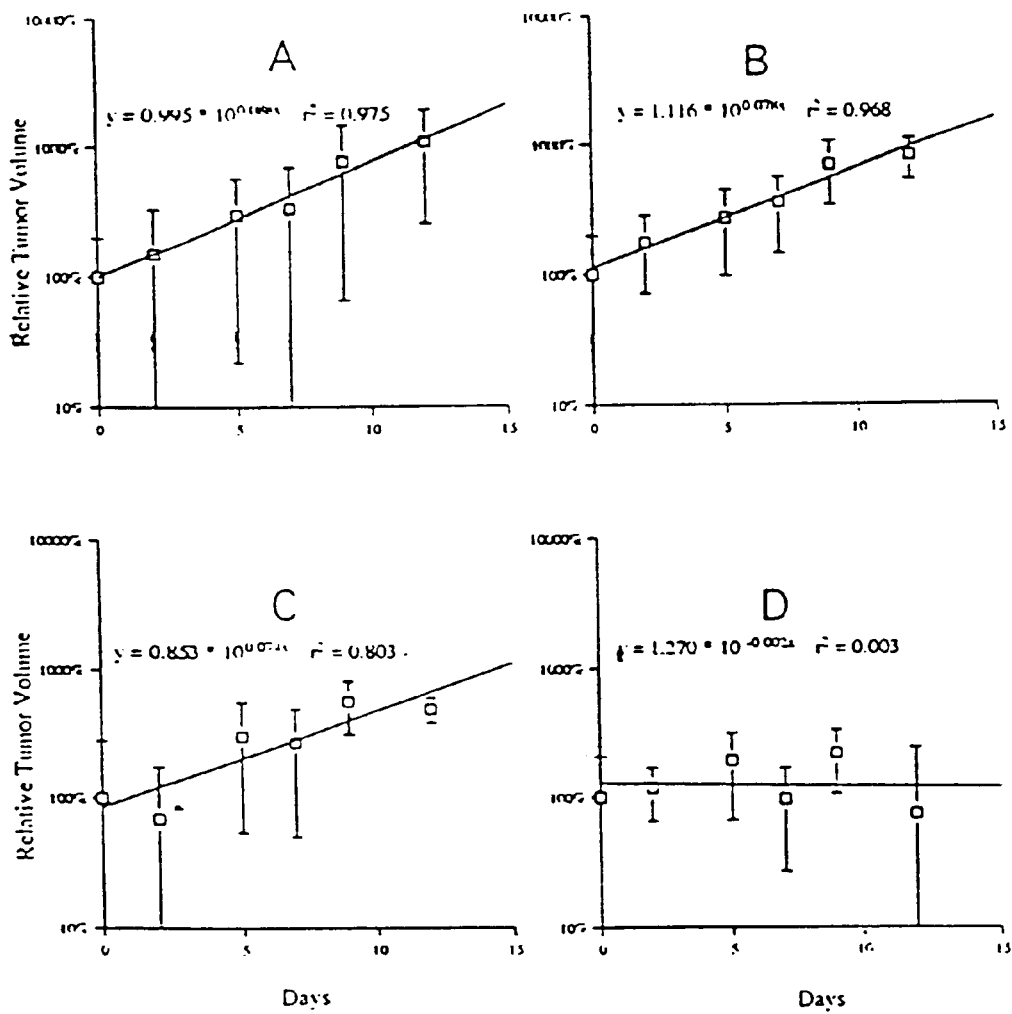
FIGS. 9A–D.

Results were as follows:

1) Control melanoma tumor-bearing mice, receiving ganciclovir and antibiotic treatment (Sulfatrim™ in drinking water) but no bacteria, developed rapidly growing tumors that initially doubled in size every 3 to 4 days, determined by caliper measurements as shown in FIG. 9. These animals exhibited little or no side-effects from the ganciclovir treatment, confirming previous reports on the minimal toxicity of the ganciclovir pro-drug in mice in the absence of a suitable thymidine kinase converting enzyme (Bonnekoh et al, 1995, J. Invest. Dermatol. 104:313–317). By 30 days post-inoculation with tumor cells, all mice in this group had formed massive subcutaneous tumors (5–10 gm) and had died from melanoma.

Figure 10A:
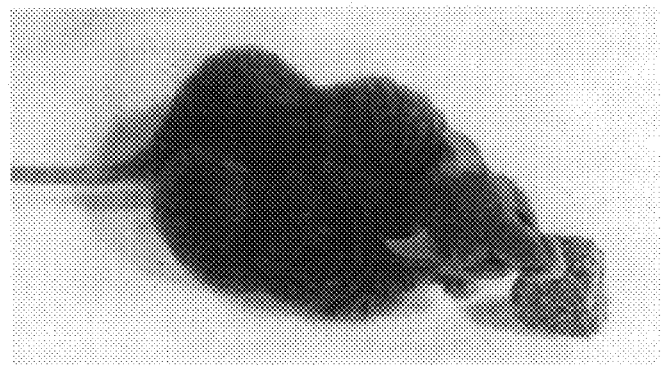
FIGS. 10A–B.
Figure 10B:
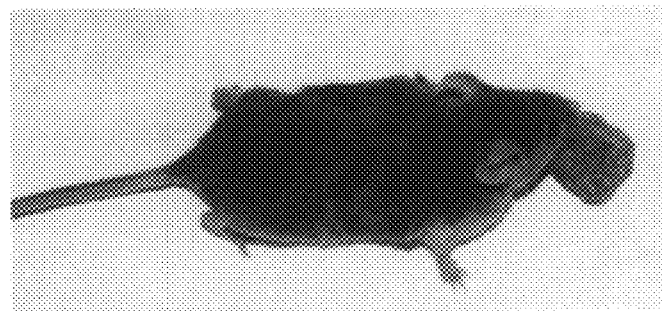

2) One group of tumor-bearing mice received bacteria for a total of 10 days without administration of antibiotics, and received no ganciclovir. These animals had tumors that were significantly reduced in size from the tumors in control mice (FIG. 10). The effect of Salmonella alone on reducing tumor size became evident several days after the effect of Salmonella plus ganciclovir on tumors had been observed as described below. However, all the animals in the "Salmonella alone" group developed symptoms of Salmonella infection (shaking, matted hair) and 50% of these animals succumbed between 5–10 days post-infection. The remaining animals were treated with the antibiotic Sulfatrim™ (Schein Pharmaceutical, Oral Suspension) at a concentration of 15 ml/500 ml drinking water. This treatment reduced the clinical symptoms of Salmonella infection in the mouse population within 24–48 hours. The surviving animals from this protocol had significantly smaller tumors than control animals and remained alive past the 30 day period, when all of the control animals had died from melanoma.

3) Another group of tumor-bearing mice received ganciclovir plus bacteria during a 4-day treatment period. About 50% of the animals succumbed within 1–2 days of this treatment, apparently from the conversion of ganciclovir to its toxic, phosphorylated form by the HSV TK expressed by the Salmonella clone $72^{5\text{-}3\text{-}2}$ within the body of the mouse. At this time ganciclovir treatment was discontinued and the surviving animals were placed on Sulfatrim™ antibiotic to control the Salmonella infection. The total time of exposure to Salmonella without antibiotic was 4 days. The survivors from this protocol had significantly smaller tumors than control animals and remained alive past the 30 day period when all the control animals had died from melanoma (FIG. 11).

In a further set of experiments, tumor progression was measured with calipers in various treated and untreated tumor-bearing mice. Groups of mice bearing Cloudman S91 melanoma/macrophage hybrid #48 melanoma tumors as described above were inoculated (i.p.) with $3\times10^5$ c.f.u. *Salmonella typhimurium* super-infective clone 72 carrying the *Herpes simplex* virus thymidine kinase gene, $72^{5\text{-}3\text{-}2}$. Twenty-four hours after inoculation with bacteria, the mice were further inoculated with ganciclovir at doses of 2.0 mg, with a total of 6 inoculations over a 5 day period. The mice were then subjected to antibiotic treatment with a combination of 15 ml/500 ml SULFATRIM™ sulfa-based veterinary antibiotic and 20 μg/ml BAYTRIL™ enrofloxacin, a quinolone antibiotic (Miles) in their drinking water. BAYTRIL™ enrofloxacin, a quinolone antibiotic is 1-cyclopropyl-7-(4-ethyl-1-piperazinyl)-6-fluoro-1,4-dihydro-4-oxo-3-quinolinecarboxylic acid. Tumor growth was assessed with periodic caliper measurements of tumor length, width, and height, and computed as tumor volume in $mm^3$ by techniques known to the science of tumor biology. Results were plotted on a semi-logarithmic scale and generation times, the time in hours for one doubling in volume, were calculated. The following formula was used:

Generation time=$0.69(t)/\ln(T_1/T_2)$, where t equals the time in hours between the initial tumor volume ($T_1$) and the final tumor volume ($T_2$) over the linear portion of the curve.

The results are shown in FIG. 9 and Table 19. Mean doubling times of tumors in untreated control mice and mice treated with ganciclovir but no Salmonella infection were similar, being 83 and 94 hours respectively. Tumors in mice treated with Salmonella for 5 days but no ganciclovir doubled at a mean rate of 125 hours. Tumors in mice treated with Salmonella for 5 days as well as ganciclovir showed no growth over the 10 day measurement period, and in some cases regressed with the treatment.

TABLE 19

EFFECTS OF HSV TK-CONTAINING *SALMONELLA TYPHIMURIUM* ON THE GROWTH OF CLOUDMAN S91 MELANOMAS IN DBA/2J MICE ± TREATMENT WITH GANCICLOVIR

| Treatment | Mean Tumor Doubling Time (hrs) |
|---|---|
| none | 83 |
| ganciclovir | 94 |
| *S. typhimurium* | 125 |
| *S. typhimurium* + ganciclovir | no growth |

In summary: a) Control tumor-bearing animals receiving ganciclovir and antibiotic treatment, but no Salmonella, succumbed from massive tumors within 30 days of inoculation of tumor cells; b) Animals receiving Salmonella alone followed by antibiotic treatment showed reduced tumor growth rate and prolonged survival over control animals; c) Animals receiving a combination of ganciclovir and Salmonella followed by antibiotic treatment showed little or no tumor growth compared to control animals, and prolonged survival over control animals. The results indicate that *Salmonella typhimurium* expressing the *Herpes simplex* virus thymidine kinase gene was able to convert ganciclovir to its phosphorylated form within the melanoma tumors, thus reducing tumor size and prolonging survival of the mice.

16.2. Treatment of B16F10 Melanoma

C57B6 mice were inoculated s.c., left shoulder region, with 5–105 B16F10 melanoma cells from culture. At 8 days post-tumor implantation some of the mice were further inoculated i.p. with 2–10$^6$ c.f.u. attenuated *Salmonella typhimurium* strains YS721, YS7211, YS7212 or YS7213 (see Section 18, infra) each carrying the HSV TK gene. At 11 days post-tumor implantation, GCV (ganciclovir sodium, CYTOVENE™, Syntex Laboratories, Palo Alto, Calif.) was inoculated i.p. into groups of mice (n=5 or n=10) under the following treatment protocols: a) total dose=7.5 mg/mouse (2.5 mg day 11, 1.25 mg day 12; 2.5 mg day 18, 1.25 mg day 19); b) total dose=5.0 mg/mouse (2.5 mg day 11, 2.5 mg day 12); c) total dose=3.75 mg/mouse (2.5 mg day 11, 1.25 mg day 12); d) total dose=2.5 mg/mouse (1.25 mg day 11, 1.25 mg day 12); e) total dose=1.25 mg/mouse (1.25 mg day 11). At 18 days post-tumor implantation (10 days post bacterial inoculation) all animals were given enrofloxacin antibiotic, 0.2 mg/ml, in their drinking water (BAYTRIL™) and maintained with this antibiotic supplement for 2 weeks. Tumor growth was assessed by caliper measurements and computed as volume in mm$^3$. Animals were euthanized and listed as dead when the sum of their tumor measurements, length+width+height, reached 60 mm, or when they became moribund (listless, cessation of drinking).

The results obtained are illustrated in FIGS. 11C–H in Table 19(A).

TABLE 19(A)

SURVIVAL OF C57B6 MICE INOCULATED WITH *SALMONELLA TYPHIMURIUM* ± HSV TK GENE: EFFECTS OF GANCICLOVIR

| Strain | (n=) | GCV | Time Days ± S.D. | Treated/Control T/C |
|---|---|---|---|---|
| Control | (10) | -0- | 25 ± 0 | 1.0 |
|  | (10) | 3.75 mg | 27 ± 1 | 1.1 |
| YS7212 | (10) | -0- | 42 ± 2 | 1.7 |
| YS7212 | (10) | 3.75 mg | 33 ± 4 | 1.3 |
| YS7212/p5-3 | (10) | -0- | 45 ± 3 | 1.8 |
| YS7212/p5-3 | (10) | 3.75 mg | 40 ± 4 | 1.6 |
| YS7213 | (10) | -0- | 34 ± 2 | 1.3 |
| YS7213 | (10) | 3.75 mg | 35 ± 2 | 1.4 |
| YS7213/p5-3 | (10) | -0- | 29 ± 2 | 1.2 |
| YS7213/p5-3 | (10) | 3.75 mg | 33 ± 2 | 1.3 |
| YS7211 | (10) | -0- | 40 ± 4 | 1.6 |
| YS7211 | (10) | 3.75 mg | 35 ± 4 | 1.4 |
| YS7211/p5-3 | (10) | -0- | 34 ± 2 | 1.4 |
| YS7211/p5-3 | (5) | 1.25 mg | 30 ± 4 | 1.2 |
|  | (5) | 2.50 mg | 37 ± 4 | 1.5 |
|  | (5) | 3.75 mg | 38 ± 4 | 1.5 |
|  | (5) | 5.0 mg | 42 ± 6 | 1.7 |
|  | (5) | 7.5 mg | 39 ± 6 | 1.6 |

*Time of death post tumor cell inoculation.

The results from the various treatment protocols for the B16F10 melanoma-bearing mice were as follows:

1) Effects of GCV on Tumor-bearing Animals With no Bacterial Inoculation

Figure 11A:
FIGS. 11A–11H relate to the effects of gancicylovir on tumor cell growth, in vivo or in vitro.
Figure 11B:
Figure 11C:
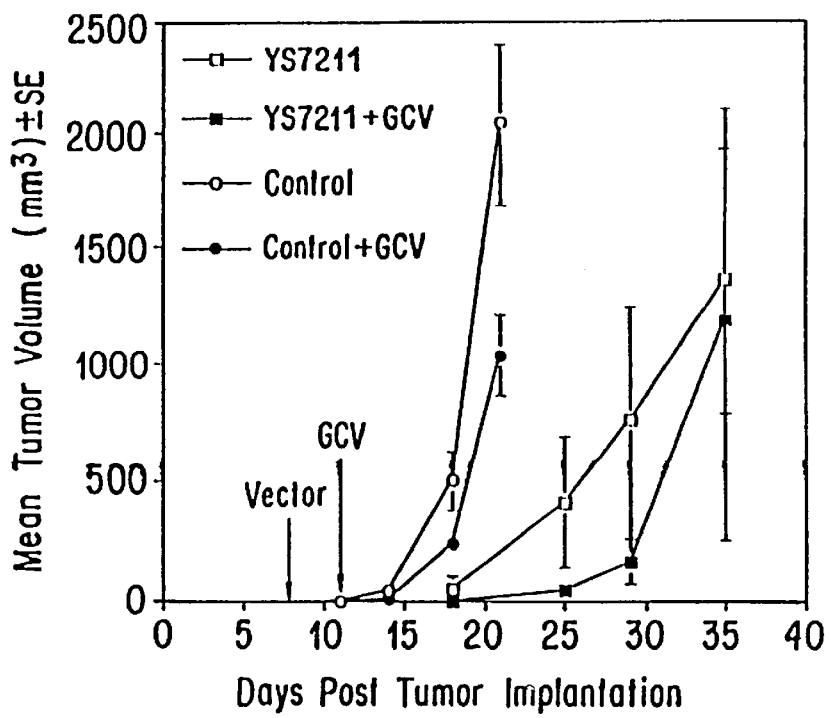
Figure 11D:
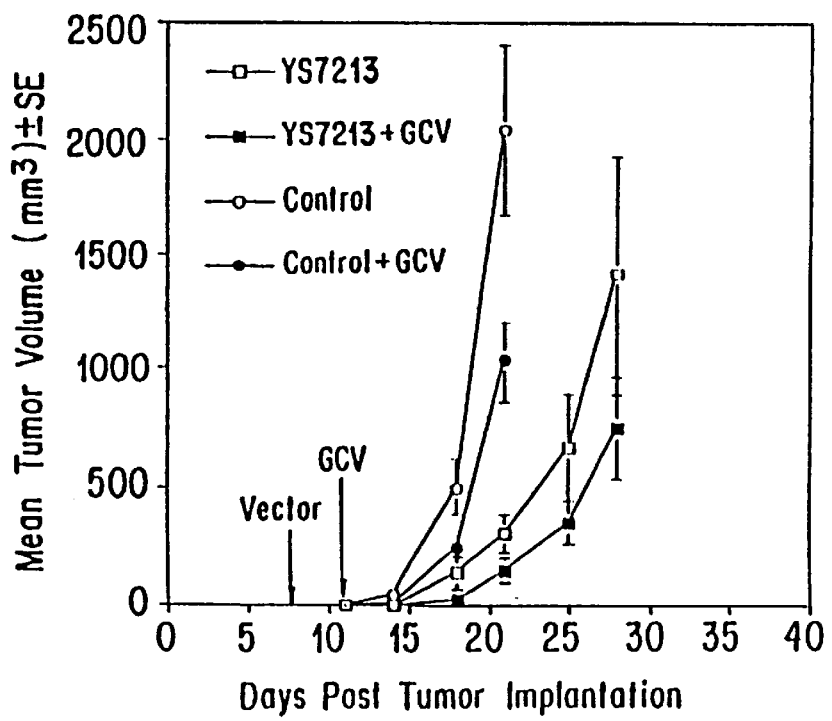
Figure 11E:
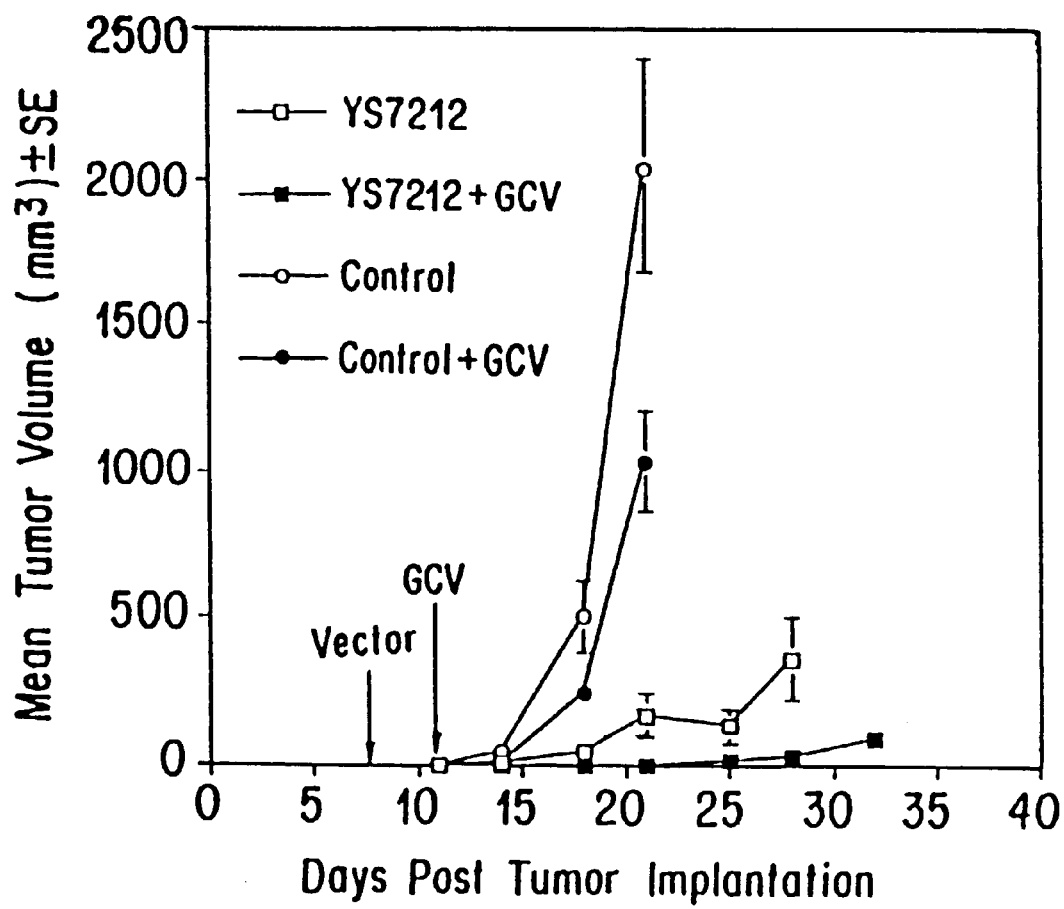
Figure 11F:
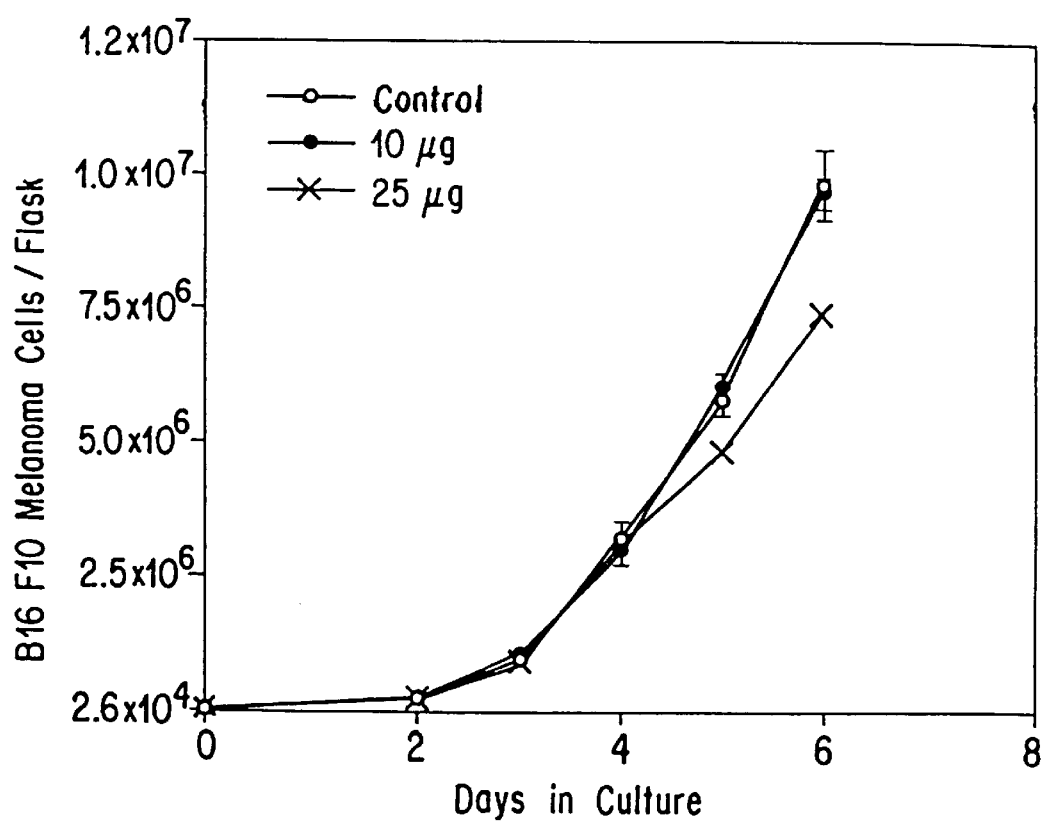
Figure 11G:
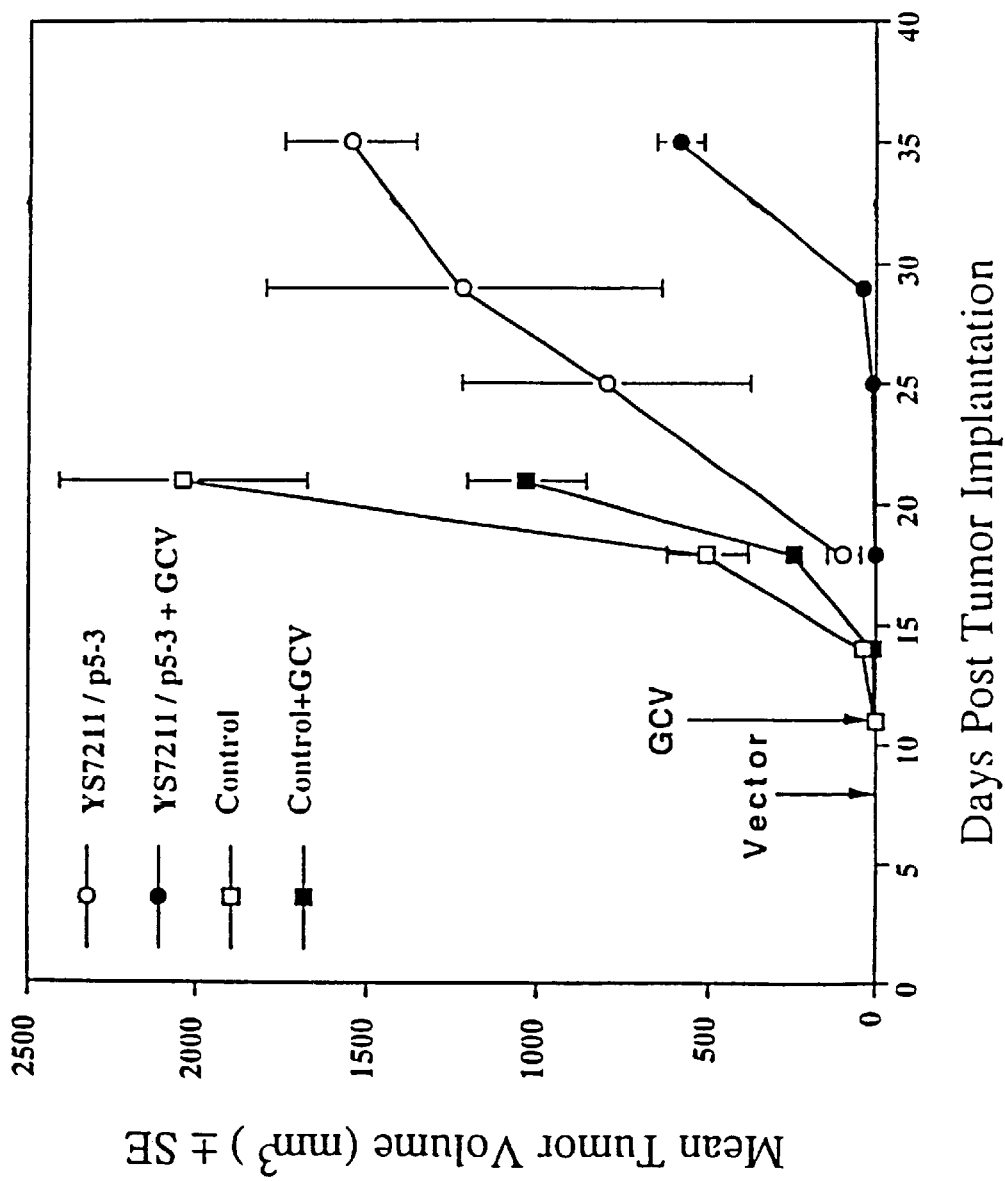
Figure 11H:
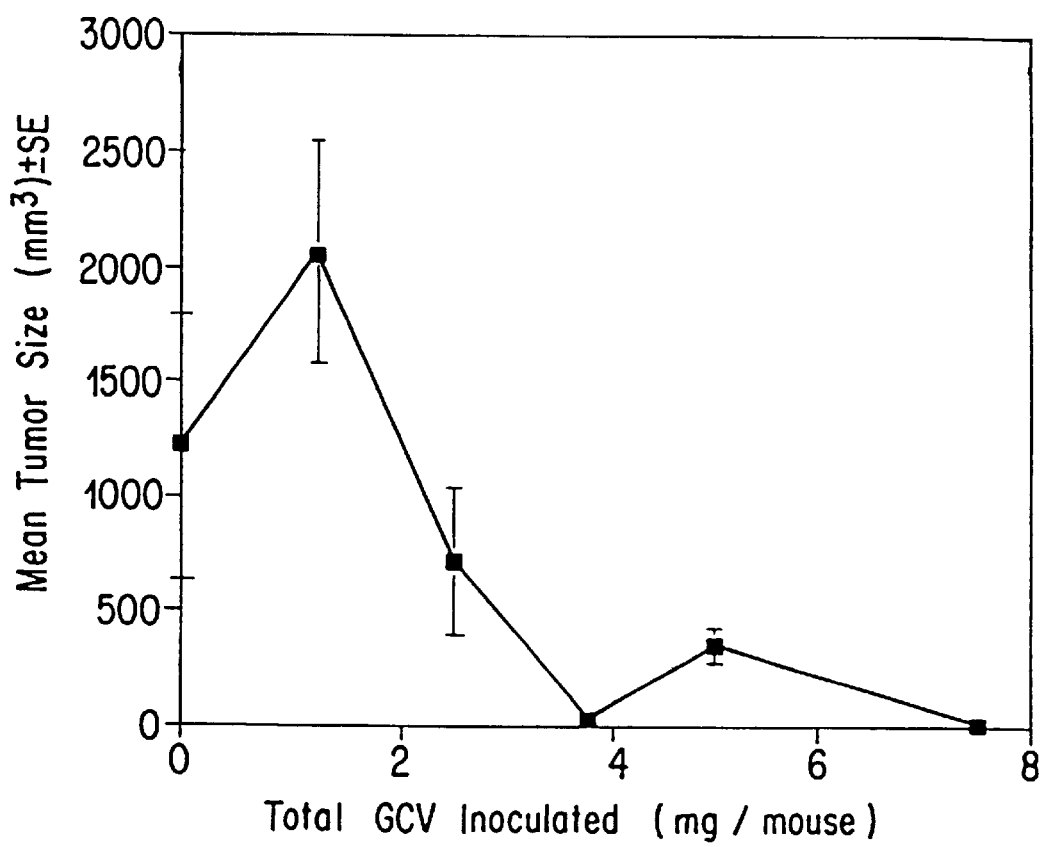

Mice receiving melanoma cells but no bacteria were treated with GCV on days 11–12 post inoculation with tumor cells at doses from 3.75 mg–10 mg/mouse, depending on the experiment. In all trials, mice treated with GCV but no bacteria showed a small reduction in tumor volume that was noticeable within 5 days of GCV treatment and which persisted through the duration of the experiment, as shown in FIGS. 11C–E. GCV also elicited small but reproducible increases in survival time compared to that of non-treated control animals, as outlined in Table 19(A). These effects of GCV in the absence of bacterial treatment were not dependent upon dosage over the range studied.

These results demonstrate that the B16F10 cells employed in the experiment might have had the capacity to convert GCV to its toxic, phosphorylated form. Consistent with such a notion, it was found that proliferation of the B16F10 melanoma cells in culture was significantly suppressed when GCV was supplemented to the culture medium at 25 μg/ml, but not at 10 μg/ml as shown in FIG. 11-F. Similar effects of GCV on DBA/2J mice bearing Cloudman S91 melanomax macrophage hybrid 48, but not inoculated with bacteria, are reported in the Table 19.

2) Effects of GCV on Tumor-bearing Animals Treated With Bacteria Not Containing an HSV TK-plasmid When tumor-bearing mice were inoculated with Salmonella strains YS7211, YS7212 and YS7213, none of which contained the HSV TK gene, and then treated with GVC, GCV-mediated suppression of tumor growth was evident. Tumor suppression achieved with GCV was significantly greater than that seen with the bacteria alone, even when the suppressive effect of GCV on B16F10 tumors in control animals was taken into account. This indicated that *Salmonella typhimurium* could convert GCV to its phosphorylated, toxic form without the HSV TK gene, perhaps through endogenous phosphotransferase enzymes (Littler, et al., 1992, Nature 358:160–162; Sullivan et al., 1992, Nature 358:362–364). Consistent with this notion was the finding that in addition to suppressing tumor growth, some combinations of bacteria and GCV treatment were highly toxic, shortening survival times of the animals, shown in Table 19(A). Toxicity might have resulted from production of phosphorylated GCV by those bacteria located in normal tissues such as liver or bone marrow.

3) Effects of GCV on Tumor-bearing Animals Treated With Bacteria Containing an HSV TK-plasmid Tumor-bearing mice inoculated with HSV TK plasmid-containing Salmonella clone YS7211 (YS7211/p5-3) showed suppression of tumor growth and prolonged survival even in the absence of GCV treatment as shown in FIG. 11-G. Further, animals bearing both tumors and YS7211/p5-3 and additionally treated with 3.75 mg GCV showed significant suppression of tumor growth above that seen in the absence of GCV. Using YS7211/p5-3 as a vector, GCV-mediated tumor suppression was evident in a dose-responsive manner when measured 28 days post implantation of tumors as shown in FIG. 11-H. Tumor suppression correlated with increased average survival times for some categories of GCV-treated, tumor-bearing mice when compared to those inoculated with YS7211/p5-3 but not receiving GCV.

In summary:

1) In tumor-bearing animals not inoculated with Salmonella, GCV had a small suppressive effect on tumor growth that correlated with a small prolongation of survival.

2) Tumor-bearing animals inoculated with Salmonella not containing the HSV TK plasmid showed marked tumor suppression in response to GCV, above that seen in animals not treated with bacteria. In addition, some combinations of GCV and bacterial treatment were highly toxic to the animals, possibly through conversion of GCV to its toxic form by bacteria in extra-tumoral tissues such as liver or bone marrow.

3) Tumor-bearing animals inoculated with Salmonella containing the HSV TK plasmid also showed strong tumor suppression in response to GCV. It was not possible in these experiments to evaluate the relative contributions of ISV TK as compared to endogenous Salmonella enzymes in the phosphorylation of GCV. However, using as a vector clone YS7211 containing the HSV TK expression plasmid, GCV-mediated tumor suppression and prolonged survival was demonstrated in a dose-dependent manner, see FIG. 11-H.

17. EXAMPLE

Localization of *Salmonella typhimurium* Within Human Tumors Grown in NU/NU Mice The following experiments demonstrate localization of Salmonella in human tumors in experimental animals.

17.1. Localization of Salmonella Within Human Colon Tumors

NU/NU (BALB C) mice (9–10 weeks old) were inoculated s.c. in two areas (shoulder and flank), each with $1.5 \times 10^7$ HCT 116 human colon carcinoma cells. After the appearance of palpable, vascularized tumors (approximately 2 weeks) the animals were further inoculated i.p. with $3 \times 10^5$ *Salmonella typhimurium* super-infective clone $72^{5-3-2}$ carrying the HSV thymidine kinase gene. After 3.5 hours, 21 hours, and 72 hours of infection, mice were euthanized by anesthesia with metofane. Tumors and livers were removed aseptically, rinsed with sterile NaCl (0.9%), weighed, and homogenized with LB broth at a ration of 5:1 (vol. broth:wt. tumor). At 72 hours, prior to homogenization, pieces (1–2 mm$^3$) were removed from representative tumors, fixed with ½ strength Karnovsky's fixative, and processed for analysis with the electron microscope. Bacteria in the homogenates were quantitated by plating onto LB plates, incubating overnight at 37° C., and counting bacterial colonies.

Results were as follows: At 3.5 hours and 21 hours there were insignificant levels of bacteria in the tumors or livers, even when the homogenates were plated undiluted onto LB agar plates. However, after 3 days 3/6 animals displayed high levels of Salmonella in the colon tumors, with bacterial tumor:liver ratios ranging up to 36,000:1. Data for these animals are summarized below in Table 20.

TABLE 20

DISTRIBUTION OF *SALMONELLA TYPHIMURIUM* 3 DAYS FOLLOWING INOCULATION (I.P.) INTO HUMAN COLON CARCINOMA-BEARING NU/NU MICE

|  | Salmonella/gm tissue | Tumor/Liver |
| --- | --- | --- |
| Mouse A |  |  |
| Liver | $2.6 \times 10^4$ |  |
| Tumor | $6.9 \times 10^8$ | 26,500:1 |
| Mouse D |  |  |
| Liver | $1.6 \times 10^6$ |  |
| Tumor | $3.1 \times 10^9$ | 2,000:1 |
| Mouse E |  |  |
| Liver | $1.0 \times 10^5$ |  |
| Tumor | $3.6 \times 10^9$ | 36,000:1 |

Figure 12A:
FIGS. 12A–B are electron micrographs.
Figure 12B:
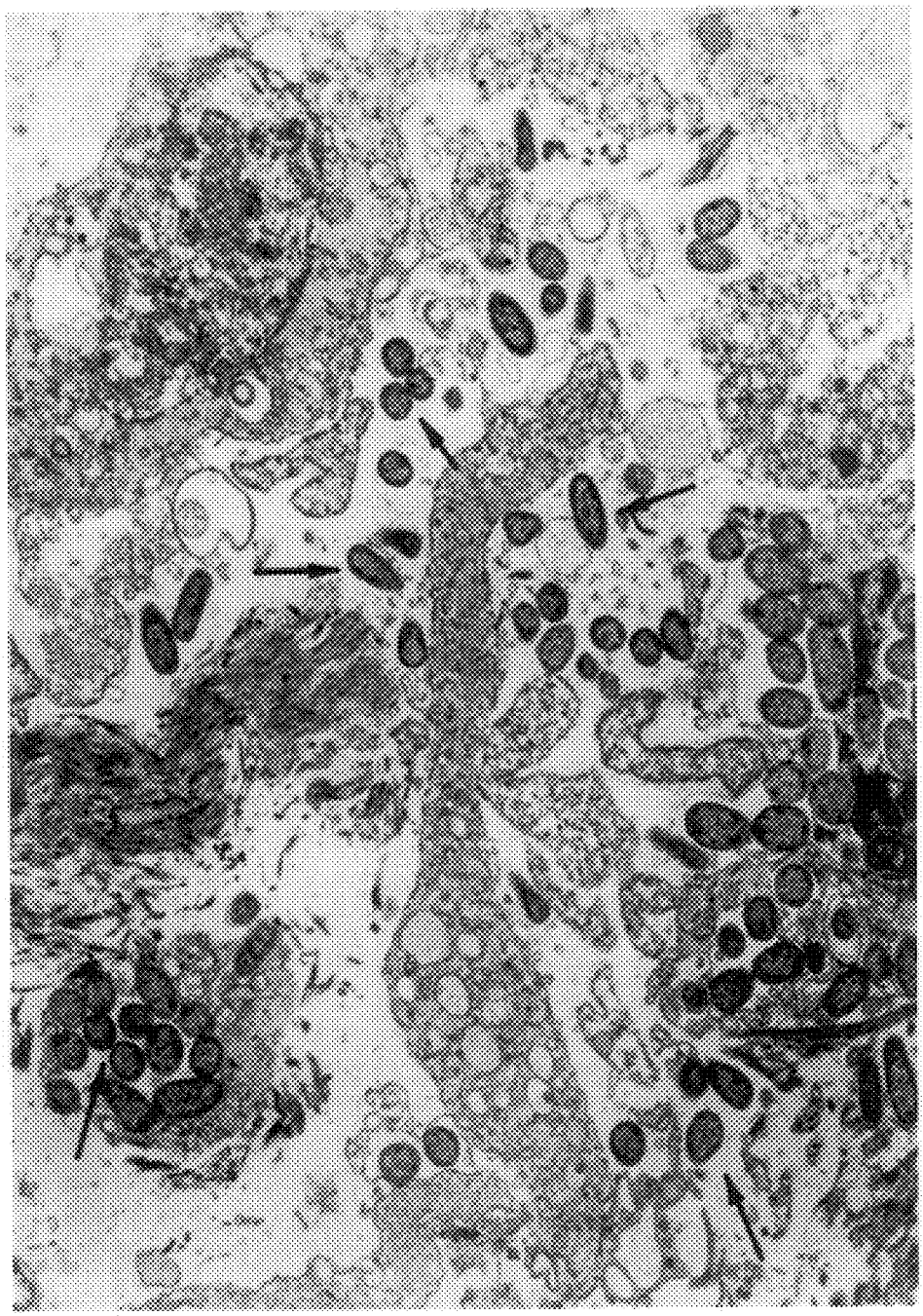

Shown in FIG. 12-A an electron micrograph of a section from the HCT colon tumor excised from mouse A (Table 20) in which the number of Salmonella found to be $6.9 \times 10^8$/g tumor, and the tumor:liver ratio of infecting bacteria was 26,500:1. Shown in the micrograph are numerous *Salmonella typhimurium* within a vacuole in the cytoplasm of a neutrophil associated with the tumor. Some of the bacteria are undergoing division as denoted by the arrow. The neutrophil or polymorphonucleoleukocyte is characterized by its multi-lobed nucleus (n). Salmonella in tumor-associated neutrophils was also seen in infected B16F10 melanomas as described herein. The presence of bacteria in both colon and melanoma tumor-associated neutrophils following infection of tumor-bearing mice suggests that the Salmonella may have stimulated a host cellular immune response to the tumor cells. Enhancement of tumor immunity is thus another potential advantage in the use of parasites as tumor-specific therapeutic vectors.

17.2. Localization of Salmonella Within Various Human Tumors

Nu/nu (BALB C) mice (9–12 weeks old) were inoculated s.c. in the left shoulder region with $1-1.5 \times 10^7$ cells of the human lung carcinoma A549, human colon carcinoma HCT 116, human renal carcinoma CRL 1611, or human hepatoma HTB 52 (American Type Culture Collection). When palpable tumors developed, the mice were inoculated further with $2-5 \times 10^6$ cfu *Salmonella typhimurium* clone 72 for animals bearing 10 human lung, liver, and renal tumors, and clone $72^{5-3-2}$ for animals bearing human colon tumors. Clone $72^{5-3-2}$ carries the HSV thymidine kinase transcription unit. After 66–96 hours the animals were sacrificed, and the tumors and livers were removed and weighed. The tumor was homogenized in 5 vol LB broth/gram wet weight tissue. Homogenates were quantitated by serial dilution on LB agar plates for the number of bacteria. The results are presented in Table 20(A) and represent the average±standard deviation for n=3–4 animals.

TABLE 20(A)

BIODISTRIBUTION OF *SALMONELLA TYPHIMURIUM* CLONE 72 IN NU/NU MICE BEARING HUMAN CARCINOMAS OF THE LUNG, COLON, KIDNEY, AND LIVER

| Primary Tumor | Salmonella/g tissue: | | Tumor wt (mg) | Tumor:Liver |
| --- | --- | --- | --- | --- |
|  | Tumor | Liver |  |  |
| lung carcinoma | $3.2 \pm 1.4 \times 10^9$ | $1.0 \times 0.3 \times 10^7$ | $462 \pm 186$ | 320:1 |
| colon carcinoma | $2.5 \pm 1.6 \times 10^9$ | $5.8 \pm 8.9 \times 10^5$ | $428 \pm 235$ | 4300:1 |
| hepatoma | $6.7 \pm 11 \times 10^8$ | $5.7 \pm 9.0 \times 10^6$ | $103 \pm 29$ | 120:1 |
| renal carcinoma | $1.4 \pm 1.8 \times 10^8$ | $6.0 \pm 3.0 \times 10^5$ | $103 \pm 99$ | 230:1 |

As shown in Table 20-A, when inoculated i.p. into nu/nu mice, *Salmonella typhimurium* clone 72 was able to target human carcinomas of the lung, colon, kidney, and liver, and proliferate within them, generally, but not always, reaching levels of $10^8-10^9$/g tumor. In the BALB/c nu/nu mice used, the skin was hairless and translucent allowing it to be determined visually that all the tumors were vascularized. The ranges of wet weights of the Salmonella-infected tumors were lung carcinoma, 220–600 mg; colon carcinoma, 160–600 mg; hepatoma, 70–120 mg; and renal carcinoma, 40–250 mg.

Bacterial colonies were picked randomly from liver and tumor homogenates obtained from renal carcinoma- and hepatoma-bearing nu/nu mice 96 hrs post-inoculation of clone 72 and tested for phenotype by replicate plating. In all homogenates tested, 50/50 colonies were found to be Ade$^-$ and Xyl$^{neg}$, consistent with the clone 72 phenotype.

The results further support the notion that derivatives of *Salmonella typhimurium* are useful as therapeutic vectors for a broad range of solid tumors, independent of the tumor origin or size. In several studies Salmonella clone 72 and its derivatives targeted and amplified within highly vascularized tumors as small as 40–100 mg in the case of human tumors in nu/nu mice, as well tumors of 4–8 g with large necrotic areas in the case of B16F10 melanomas in C57B6 mice. The ability to target and amplify within small vascularized tumors presents a distinct advantage of *Salmonella typhimurium* as a therapeutic tumor vector.

17.3. Localization By Electron Microscopy of *Salmonella typhimurium* Within Human Lung Carcinoma A549

A mouse was inoculated s.c. in the left shoulder region with $5\times10^6$ A549 cells. After 6 weeks the tumor was palpable and the animal was inoculated i.p. with $3\times10^6$ *Salmonella typhimurium* clone 72, for 66 hours. The animal was sacrificed and a portion of the tumor was homogenized and found to contain $1.6\times10^9$ *Salmonella typhimurium*/g. The central portion of the tumor was prepared for electron microscopy as follows: The portion of the tumor was cut into 1–2 $mm^3$ pieces and fixed in ½ strength Karnovsky's fixative for 6 hours at 4° C., followed by washing in cacodylate buffer overnight. The tumor tissue was post-fixed with 1% $OsO_4$ and 1.5% potassium ferrocyanide in cacodylate buffer for 2 hours and embedded in Spurr's resin. Ultrathin sections were stained with uranyl acetate and lead citrate. They were photographed through a Zeiss 109 electron microscope. It should be noted for comparison purposes that the *S. typhimurium* shown in the electron micrograph of FIG. 12-B appear similar to those shown previously in intestinal epithelial cells following an experimental infection of the mouse, Takeuchi, 1967, Am. J. Pathol. 50:109–1361.

Shown in FIG. 12-B are numerous *Salmonella typhimurium*, denoted by arrows, in extracellular spaces as well as contained within a single cell, possibly a neutrophil, seen in the upper left. Also seen in the field are two unidentified cells that appear to be dying as indicated by the large intracellular space, along with cellular debris.

18. EXAMPLE

Attenuation of *Salmonella typhimurium* By Mutation to Auxotrophy

The studies below demonstrate that the reduced virulence of clone 72 (see, e.g., Section 15.2 above) is due to a Pur⁻phenotype. Further described are analyses of a virulent derivatives of clone 72 that were isolated as additional auxotrophic mutants, expressing in different combinations the phenotypes of Ade⁻, Ilv⁻, Arg⁻, Aro⁻, and Ura⁻.

18.1. Mutation to Auxotrophy

Clone 72 was examined for auxotrophic mutations and was found to have growth requirements for both adenine and vitamin B1, indicating a mutation(s) in the purine biosynthetic pathway (Pur⁻). An experiment was designed to test whether the ade⁻ mutation could account for the observed attenuation of clone 72 described above. Populations of both wild type strain 14028 and clone 72 were mutagenized with UV radiation and nitrosoguanidine as described in Section 7.1. From the population of mutagenized strain 14028, three separate Pur⁻ auxotrophic mutant clones were isolated and designated clones N, Q, and T. From the population of mutagenized clone 72, three separate Pur⁺ revertant clones were isolated and designated clones R, U, and W.

C57B/6 mice were injected i.p. with $2\times10^6$ c.f.u. *Salmonella typhimurium* of each of the strains obtained. The mice were allowed to eat and drink ad libitum and the cages were monitored for dead or moribund mice. Moribund animals (listless, cessation of drinking) were euthanized and counted with the other dead. After 10 or 30 days post-injection with bacteria the surviving animals were euthanized.

The results are shown in Table 20(B).

TABLE 20(B)

SURVIVAL OF C57B6 MICE INJECTED WITH DIFFERENT AUXOTROPHIC MUTANTS OF *SALMONELLA TYPHIMURIUM*

| Strain | Phenotype | Time of Death (Days ± S.D.) | Survivors >10 days | Survivors >30 days |
|---|---|---|---|---|
| 14028 | wild type | 3.0 ± 0.5 | n.a. | n.a. |
| 72 | superinfective, ade⁻ | 5.8 ± 1.4 | n.a. | n.a. |
| R | 72, Pur⁺ | 3.9 ± 0.4 | n.a. | n.a. |
| U | 72, Pur⁺ | 3.9 ± 1.3 | n.a. | n.a. |
| W | 72, Pur⁺ | 4.1 ± 0.9 | n.a. | n.a. |
| T | 14028, Pur⁻ | 6.8 ± 1.5 | n.a. | n.a. |
| N | 14028, Pur⁻ | n.a. | 4/8 | n.d. |
| Q | 14028, Pur⁻ | n.a. | 5/8 | n.d. |
| YS721 | 72, Ilv⁻ | n.a. | 10/11 | 6/11 |
| YS7211 | 72, Ilv⁻, Arg⁻ | n.a. | 8/8 | 7/8 |
| YS7213 | 72, Ilv⁻, Aro⁻ | n.a. | 8/8 | 8/8 |
| YS7212 | 72, Ilv⁻, Ura⁻ | n.a. | 8/8 | 6/8 |

Results are the average ± SD for n = 8–12 animals
n.a., not applicable;
n.d., not done.

As shown in Table 20(B), Clone 72 was less virulent than the wild type strain 14028. However, 3 of 3 Pur⁺ revertants of clone 72 (U, W, and T) expressed virulence similar to 14028. Conversely, 3 of 3 Pur⁻ auxotrophic mutants isolated from strain 14028 (T, N, and Q) were less virulent than either 14028 or clone 72.

Isolation of additional auxotrophs from clone 72 produced even less virulent strains. For example, clone YS721 is an isoleucine-valine requiring (Ilv⁻) derivative of clone 72, and clone YS721 was significantly less virulent than clone 72. Similarly, auxotrophic derivatives of clone YS721 such as clones YS7211 (Arg⁻), YS7212 (Ura⁻), and YS7213 (Aro⁻) were all significantly less virulent than YS721 itself.

18.2. Evidence that the Superinfective Phenotype of Clone 72 Is Genetically Distinct From its Auxotrophic Purine Requirement The various *Salmonella typhimurium* Pur⁻ and Pur⁺ strains described above in Section 18.1 were assayed for their ability to infect human M2 melanoma cells in culture. The in vitro infection assay employed was as described in Section 18.1.

The results are described in Table 20(C).

TABLE 20(C)

INFECTIVITY TOWARD HUMAN M2 MELANOMA CELL IN VITRO BY VARIOUS PURINE MUTANTS OF *SALMONELLA TYPHIMURIUM*

| Strain | Phenotype | Infecting Salmonella/ $10^6$ melanoma cells/15' (±S.D.) | xwild type |
|---|---|---|---|
| 14028 | wild type | $1.0 ± 0.2 \times 10^5$ | 1.0× |
| 72 | superinfective, ade⁻ | $9.8 ± 0.7 \times 10^5$ | 9.8× |
| R | 72, Pur⁺ | $5.9 ± 1.4 \times 10^5$ | 5.9× |
| U | 72, Pur⁺ | $1.1 ± 0.2 \times 10^6$ | 11× |
| W | 72, Pur⁺ | $1.1 ± 0.3 \times 10^6$ | 11× |
| N | 14028, Pur⁻ | $1.9 ± 0.5 \times 10^5$ | 1.9× |
| Q | 14028, Pur⁻ | $1.5 ± 1.0 \times 10^5$ | 1.5× |
| T | 14028, Pur⁻ | $1.1 ± 0.4 \times 10^5$ | 1.5× |

Results are the average ± SD for triplicate infections.
The bacteria were cultured in LB broth to $O.D._{600}$ = .600 prior to their dilution and use in the infection assays.

As shown in Table 20(C), Clone 72 displayed superinfectivity toward human M2 melanoma cells compared to wild type strain 14028. None of the 14028 Pur⁻ derivatives differed significantly in its infectivity from strain 14028 itself, and all of the clone 72 Pur⁺ derivatives expressed superinfectivity similar to clone 72 itself. The results demonstrate that the purine requirement exhibited by clone 72 which accounts for the reduced virulence of clone 72 in mice, is genetically separate from the superinfective phenotype of clone 72. These results demonstrate that neither mutation to nor reversion from purine auxotrophy effects expression of the superinfective phenotype characteristic of clone 72.

18.3. Retention of the Superinfective Phenotype By Attenuated Derivatives of *Salmonella typhimurium* Clone 72

In the experiments below, the infectivity of certain auxotrophic derivatives of clone 72 described above in Section 18.1 was assessed in vitro. The phenotypes of the clones of Salmonella evaluated are shown in Table 20(B) in Section 18.1 above. Infectivity assays described in Section 10.1 were employed.

The results are presented in Table 20(D).

TABLE 20(D)

INFECTIVITY OF *SALMONELLA TYPHIMURIUM* AUXOTROPHS TOWARD HUMAN MELANOMA CELLS IN CULTURE

| Strain | Infecting Salmonella/ $10^6$ melanoma cells/15 min | ×wild type |
| --- | --- | --- |
| 14028 (wild type) | 4.3± × $10^4$ | 1.0× |
| clone 72 | 4.4± × $10^5$ | 10× |
| clone YS721 | 3.2± × $10^5$ | 7.4× |
| clone YS7211 | 2.0± × $10^5$ | 4.7× |
| clone YS7212 | 1.7± × $10^5$ | 4.0× |
| clone YS7213 | 1.3± × $10^3$ | 0.03× |

The results represent the average ± SD for 10–19 separate infections. The bacteria were grown in LB broth to $O.D._{600} = 0.6$ before being diluted prior to their use in the infection assays

*Salmonella typhimurium* clones YS721, YS7211, and YS7212, though each somewhat less infective of M2 melanoma cells than clone 72, were nonetheless superinfective when compared to wild type strain 14028, indicating their partial retention of the superinfective phenotype. In contrast, clone YS7213 (Ade⁻, Ilv⁻, Aro⁻) was found to have greatly reduced infectivity, being about 30-fold less infectious toward M2 melanoma cells than the wild type strain 14028.

18.4. Growth of Pur⁻ and Ura⁻ Mutants of *Salmonella typhimurium* With Nutritional Additives or Extracts of B16F10 Melanoma Tumor extracts were prepared in the following manner: B16F10 melanoma tumor cells (5×$10^5$) were implanted s.c. into 68 week female C57B6 mice. After 3–4 weeks, the mice were sacrificed and the tumors removed aseptically and rapidly frozen, −20° C. A total of 51 g of frozen pooled tumors was thawed at 4° C. and vigorously homogenized in 255 ml (5 vol) H₂O in a capped Virtis tissue homogenizer in the cold for 1 hour. The resulting homogenate was made lot with trichloracetic acid (TCA), placed on ice for 15 minutes, and centrifuged in a Beckman J21 centrifuge at about 20,000×g for 15 minutes at 4° C. Further procedures were conduced at room temperature. The clear, colorless supernatant fraction (300 ml) was retained and extracted by manual shaking for 1 minute with 1 volume (300 ml) anhydrous ether. Between extractions, the mixtures were allowed to settle and the upper phase (containing ether, extracted TCA, as well as ether-soluble compounds from the tumor extract) was removed by aspiration and discarded through approved environmentally-protective procedures. During 5 such extraction cycles, the pH of the water phase rose from a starting value of about pH 1 to a final value of pH 4–5, similar to that of distilled H₂O, indicating that the TCA had been effectively removed. The water phase was bubbled with a stream of nitrogen for about 15 minutes, at which time the odor of ether had disappeared.

The solution was then filtered through a 0.2 micron filter, divided into aliquots and either used directly in the assays herein, or stored at −20° C. for further use.

Wild type strain 14028, and its auxotrophic derivatives clone 72 (Pur⁻, vitamin B1⁻), and YS7212 (Ade⁻, vitamin B1⁻, Ilv⁻, Ura⁻) were grown overnight on a slant in 5 ml Luria broth (LB) at 35° C. The next day 0.1 ml of each culture was diluted into 10 ml of Medium 56 (0.037 M $KH_2PO_4$, 0.06 M $Na_2HPO_4$, 0.020% $MgSO_4$-7H₂O, 0.2% $(NH_4)_2SO_4$, 0.001% $Ca(NO_3)_2$ and 0.00005% $FeSO_4$-7H₂O) supplemented with 0.2 μg/ml vitamin B1, 33 μg/ml adenine, 50 μg/ml uracil, 83 μg/ml isoleucine, 83 μg/ml valine and 0.3% glucose, and grown on a rotor overnight at 37° C. The next day the cultures were collected by centrifugation and resuspended in plain Medium 56 (1 ml culture plus 9 ml Medium 56). Aliquots (0.25 ml) of these suspensions were then added to Medium 56 containing various supplements in the following manner:

A. Medium 56 plus glucose;
B. Medium 56 plus glucose, vitamin B1, adenine, isoleucine, valine, and uracil; and
C. Medium 56 and tumor extract (10%).

The bacteria were placed in a swirling H₂O bath, 37° C., and growth as a function of $OD_{600}$ was followed with a spectrophotometer. The starting optical densities for all of the cultures ranged from 0.005–0.07.

Figure 15A:
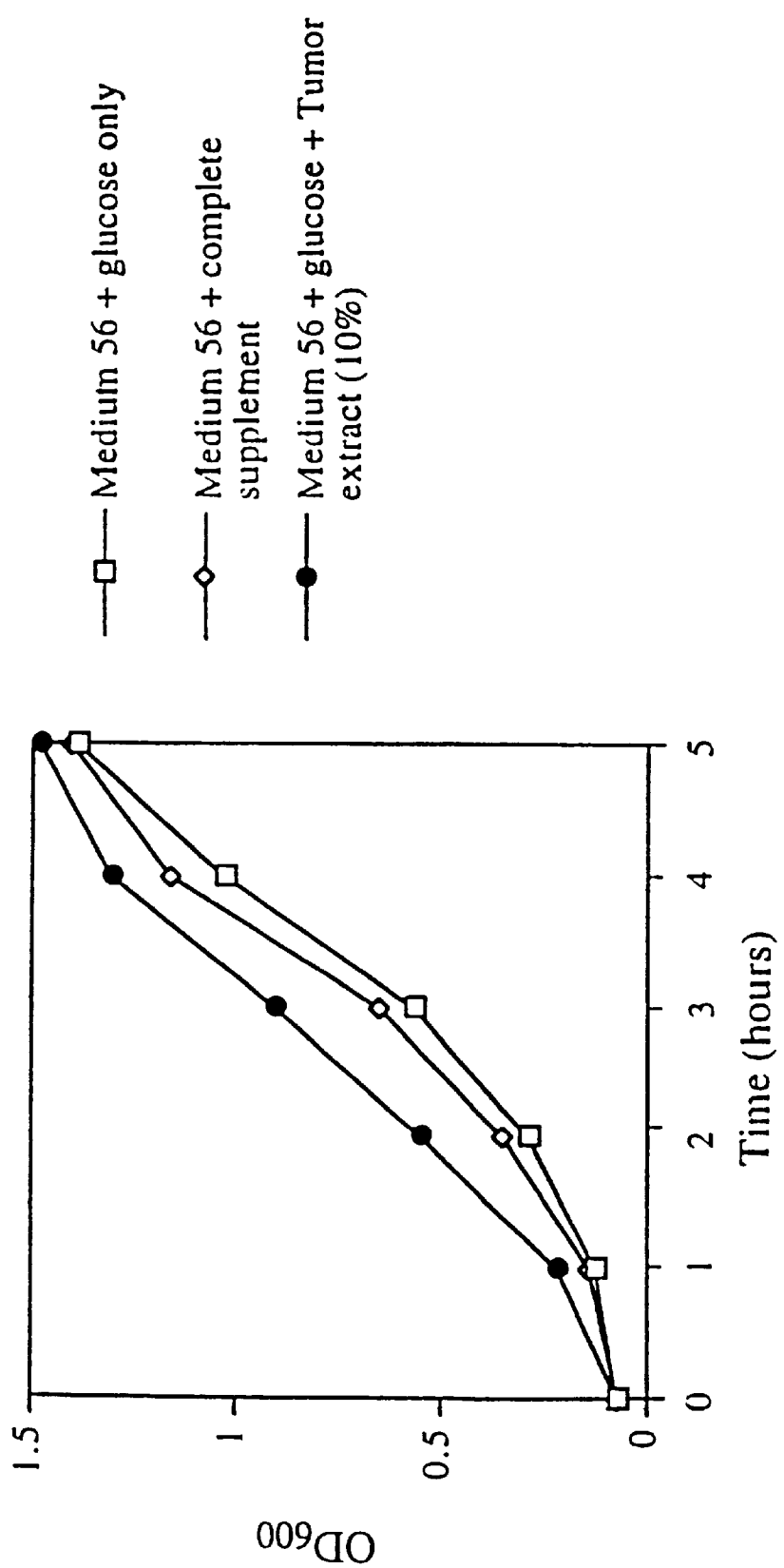
FIGS. 15 A–D.
Figure 15B:
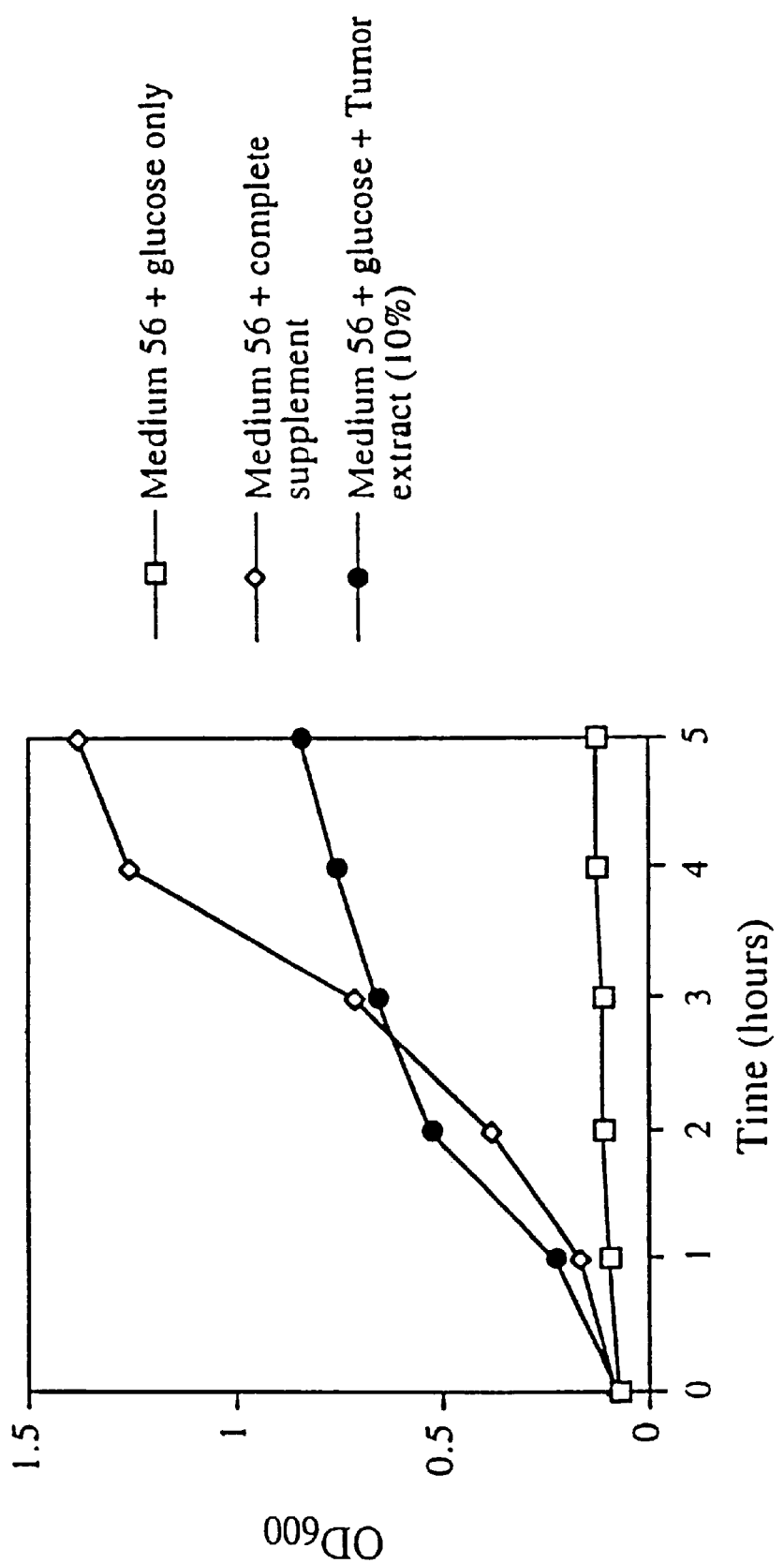
Figure 15C:
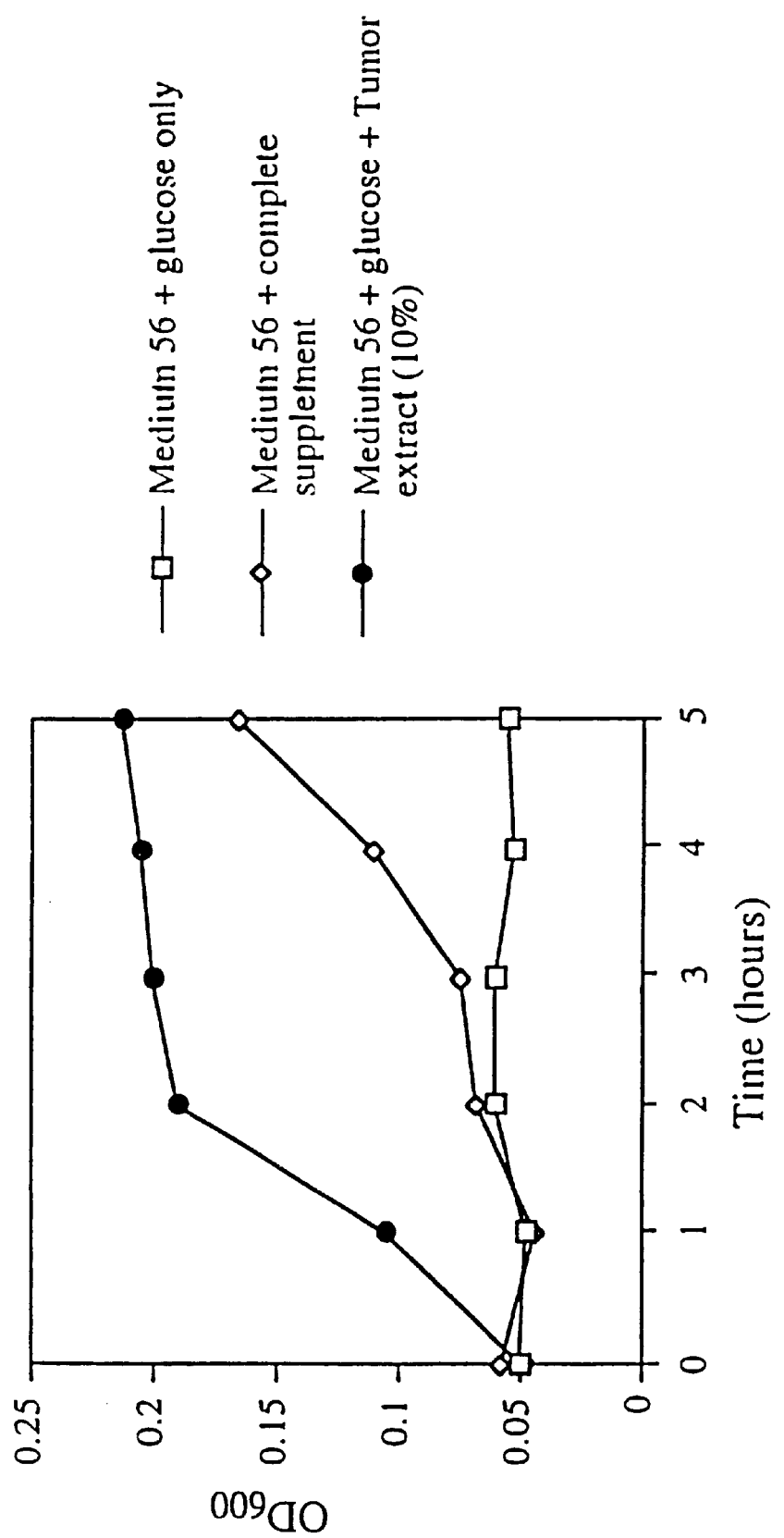
Figure 15D:
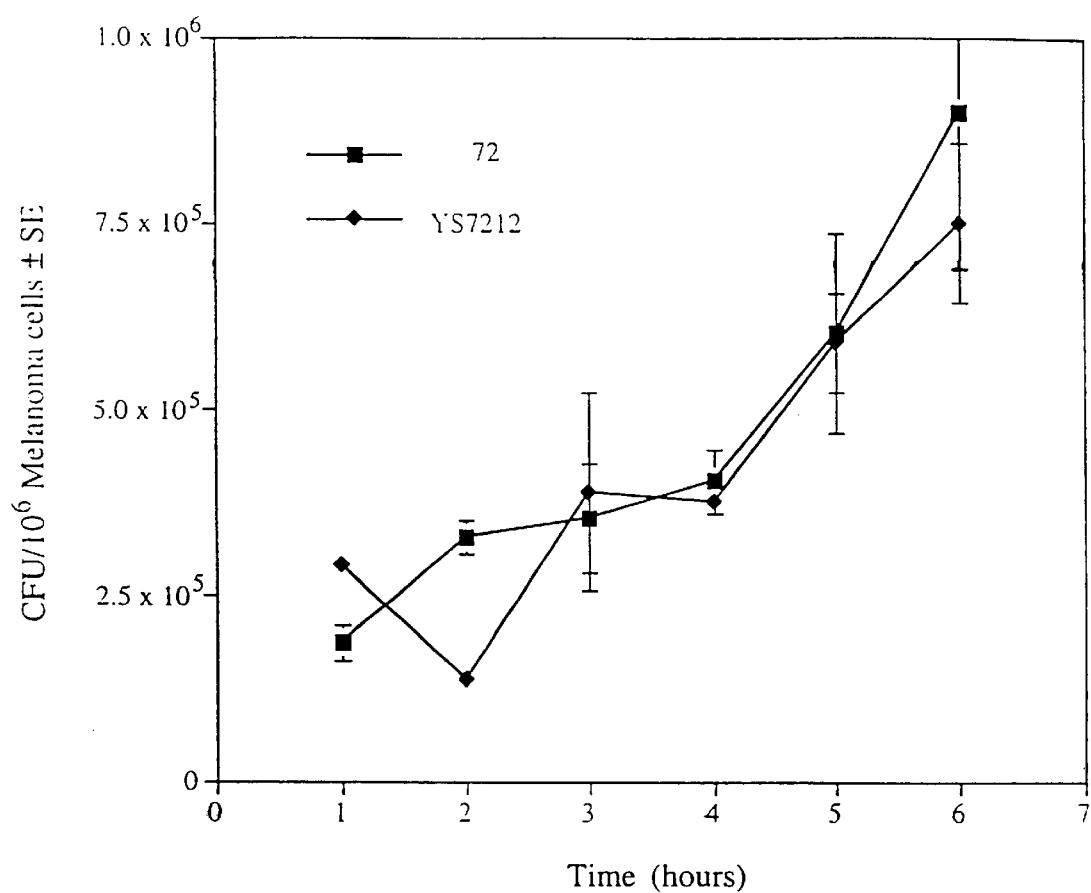
Figure 16A:
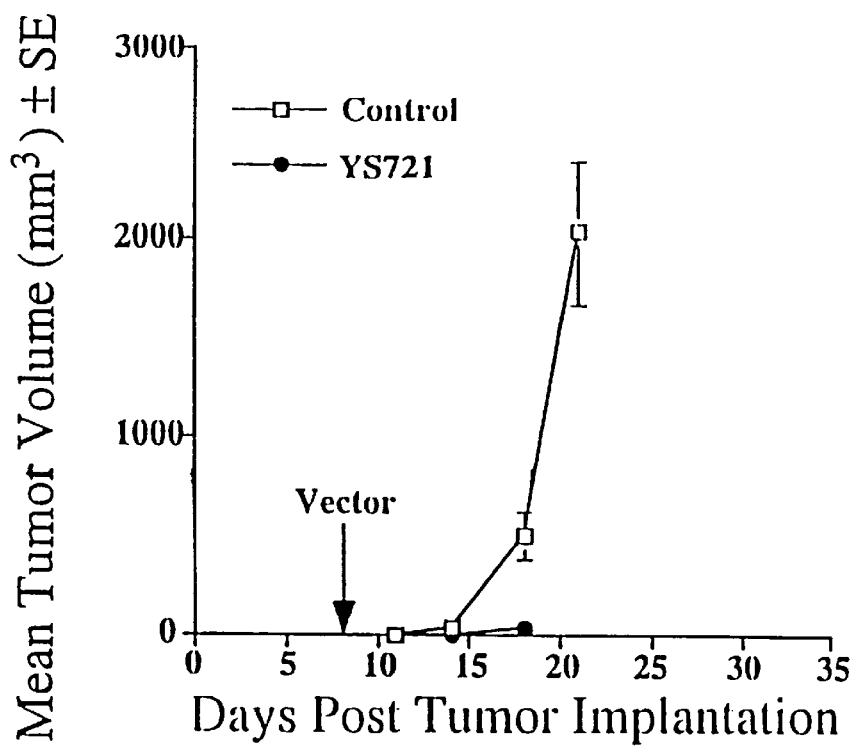
FIGS. 16A–D are graphs showing growth of B16F10 melanomas in C57B6 mice with and without inoculation of *Salmonella typhimurium* strains YS721 (FIG. 16-A); YS7213 (FIG. 16-B); YS7211 (FIG. 16-C); and YS7212 (FIG. 16-D).
Figure 16B:
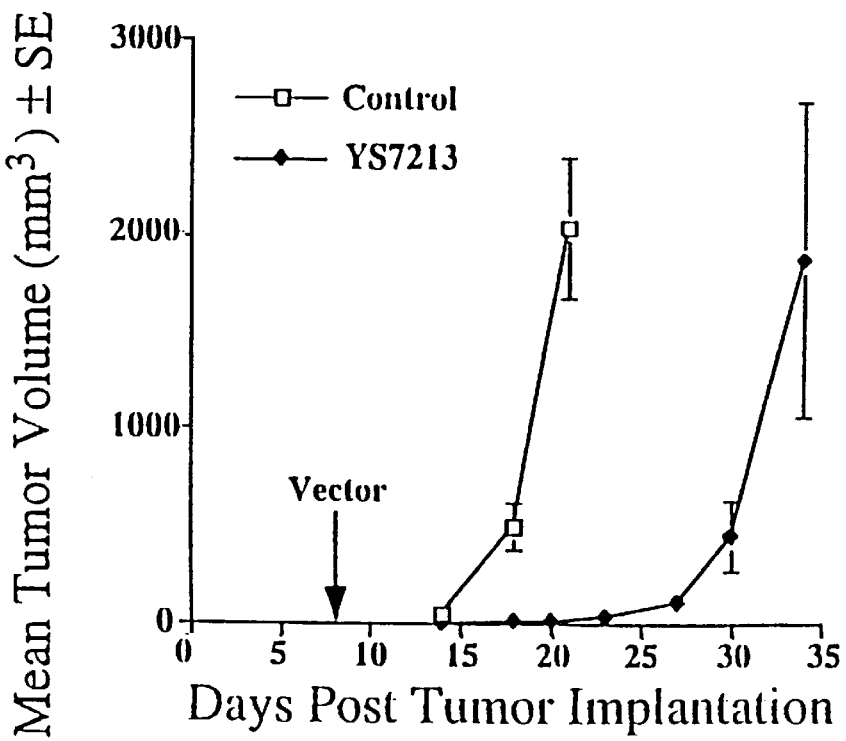
Figure 16C:
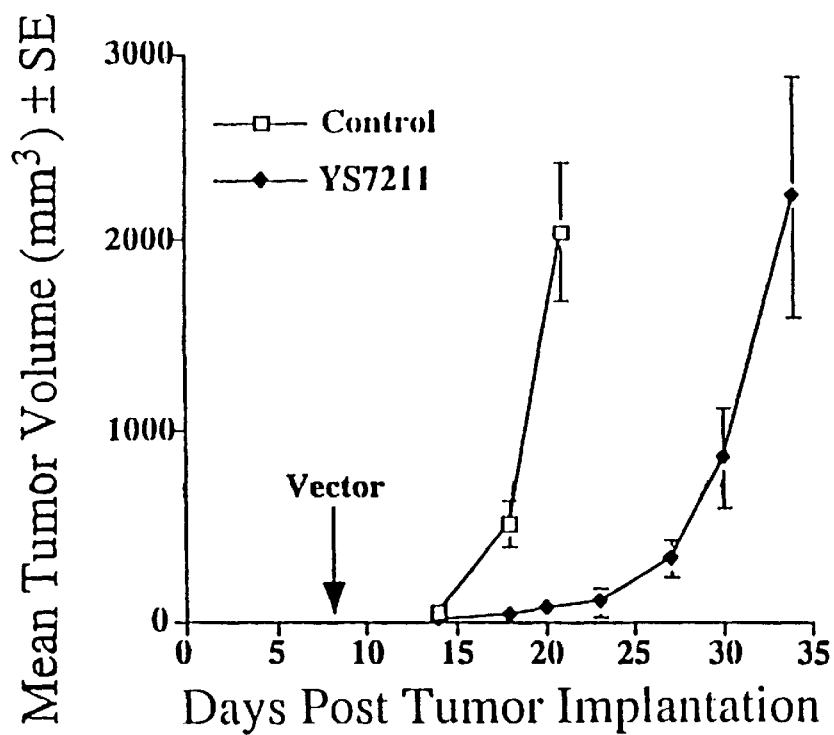
Figure 16D:
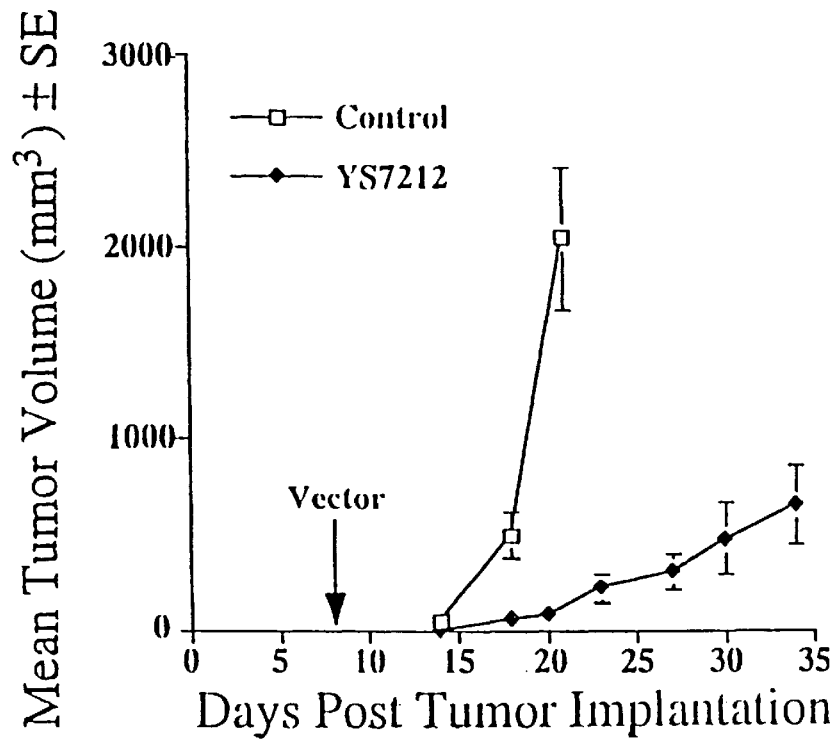

As demonstrated in FIGS. 15A–C, wild type strain 14028 was able to proliferate at about the same rates in all three of the media tested, including the most basic of the three, Medium 56 plus glucose. Unlike the wild type strain, neither clone 72 nor clone YS7212 was able to grow in Medium 56 plus glucose, indicative of their nutritional requirements originally observed through replicated plating on agar. In contrast both clone 72 and clone YS7212 were able to grow in Medium 56 supplemented with 10% tumor extract. Liver extracts prepared in the same manner were also able to support the growth of clones 72 and YS7212.

Although the inventors do not wish to be limited to a specific mechanism of action, since the growth state of auxotrophic strains of Salmonella is dependent upon the availability of nutrients, such auxotrophs would seem to have advantages as tumor vectors since the environment of the tumor could in theory provide such nutrients, for example in necrotic spaces or within actively dividing cells of the tumor. Thus, mutation of organisms such as Salmonella to auxotrophy not only reduces their virulence in vivo but also may provide a potential mechanism for their selective population and amplification within solid tumors.

18.5. Proliferation of Pur⁻ and Ura⁻ Mutants of *Salmonella typhimurium* in Human M2 Melanoma Cells in Culture In this Section it is demonstrated that the internal milieu of cultured M2 melanoma cells also can also supply the auxotrophic requirements of these clones, since both clone 72 and clone YS7212 were able to undergo several rounds of division once they invaded M2 melanoma cells cultured under aerobic conditions.

*Salmonella typhimurium* clones 72 and YS7212 were grown to $O.D._{600}$=0.8, or about $10^9$ c.f.u./ml. The two strains were then added at $10^6$ c.f.u./ml culture media of human M2 melanoma cells as described above in Section 7.2. 15 minutes after infection with Salmonella, the eukaryotic cell cultures were rinsed with fresh medium and medium containing gentamicin (10 µg/ml) was added. At hourly intervals over a 6 hour period, cultures were processed as described in Section 7.2 for quantitation of Salmonella/10⁶ melanoma cells. In addition, control flasks without melanoma cells but with bacteria were processed side-by-side with the experimental flasks containing melanoma cells.

The results are shown in FIG. 15-D. Control flasks with Salmonella but without melanoma cells showed no viable bacteria over the 6 hour period, demonstrating that the wash procedure coupled with gentamicin treatment successfully eliminated all viable bacteria not protected by location within animal cells. In contrast, in the presence of M2 melanoma cells, *Salmonella typhimurium* clones 72 and YS7212 each increased significantly in number over the 6 hour period with doubling times of about 2 hours for each strain. Phase and electron microscope analyses demonstrated that M2 melanoma cells were able to compartmentalize infecting Salmonella within vacuoles. The results indicate that the net rate of growth of Salmonella within the melanoma cells was a steady-state function, reflecting the ability of the melanoma cells to both stimulate growth of the auxotrophs through the supply of nutritional requirements, as well as to suppress the growth of the auxotrophs through anti-bacterial mechanisms.

18.6. Biodistribution of Autotrophic Attenuated Strains of *Salmonella typhimurium* in C57B6 Mice-Bearing B16 Melanoma Tumors These studies demonstrate the ability of clones YS721, YS7213, YS7211 and YS7212 to target tumors and proliferate within the tumor in vivo.

C57B6 6–8 week old female mice were inoculated s.c. (left flank) with 2.5–5.0×10⁵ B16F10 mouse melanoma cells. When the tumors reached about 0.5 g (14–16 days post-tumor inoculum), the animals were further inoculated i.p. with the indicated strains of *S. typhimurium*. The bacterial inoculum was 4×10⁵ cfu/mouse for strains 14028 and 72 and 2–4×10⁶ cfu/mouse for strains YS721, YS7211, YS7212 and YS7213. After 40 and 96 hours post-inoculation of bacteria, the mice were sacrificed, the tumors and livers were removed aseptically, rinsed with sterile NaCl (0.9%), weighed, and homogenized in LB broth at a ratio of 5:1 (vol:tumor wt). Bacteria were quantitated by plating the homogenates onto LB plates, incubating overnight at 37° C., and counting bacterial colonies. The results presented in Table 20(E) represent the average±SD for n=4–7 animals.

TABLE 20(E)

BIODISTRIBUTION OF WILD TYPE AND ATTENUATED STRAINS OF *SALMONELLA TYPHIMURIUM* IN C57B6 MICE-BEARING B16 MELANOMA TUMORS

| Strain | Salmonella/g tissue: Tumor | Liver | Tumor:Liver |
|---|---|---|---|
| A. 40 hrs post-inoculation of bacteria | | | |
| 14028 | 6.5 ± 6.8 × 10⁹ | 2.4 ± 2.8 × 10⁷ | 270:1 |
| 72 | 1.7 ± 1.2 × 10⁹ | 1.9 ± 2.3 × 10⁵ | 9000:1 |
| YS721 | 8.7 ± 3.1 × 10⁸ | 4.2 ± 3.6 × 10⁶ | 210:1 |
| YS7211 | 3.3 ± 3.0 × 10⁷ | 8.1 ± 8.4 × 10⁵ | 41:1 |
| YS7212 | 3.9 ± 7.3 × 10⁷ | 1.1 ± 0.8 × 10⁶ | 35:1 |
| YS7213 | 1.5 ± 2.8 × 10⁸ | 4.0 ± 3.1 × 10⁵ | 375:1 |
| B. 96 hrs post-inoculation with bacteria | | | |
| 14028 | moribund/dead | | |
| 72 | moribund/dead | | |
| YS721 | 3.2 ± 1.5 × 10⁹ | 4.7 ± 6.9 × 10⁶ | 680:1 |
| YS7211 | 1.6 ± 2.2 × 10⁹ | 6.3 ± 9.9 × 10⁶ | 253:1 |
| YS7212 | 1.1 ± 7.4 × 10⁹ | 5.1 ± 8.6 × 10⁵ | 2200:1 |
| YS7213 | 1.3 ± 2.5 × 10⁹ | 2.2 ± 6.9 × 10⁵ | 5900:1 |

Each of the strains tested was able to target the tumor tissue and replicate to varying degrees within the tumor, as evidenced by the finding that in all cases the tumors contained 10–1000 times more *Salmonella typhimurium* than were first inoculated. Further, in all cases the tumor:liver ratio of bacteria/g tissue was at least 35:1 and in some cases approached 10⁴. The tumors analyzed in the studies presented in Table 20(E) ranged in weights from 0.5–2.0 g. Of all the conditions and strains tested, clone 72 exhibited the highest tumor:liver ratio 40 hours post inoculation. Further, *Salmonella typhimurium*, strain 14028, as well as clone 72 and its derivatives were also able to target and amplify within larger B16P10 melanoma tumors of, for example, 4–8 g. In addition, as shown in Section 10.3.2 and Table 12A, clone 72 can target and amplify within human solid tumors as small as 40 mg.

However, both clone 72 and the wild type strain 14028 were highly virulent toward C57B6 mice, especially mice bearing tumors. For example, C57B/6 mice bearing B16F10 melanomas injected with strains 1428 and 72 had average survival times of 2.1±0.4 days (n=6) and 4.7±0.5 days (n=9) post-inoculation of bacteria respectively. The biodistribution of these strains was thus not measured at 96 hours. Likewise, clone YS721, though attenuated compared to 14028 and clone 72, was nonetheless virulent in melanoma-bearing mice. For example, B16F10 melanoma-bearing C57B6 mice injected with clone YS721 had an average survival time of 8.1±0.2 days (n=11). Salmonella clones YS7211, YS7212 and YS7213, the least virulent of those examined, each displayed densities of greater than 10⁹ cfu bacteria/g tumor 96 hrs post-inoculation with tumor:liver ratios of 253:1, 2200:1, and 5900:1 respectively.

18.7. Phenotypic Stability Following Incubation of *Salmonella typhimurium* Auxotrophs in Tumor-Bearing Mice Genetic reversion of an auxotrophic phenotype could in theory result in an increase in virulence of the previously attenuated bacteria. Therefore, the stabilities of the auxotrophic phenotypes of the strains YS7211, YS7212 and YS7213 were tested following incubation of the bacteria in tumor-bearing mice.

*Salmonella typhimurium* obtained from the homogenates of livers and tumors of animals 40 hours post-inoculation of either YS7211, YS7212 or YS7213 were picked from LB plates and replicate plated onto minimal media agar plates supplemented with nutritional additives in different combinations. The supplements were isoleucine, valine, adenine/vitamin B1, arginine, uracil, aromatic amino acids, and glucose. For each of the three strains, 50/50 of the bacterial clones recovered from the tumor and liver homogenates displayed the expected phenotypes of the strain originally inoculated, indicating that in this experiment the strains were genetically stable enough not to revert substantially under the conditions tested.

However, it should be noted that the auxotrophic strains employed were not absolutely stable throughout these studies. In some cases genetic revertants were observed, most notably in the YS7211 strain wherein revertants from Arg⁻ to Arg⁺ were observed. For example, in a tumor-bearing mouse inoculated 96 hours earlier with clone YS7211 bearing a thymidine kinase-containing plasmid, 50 out of 50 bacteria isolated from the liver were found to be Pur⁻, Ilv⁻ and Arg⁺, indicating that reversion and selective growth of the reverted organisms had occurred within the mouse. The finding that the auxotrophic phenotypes of clones YS7211, YS7212 and YS7213 were relatively stable in mice was supported by the long term survival of mice inoculated with these strains.

18.8. Suppression of Tumor Growth and Increased Survival of C57B6 Tumor-Bearing Mice Inoculated With Auxotrophic Mutants of *Salmonella typhimurium*

C57B6 female mice, 5–7 weeks old, were inoculated s.c. in the left shoulder region with $5 \times 10^5$ B16F10 melanoma cells grown in culture. On the 8th day following inoculation of tumor cells, the mice were further inoculated i.p. with $2-4 \times 10^6$ c.f.u. of *Salmonella typhimurium* strains YS721, YS7211, YS7212 or YS7213. Tumor growth was assessed with periodic caliper measurements of tumor length, width and height, and computed as tumor volume in mm³. Results of tumor growth, shown in FIGS. 16A–D represent the averages±SD for 5 animals/group with 5/5 animals surviving. After the point at which one or more animals died within a group, the average tumor sizes of the surviving animals were no longer shown when the data were plotted as shown in FIGS. 16A–D.

All tumor measurements were stopped after 33 days post implantation of tumor cells, even though 5/5: tumor-bearing animals treated with clone YS7211 were still alive at this time. The animals were allowed to eat and drink ad libitum. Twenty-three days (Experiment #1) or 10 days (Experiment #2) following inoculation of bacteria, both control and bacteria treated mice were given Baytril™ (enrofloxacin, 0.2 mg/ml drinking water) and maintained on this antibiotic for a total of 2 weeks. In Experiment #1 the times at which the mice became moribund (listless, cessation of drinking) or died, were noted. The results are presented in Table 20(F) as the average survival±SD for the conditions tested. In Experiment #2 animals were sacrificed when the tumor reached 4 g and listed with the other dead as described in Experiment #1. The two different methods for assessing survival accounted for a somewhat shorter survival time for control animals in Experiment #2 (26 days) as compared to Experiment #1 (28 days).

TABLE 20(F)

SURVIVAL OF B16F10 MELANOMA-BEARING C57B6 MICE INOCULATED WITH *SALMONELLA TYPHIMURIUM*

| Strain | | Time of death post tumor cell inoculation: (Days ± SD) | Treated/Control (T/C) |
|---|---|---|---|
| Control (no bacteria) | Expt 1 | 28 ± 2 | 1.0 |
| | 2 | 26 ± 3 | 1.0 |
| YS7211 | 1 | 36 ± 9 | 1.3 |
| | 2 | 41 ± 10 | 1.6 |
| YS7213 | 1 | 36 ± 5 | 1.3 |
| | 2 | 38 ± 6 | 1.5 |
| YS7212 | 1 | 51 ± 7 | 1.8 |
| | 2 | 55 ± 3 | 2.1 |

The results represent the average ± SD for 6 animals.

FIGS. 16A–D shows the average±SD tumor volumes (mm³) versus time post inoculation of $5 \times 10^5$ B16F10 melanoma cells s.c. into C57B/6 mice. All four clones of Salmonella, namely clones YS721, YS7211, YS7212 and YS7213, elicited suppression of tumor growth in the animals. Clone YS721, attenuated through Ade⁻ and Ilv⁻ auxotrophy, was nonetheless toxic to tumor-bearing mice and resulted in no prolongation of survival compared to control tumor-bearing animals receiving no bacteria. Whereas the death of control animals was clearly due to very large tumor masses (4–8 g), the death of tumor-bearing animals inoculated with clone YS721 appeared to be a result of bacterial toxicity since the tumor burden in these animals was quite small and not life-threatening in itself. The tumors ranged from non-palpable to less than 0.5 g at the time of death.

In contrast, treatment of tumor-bearing mice with clone YS7211, YS7212 and YS7213, each less virulent than clone YS721, resulted in significant enhancement of survival in addition to suppression of tumor growth. The degree of suppression of tumor growth by the individual Salmonella clones, as seen in FIGS. 16A–D, correlated with their abilities to elicit enhanced survival, as seen in Table 20(F). The average time for tumors to reach 1 g (1000 mm³) was about 18 days for control animals, 31 days for animals treated either with YS7213 and YS7211 and 45 days (extrapolated) for YS7212. This corresponded to average survival times for 26 days for control tumor-bearing animals, compared to 38, 41, and 55 days for animals treated with clones YS7213, YS7211 and YS7212.

Thus, among the attenuated strain of Salmonella tested, the order of efficacy for suppression of tumor growth and prolongation of survival was YS7212>YS7211>YS7213. Earlier treatment with an antibiotic, enrofloxacin, i.e., 10 days as compared to 23 days post-inoculation of bacteria, increased the survival time for tumor-bearing animals inoculated with Salmonella, but not that of control animals.

18.9. Anti-tumor Activity of Auxotrophic *Salmonella typhimurium* Expressing Cytosine Deaminase Experimental metastasis model of B16F10was set up by injecting $1 \times 10^5$ cells into C57B/6 mice via the lateral tail vein on Day 0. Aliquots of 0.2 ml bacterial suspension of YS7212 carrying the cytosine deaminase expression construct (see FIG. 4E for the CD construct) (approximately $1 \times 10^7$ CFU/ml) were injected intraperitoneally into mice on Day 5. 5-Flourocytosine (5-FC), at 0.4 ml aliquots dissolved in PBS at 10 mg/ml (final dose: 200 mg/kg), was injected into mice intraperitoneally on Day 7. Death of animals was recorded daily. Results are presented in FIG. 17.

Figure 17:
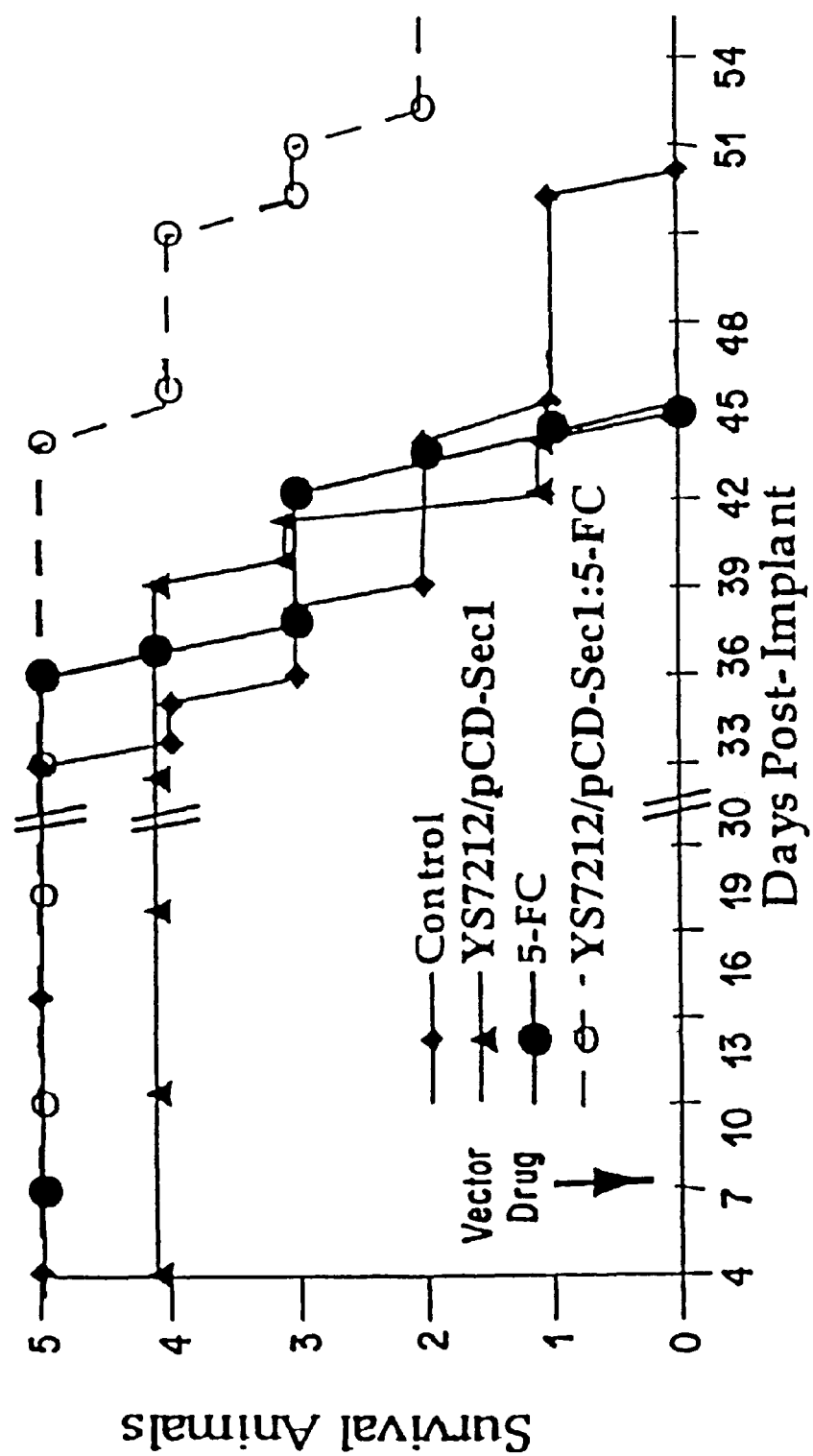
FIG. 17 is a graph showing that combination of CD and 5-fluorocytosine prolong the survival of animals bearing B16F10 lung metastases when the animals are infected with a tumor-specific vector carrying the cytosine deaminase expression construct YS7212/pCD-Sec1.

FIG. 17 clearly demonstrates that combination of CD and 5-fluorocytosine prolong the survival Salmonella expressing animals bearing B16F10 lung metastases.

19. EXAMPLE

Attenuation of *Salmonella typhimurium* Through Mutation in Lipoplysaccharide Biosynthesis Several mutant strains of *Salmonella typhimurium* and *E. coli* have been isolated with genetic and enzymatic lesions in the LPS pathway (Raetz, 1993, J. Bacteriol. 175:5745–5753). One such mutant, the firA⁻ mutation is within the gene that encodes the enzyme UDP-3-O(R-30 hydroxymyristoyl)-glycocyamine N-acyltransferase, that regulates the third step in endotoxin biosynthesis (Kelley et al., 1993, J. Biol. Chem. 268:19866–19874). *Salmonella typhimurium* and *E. coli* strains bearing this type of mutation produce a lipid A that differs from wild type lipid A in that it contains a seventh fatty acid, a hexadecanoic acid (Roy and Coleman, 1994, J. Bacteriol. 176:1639–1646) and has decreased lipid A 4' kinase activity.

A firA⁻ mutant was investigated for its ability to induce TNFα production by human monocytes as well as its ability to target solid tumors in mice.

19.1. Ability of *Salmonella typhimurium* firA⁻ to Induce TNF-α Production By Human Blood Monocytes

*Salmonella typhimurium* strain SH5014 and its firA⁻ derivative SH7622 are described in Hirvas et al., 1991, EMBO J. 10:1017–1023. The genotypes of these strains are as follows:

strain SH5014 ilv-1178 thr-914 his-6116 metA22 metE551 trpB2 xyl-404 H1-b H2-e,n,x flaA66 rpsL120 rfaJ4041;

strain SH7622 ilv-1178 thr-914 his-6116 metA22 metE551 trpB2 xyl-404 H1-b H2-e,n,x flaA66 rpsL120 rfaJ4041, ssc-1(firA$^{ts}$).

A derivative of *Salmonella typhimurium* firA⁻ strain SH7622 was picked, designated SH7622-64, and used as the firA⁻ strain for the experiments in this section as well as in Section 19.2 below. SH7622-64 was selected for its super-sensitivity to the antibiotic novobiocin and temperature-sensitive growth, characteristics of the firA⁻ SH7622 strain.

LPS was extracted from *Salmonella typhimurium* strain 14028 and its derivatives clone 72, clone YS7212, and clone YS7213; as well as strain SH5014 and its firA⁻ derivative, clone SH7622-64, as follows: The bacteria were grown in 500 ml LB broth to $O.D._{.600}$=0.9 or about $2 \times 10^9$ cfu/ml. They were collected by centrifugation, and the pellets, containing about $10^9$ cfu/ml. They were collected by centrifugation, and the pellets, containing $10^{12}$ bacteria, were drained and stored frozen at $-20°$ C. To extract LPS, the pellets were resuspended in 18.3 ml $H_2O$, and 15 ml redistilled phenol was added ($H_2O$:phenol, 55:45, vol/vol). The mixtures were placed in a shaking water bath at 69–70° C., for 1 hour producing a monophasic mixture, and then cooled on ice. On cooling the mixture separated into a phenol phase containing mainly proteins, and a water phase containing lipopolysaccharide and nucleic acid (Galanos, C., Luderitz, O., and Westphal, O., 1969). The water phase was lyophilized to dryness and the white fluffy lyophilized material was used as the source of LPS. The LPS was weighed and dissolved in $H_2O$ at 1 mg/ml, as stock for dilution in the incubations with human macrophages described below.

Human macrophages were prepared as follows and all procedures were at room temperature: Blood (60 ml) was collected from a healthy human volunteer into a heparinized syringe. The blood was layered in 7 ml aliquots over 4 ml of Isolymph™ (density—1.077 g/ml; 9.0 g sodium diatrizoate and 5.7 g Ficoll 400™/100 ml $H_2O$; Pharmacia Fine Chemicals, A.B. Uppsala, Sweden) in 15 ml Corning Plastic Centrifuge tubes, centrifuged at 2000×g for 45 minutes. The red blood cells pelleted through the Isolymph™, neutrophils and other cells sedimented in a discrete band above this interface, and above the lymphocyte/macrophage band was serum, visible by its yellow color. The serum from each tube was removed by pipette, pooled in a total volume of about 30 ml and saved for supplementation into the culture media as described below. The lymphocyte/macrophage bands were pooled in a total volume of about 15 ml diluted with 40 ml RPMI 1640 culture medium, and centrifuged at 1000×g for 5 minutes. The cloudy supernatant was discarded and about 0.2 ml of pelleted white cells was obtained. The cells were resuspended with 50 ml RPMI 1640 culture medium supplemented with 15% human serum (described above), penicillin (100 units/ml) and streptomycin (100 μg/ml). The recovery of viable lymphocytes and macrophages from 60 ml whole blood was determined by hemocytometer counting to be about $7 \times 10^7$ cells. Together the cells, lymphocytes and monocytes were distributed into 24 well Corning Tissue Culture Plates at 0.5 ml/well, and incubated in a gassed humidified incubator at 37° C. for 15 hours.

The next day the cultures were rinsed twice with serum-free RPMI 1640 containing antibiotics. Between each rinse, the cultures were incubated about 1 hour in the 37° C. incubator to facilitate removal of lymphocytes and other non-adherent cells. Adherent cells were found to be mostly, if not all derived from blood monocytes, i.e., macrophages that had differentiated from their blood monocyte state by virtue of attachment to the culture dish. For example, in a histochemical assay to determine the percentage of macrophages in the adherent population of cells 48 hours post-plating into culture, the population was found to be essentially 100% positive for expression of the enzyme non-specific esterase, a marker commonly used to distinguish monocytes and macrophages from lymphocytes and other cell types. Results indicated that most if not all of the cells employed in the LPS challenge described below were of monocyte origin.

Figure 18:
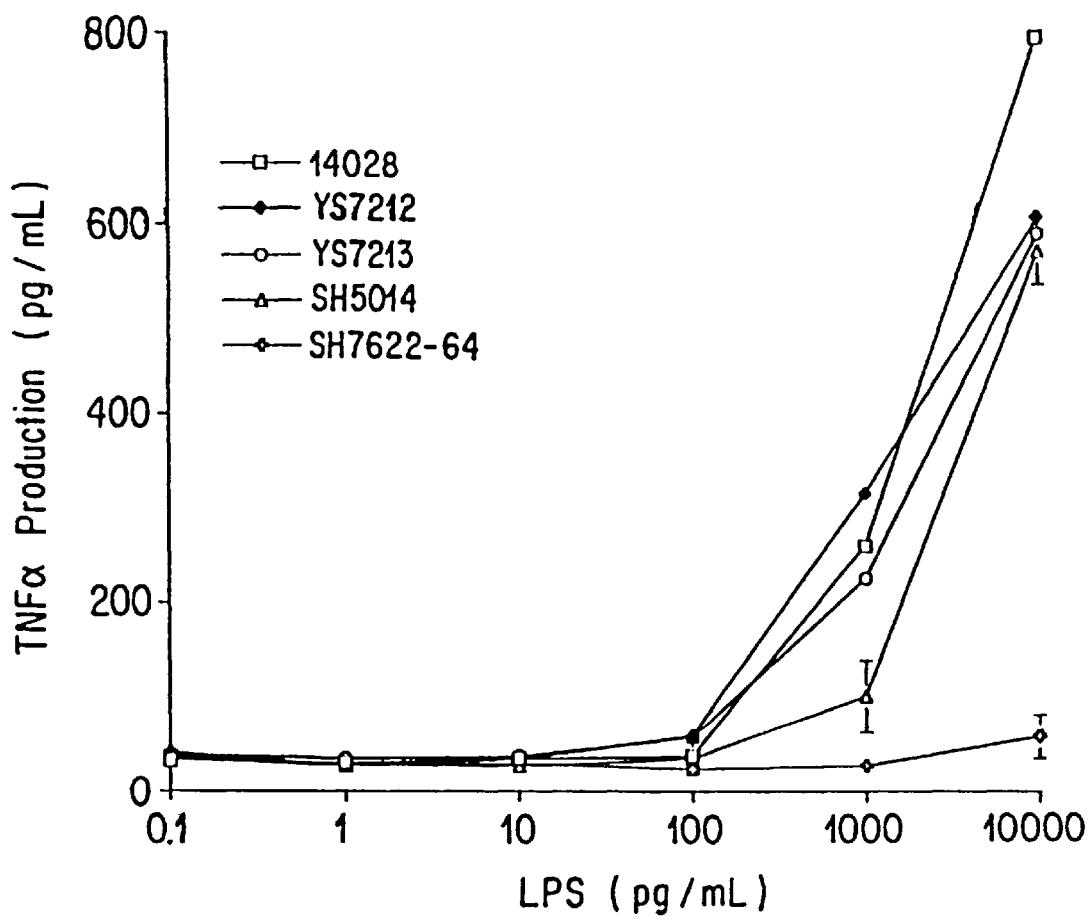
FIG. 18 is a graph showing TNF-α production by human macrophages incubated with lipopolysaccharide isolated from wild type and attenuated strains of *Salmonella typhimurium*.

After the second rinse described above, serum-free, antibiotic containing RPMI 1640 supplemented with LPS at the concentrations indicated was added to the cells, and the cultures were placed in a gassed, humidified incubator at 37° C. overnight. After 20 hours, the well plate cultures were centrifuged in a Beckman GS-15 centrifuge at 8000×g for 10 minutes, and the supernatants were removed and assayed for TNF-α content using the QUANTIKINE™ Human TNF-α Immunoassay Kit #DTA50 (R&D Systems, Minneapolis, Minn.). TNF-α production as pg/ml by human macrophages is plotted as a function of pg/ml bacterial LPS added to the culture medium and shown in FIG. 18.

Strain 14028 and its derivatives clone 72, clone YS7212, and clone YS7213, as well as strain SH5014, all induced TNF-α production by human macrophages at concentrations of LPS in a dose-dependent fashion. Concentrations of LPS from each of these strains as low as 100 pg/ml (0.1 ng/ml) were stimulatory to TNF-α production, and increasingly stimulatory at concentrations of $10^3$ pg/ml and $10^4$ pg/ml, inducing TNF-α production by macrophages to levels of 600–800 pg/ml. The levels of TNF-α induced by the LPS were similar to the circulating levels of TNF-α found in patients with septic shock syndrome as well as in human volunteers injected with *E. coli* LPS (Morrison et al., 1994, ASM News 60:479–484). In contrast, LPS from firA⁻strain SH7622–64 was far less stimulatory to TNF-α production by the macrophages, and was detected only at concentrations of $10^4$ pg/ml. Thus, on a dose response comparison, LPS from strain SH7622-64 was only about 1% as effective in stimulating macrophage TNF-α production when compared to LPS from the firA⁺ parental strain SH5014. Furthermore, the results demonstrate that strains YS7212 and YS7213 each produced LPS similar to wild type strain 14028 LPS, as assessed by stimulation of human macrophages.

19.2. Tumor Targeting By *Salmonella typhimurium* Bearing the firA⁻ Mutation

M27 mouse lung tumor cells or B16F10 mouse melanoma cells ($5 \times 10^5$) were implanted s.c. in C57B6 mice. When the tumors were palpable, SH7622-64 grown in LB broth at 37° C. to a density of about $10^9$ cfu/ml ($OD_{600}$=0.8). Aliquots of $5-10 \times 10^6$ cfu were removed and inoculated into tumor bearing mice. At 48 hrs (M27 lung) and 96 hrs (B16F10 melanoma) post-inoculation of bacteria the animals were sacrificed, the tumors and livers removed, weighed and homogenized in LB broth at a ratio of 5 ml/g tissue. Homogenates were quantitated for bacteria by serial dilutions on LB agar plates. Results are presented in Table 20(G).

TABLE 20(G)

TUMOR LOCATION BY *SALMONELLA TYPHIMURIUM* BEARING THE firA⁻ MUTATION FOR LIPOPOLYSACCHARIDE BIOSYNTHESIS

| Primary Tumor | Salmonella/g tissue: | | |
|---|---|---|---|
| | Tumor | Liver | Tumor:Liver |
| M27 lung | $2.9 \times 10^6$ | -0- | n.a. |
| B16 | $3.2 \times 10^6$ | $1 \times 10^2$ | 3200:1 |

The results are derived from single anlmals.

As shown in Table 20(G), strain SH7622-64 was able to locate within both the B16F10 melanoma and the M27 lung tumors when inoculated i.p. into mice. These results, in combination with those in Section 19.1 which show that LPS from this particular firA⁻ strain was greatly suppressed in its ability to induce TNF-α in human macrophages, demonstrate that Salmonella attenuated through a mutation in endotoxin biosynthesis can be useful as tumor vectors in vivo.

20. EXAMPLE

Tumor-Specific Accumulation of Clones YS721 and YS7211 in Murine Lewis Lung Carcinoma This example demonstrates that auxotrophic mutant Salmonella clones YS721 and YS7211 locate to lung carcinoma.

The experimental model of the Lewis lung carcinoma was set up by injecting $5 \times 10^5$ cells into C57B/6 mice subcutaneously on Day 0. Aliquots of 0.2 ml bacterial suspension (approximately $1 \times 10^7$ CFU/ml) were injected intraperitoneally into mice on Day 14. On Day 16, the tumors and livers were harvested and homogenized and bacterial counts determined by plating serial dilutions. Results of the relative distribution are shown in Table 20(H).

TABLE 20(H)

TUMOR SPECIFIC ACCUMULATION OF CLONES YS721 and YS721 1 IN MICE

| Strain | No. pathogens/ g Liver | No. pathogens/ g Tumor | Ratio:tumor/liver |
|---|---|---|---|
| YS721 | $9.8 \times 10^6$ | $4.7 \times 10^{10}$ | $4.8 \times 10^3$ |
| | $4.3 \times 10^5$ | $3.2 \times 10^{10}$ | $7.3 \times 10^4$ |
| | $1.1 \times 10^6$ | $1.4 \times 10^9$ | $1.3 \times 10^3$ |
| | $1.6 \times 10^6$ | $1.0 \times 10^{12}$ | $6.2 \times 10^6$ |
| | $3.0 \times 10^4$ | $2.3 \times 10^9$ | $7.7 \times 10^4$ |
| YS7211 | $1.4 \times 10^4$ | $2.6 \times 10^{10}$ | $1.9 \times 10^6$ |
| | $1.9 \times 10^5$ | $2.7 \times 10^6$ | $1.4 \times 10^3$ |
| | $2.3 \times 10^5$ | $6.0 \times 10^{11}$ | $2.6 \times 10^6$ |
| | $1.0 \times 10^6$ | $5.0 \times 10^{11}$ | $5.0 \times 10^5$ |

Extremely high levels of bacteria were localized to these tumors, as well as others indicating that the auxotrophic mutations retain tumor specific accumulation of bacteria for a spectrum of tumor models.

21. EXAMPLE

Treatment of B16F10 Melanoma Metastatic Tumors

Metastases constitute one of the major problems for treatment of solid tumors. While larger tumors can be detected and removed surgically, smaller metastases. constitute the untreated reservoir which is frequently the cause of death. Therefore, an effective cancer therapeutic should be effective against metastatic tumors.

An experimental metastasis model of B16F10 was set up by injecting $1 \times 10^5$ CELLS into C57B/6 mice via the lateral tail vein on Day 0. Aliquots of 0.2 ml YS7211/p5-3 and YS7212/p5-3 (YS7211 and YS7212 each carrying the HSV thymidine kinase expression plasmid) bacterial suspensions (approximately $1 \times 10^7$ CFU/ml) were injected intraperitoneally into mice on Day 5. Ganciclovir, at 0.1 ML aliquots dissolved in PBS at 22 mg/ml (final dose: 100 mg/kg), was injected into mice intraperitoneally on Day 7. Tumor progression was monitored by periodic sacrifice and examination of the lungs. At day 28, all the animals were sacrificed and the normal and tumor-bearing lungs weighted.

Figure 19:
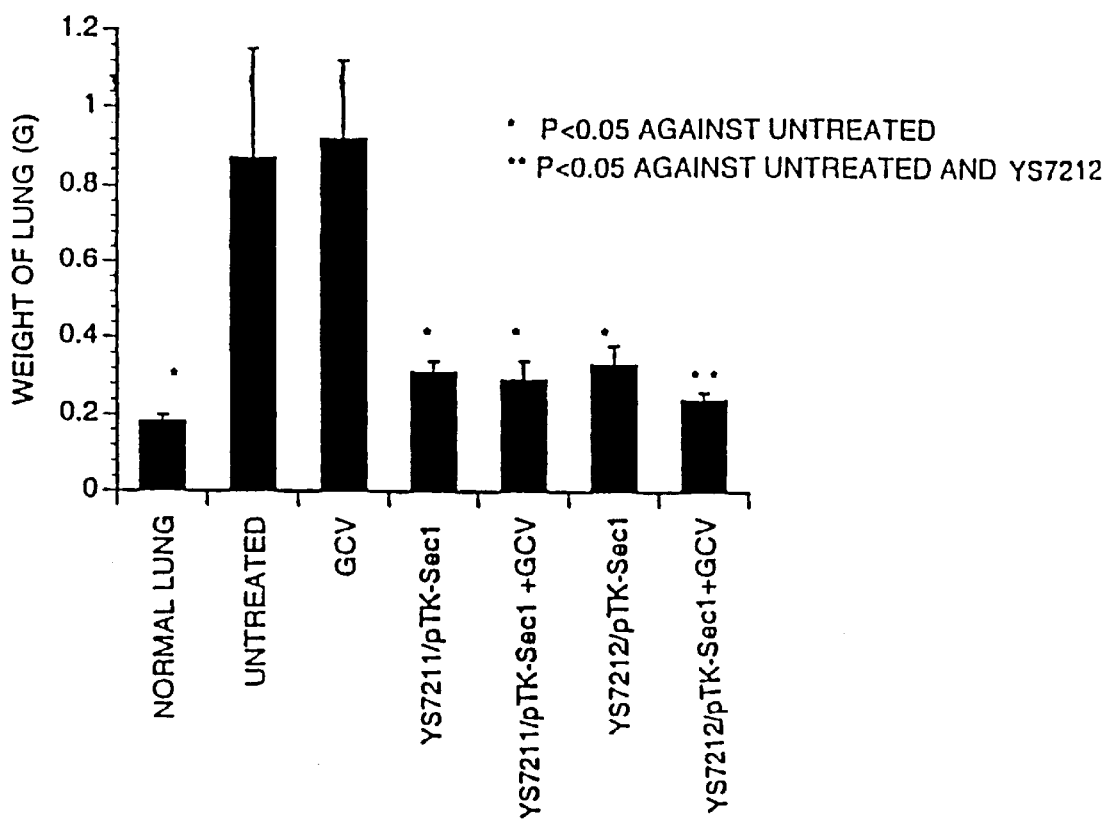
FIG. 19 is a bar graph demonstrating the effect of clones YS7211 and YS7212 expressing the HSV thymidine kinase gene, YS7211/p5-3 and YS7212/p5-3, respectively, on mice bearing metastatic B16F10 tumors with or without ganciclovir treatment.

FIG. 19 clearly demonstrates that animals inoculated with YS7212 carrying the HSV thymidine kinase gene (YS7212/p5-3) and further treated with GCV show reductions in the number and extent of B16F10 lung metastases.

22. EXAMPLE

Diagnosis of Tissue Biopsies For Melanoma Using *Salmonella typhimurium*

Diagnosis of melanoma according to the methods of the present invention can be performed using, for example, *Salmonella typhimurium* as follows: A portion of a biopsied specimen suspected of melanoma is minced with scissors in tris-buffered saline (TBS) and then incubated in $Ca^{++}/Mg^{++}$-free saline containing trypsin, collagenase, and EDTA (Sigma Chemicals) for 60 minutes at 37° C. to dissociate the tissue into individual cells. The cells are then rinsed free of the dissociation enzymes by centrifugation. The cells are resuspended in 1 ml DMEM/10% FBS and added to a 24 well Corning tissue culture chamber containing cover slips in the wells. The cells are then incubated in a gassed (5% $CO_2$/95% air) humidified incubator for 3 hours at 37° C. to allow for attachment to the cover slip.

After attachment of the biopsied cells is achieved, an attenuated, super-infective, melanoma-specific strain of *Salmonella typhimurium* ($10^6$–$10^7$ c. f.u./ml) is added. The bacteria and biopsied cells are incubated together at 37° C. for 15 minutes to allow for infection of melanoma cells by the *S. typhimurium*, and the cells are then rinsed with TBS to remove non-infecting bacteria. The cells are then permeablized with 0.01% saponin in 3% bovine serum albumin for 5 min, stained for DNA for 10 minutes with 2.5 mg/ml 4'–6 Diamidino-2-phenyhndole (DAPI) and saponin (0.01%) in TBS, washed with TBS, mounted in MOWIO™ polymer mounting agent (Calbiochem) containing 1, 4-Diazabicyclo (2,2,2) octane (DABCO, Kodak) and observed by phase and fluorescence microscopy. The presence of DAPI-stain in the cytoplasm of the biopsied cells would indicate that they were melanoma cells, i.e., cells that were infected by the melanoma-specific *S. typhimurium* are melanoma cells rather than melanocytes.

23. EXAMPLE

Melanoma Tumor Targeting By Listeria Monocytogenes

This example demonstrates that Listeria monocytogenes targets to and proliferates in tumor cells when administered to melanoma bearing animals.

C57B/6 mice were inoculated s.c. in the left flank with $5 \times 10^5$ B16F10 melanoma cells. When the tumors reached about 1–2 g (16 days post implantation of tumor cells) the animals were inoculated i.p. with 7×10$^5$ cfu of Listeria monocytogenes wild type strain 43251. Prior to inoculation into mice, the Listeria culture was grown overnight in LB media to an OD$_{600}$ of 0.25. At the times indicated animals were sacrificed and the tumors and livers were removed, homogenized and quantitated for bacterial numbers by plating serial dilutions onto L.B. plates.

Tumors were analyzed at 24, 48, and 96 hours post-inoculation of Listeria monocytogenes. Results are shown in Table 20(I).

TABLE 20(I)

AMPLIFICATION OF LISTERIA MONOCYTOGENES IN C57B/6 MICE-BEARING B16F10 MELANOMA TUMORS

| Time Post-inoc. | L. monocytogenes/g tissue: | | Tumor:Liver |
|---|---|---|---|
| | Tumor | Liver | |
| 24 hrs | 1.5 ± 1.4 × 10$^3$ | 8.0 ± 6.1 × 10$^4$ | 1:5 |
| 48 hrs | 6.3 ± 8.5 × 10$^2$ | 1.3 ± 1.0 × 10$^5$ | 1:210 |
| 96 hrs | 5.2 ± 6.8 × 10$^5$ | 5.7 ± 9.0 × 10$^5$ | 1:1 |

The results represent the average ± SD of triplicate determinations.

As shown in Table 20(I) it was found that the levels of bacteria within the tumors rose about 100 fold during this time period, indicating that wild type *Listeria monocytogenes* can target tumors and proliferate within them. *Listeria monocytogenes* strain 43251 was virulent in the C57B/6 mice, causing death about 5 days pot-inoculation i.p. of 7×10$^5$ cfu.

24. EXAMPLE

Leishmania Amazonensis Shows Tumor Cell Specificity 24.1. Leishmania Amazonensis Specifically Attaches to Human Melanoma Cells in Vitro

*Leishmania amazonensis* trypomastigotes are regarded as being highly biospecific, in that they are unable to infect virtually any cell types other than macrophages. Since human melanomas are known to express some macrophage-like traits it was determined whether *Leishmania amazonensis* would be able to enter into human melanoma cells in culture. *Leishmania amazonensis* promastigotes were grown in Schneider's Drosophila media (GIBCO BRL) containing 15% heat-inactivated fetal calf serum at 24° C. until the parasites were in late log phase (usually 3 to 4 days). Animal cells used in the *L. amazonensis* infection assays were a mouse melanoma cell line which forms non-metastatic tumors when injected into C57B6 mice (B16/F1), two human metastatic melanoma cell lines (M2 and M2-A7, and as a negative control human foreskin fibroblasts, HFF. These different cell types were grown on glass coverslips in 24 well plates or on plastic Lab-Tec® (Nunc) slides in MEM culture medium with 10% fetal calf serum, for HFF cells; Ham's F10 medium with 10% horse serum for B16/F1 cells; and DMEM with 10% fetal calf serum buffered with 10 mM HEPES, for M2 and M2-A7 cells.

The Leishmania parasites were pre-incubated for about one hour with 5% normal human serum and the cultured cells were infected with 0.5 to 5.0×10$^6$ parasites/ml for about two hours at 32° C. After incubation the cells were washed twice with phosphate buffered saline (PBS) and fixed with 3% paraformaldehyde for about 30 minutes at about 4° C. An anti-Leishmanial antibody was incubated with the fixed cells at a normal working dilution (1:100,000) in PBS with 3% bovine serum albumen (BSA) for about one hour. After washing, a fluorescent-conjugated anti-mouse antibody (Boehringer Mannheim) was incubated with the cells at a normal working dilution (1:500) for about one hour and then washed from the cells. The cells were then permeabilized with 0.02% Saponin (Sigma, a detergent used to remove lipids, thereby allowing penetration by antibodies) in Tris buffered saline (TBS) for 10min and stained for DNA with 5.0 mg/ml DAPI stain (Sigma) in TBS with 0.02% Saponin. The cells were washed with TBS and mounted on glass slides using MOWIOL™ polymer mounting agent (CalBiochem) with DABCO (Kodak, a compound that sustains fluorescent emissions). The presence of internalized parasites was determined by failure to react with an anti-Leishmania monoclonal antibody in the absence of host cell membrane permeabilization.

Figure 13A:
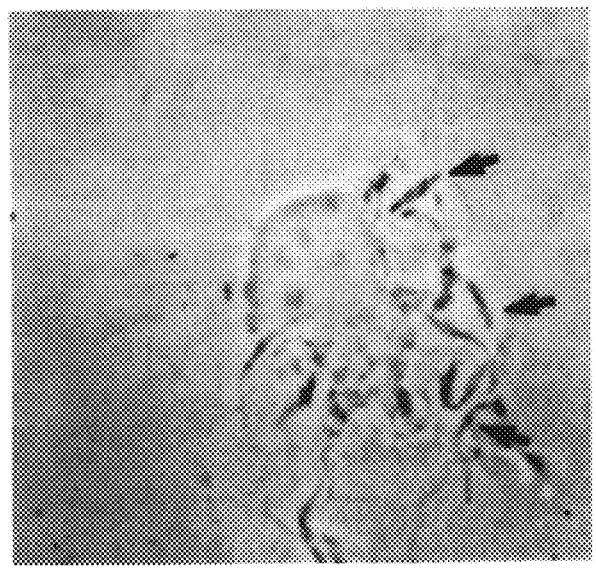
FIGS. 13A–B.
Figure 13B:
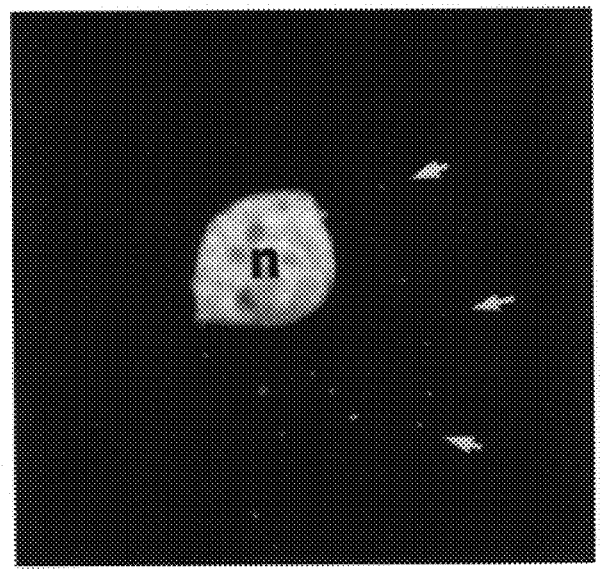

Observations made immediately after addition of the live parasites using an inverted phase microscope showed that among these cell lines, motile parasites were immediately adherent only when they encountered the metastatic melanoma cells, suggesting that the metastatic cells may possess an appropriate receptor for Leishmania. These results are shown in FIG. 13.

To determine whether or not the Leishmania parasites were internalized, M2 human melanoma cells were grown, infected with Leishmania and fixed as described above with 3% paraformaldehyde at 4° C. for about 30 minutes without permeabilization, washed and immunostained with a monoclonal antibody directed toward a Leishmania surface protein, followed by a rhodamine-conjugated anti-mouse antibody. After washing in Tris-buffered saline (TBS), the cells were permeablized with 0.01% saponin in 3% BSA for 5 minutes, and stained for DNA 10 minutes with 2.5 mg/ml 4'-6 Diamidino-2-phenylindole (DAPI) and 0.01% saponin in TBS, washed with TBS, mounted in MOWIOL™ polymer mounting agent (CaIbiochem) containing 1, 4-Diazabicyclo (2,2,2) octane (DABCO, Kodak) and observed by phase and fluorescence microscopy. This procedure detects all parasites and distinguishes between those which are internalized (inaccessible to antibody staining in non-permeabilized cells), and those which are attached but not internalized.

Parasites were internalized by M2 cells (data not shown). Internalization was estimated to occur in 3% of the melanoma cells. These findings demonstrate that a) live Leishmania parasites were able to enter the melanoma cells, and b) possibly only a sub-population of the melanoma cells were involved in the process.

24.2. Lysosomal Fusion Follows Internalization of Leishmania By Melanoma

Figure 14A:
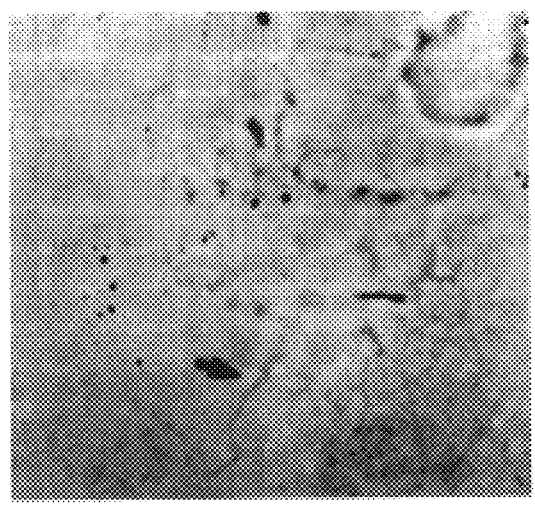
FIGS. 14A–C.
Figure 14B:
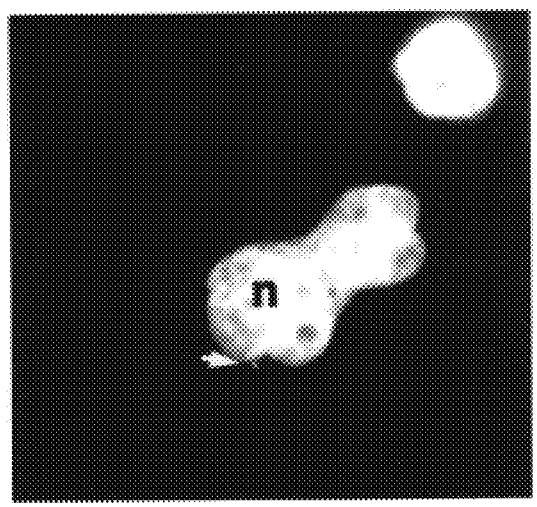
Figure 14C:

In the normal course of invasion of macrophages by Leishmania, lysosomes fuse with the phagosome. To determine whether or not this also occurs when Leishmania invade melanoma cells, parasites were co-localized with a lysosomal glycoprotein (lgp) marker. The cells were grown, infected and fixed as described above except the cells were immunostained with a monoclonal antibody directed against a human lysosomal glycoprotein, LAMP-1, followed by a rhodamine-conjugated antimouse antibody. After washing in TBS, the cells were stained for DNA 10 minutes with 2.5 mg/ml DAPI, washed with TBS, mounted in MOWIOL™ polymer mounting agent containing DABCO and observed by phase and fluorescence microscopy. Parasites co-localizing with LAMP-1 are shown in FIGS. 14A–C. Co-localization corroborates the internalization of the parasite and demonstrates that the process of lysosomal fusion occurs when Leishmania is internalized into the melanoma cells. In summary, *Leishmania amazonensis* in its wild type state shows invasion ability for human melanoma cells that has been heretofore unreported.

25. EXAMPLE

Diagnosis of Melanoma In Human Tissue Biopsies Using Leishmania Amazonensis

Diagnosis of melanoma according to the methods of the present invention can be performed using, for example, *Leishmaina Amazonensis* as follows: A portion of a biopsied specimen suspected of melanoma is minced with scissors in tris-buffered saline (TBS) and then incubated in $Ca^{++}/Mg^{++}$-free saline containing trypsin, collagenase, and EDTA at 37° C. for 60 minutes to dissociate the tissue into individual cells. The cells are then rinsed free of the dissociation enzymes by centrifugation. The cells are resuspended in 1 ml DMEM/10% FBS and added to a 24 well Corning tissue culture chamber containing cover slips in the wells. The cells are then incubated in a gassed, 5% $CO_2$, humidified incubator at 37° C. for about three hours to allow for attachment to the cover slip.

After attachment of the biopsied cells is achieved, a melanoma-specific strain of *Leishmania amazonensis* promastigotes which has been isolated according to the methods of the present invention is added. The parasites and biopsied cells are incubated together at 37° C. for about two hours to allow for infection of melanoma cells by the *Leishmania amazonensis* and the cells are then rinsed with TBS to remove non-infecting parasites. The cells are then permeablized with 0.01% saponin in 3% bovine serum albumin for five minutes, stained for DNA with 2.5 mg/ml 4'-6 Diamiclino-2-phenylindole (DAPI) and saponin (0.01%) in TBS for 10 minutes, washed with TBS, mounted in MOWIOL™ polymer mounting agent (Calbiochem) containing 1,4-Diazabicyclo (2,2,2) octane (DABCO, Kodak) and observed by phase and fluorescence microscopy. The presence of DAPI-stain in the cytoplasm of the biopsied cells would indicate that they were melanoma cells.

26. EXAMPLE

Diagnosis of Human Tissue Biopsies For Melanoma Using Mycobacterium Avium

*Mycobacterium avium* were found associated with the melanoma cells but not with the normal melanocytes. This discriminatory ability for melanoma cells demonstrates the ability of *Mycobacterium avium* as a vector in the diagnosis and treatment of melanoma. Diagnosis of melanoma using *Mycobacterium avium* is as follows: A portion of a biopsied specimen suspected of melanoma is minced with scissors in tris-buffered saline (TBS) and then incubated in $Ca^{++}/Mg^{++}$-free saline containing trypsin, collagenase, and EDTA at 37° C. for 60 minutes to dissociate the tissue into individual cells. The cells are then rinsed free of the dissociation enzymes by centrifugation. The cells are resuspended in 1 ml DMEM/10% FBS and plated onto 12 mm glass cover slips in 24 well plates with $1 \times 10^5$ cells per well. The cells are then incubated in a gassed 5% $CO_2$, humidified incubator 37° C. for 3 hours to allow for attachment of the cells to the cover slip.

After attachment of the biopsied cells is achieved, a melanoma-specific strain of *Mycobacterium avium* which has been isolated by the methods of the present invention is added. The bacteria and biopsied cells are incubated together at 37° C. for 15 minutes for infection of melanoma cells by the *Mycobacterium avium*. The cells are then rinsed with TBS to remove non-infecting bacteria. The cells are then permeablized with 0.01% saponin in 3% bovine serum albumin for five minutes, stained for DNA with 2.5 mg/ml 4'-6 Diamidino-2-phenylindole (DAPI) and saponin (0.01%) in TBS for 10 minutes, washed with TBS, mounted in MOWIOL™ polymer mounting agent (Calbiochem) containing 1, 4-Diazabicyclo (2,2,2) octane (DABCO, Kodak) and observed by phase and fluorescence microscopy. The presence of DAPI-stain in the cytoplasm of the biopsied cells would indicate that they were melanoma cells.

27. DEPOSIT OF MICROORGANISMS

The following microorganisms were deposited with the American Type Culture Collection (ATCC), Manassas, Va. on Jun. 1, 1995 and have been assigned the indicated Accession numbers:

| Microorganism | ATCC Accession No. |
| --- | --- |
| Clone #70 | 55686 |
| Clone #71 | 55685 |
| Clone #72 | 55680 |
| Clone #72$^{5-3-2}$ | 97179 |
| Population #72$^{pop-1}$ | 55684 |
| Population #72$^{pop-2}$ | 55683 |
| Population #14028$^{pop-1}$ | 55681 |
| Population #14028$^{pop-2}$ | 55682 |

The following microorganisms were deposited with the American Type Culture Collection (ATCC), Manassas, Va. on May 30, 1996, and have been assigned the indicated Accession numbers:

| Microorganism | ATCC Accession No. |
| --- | --- |
| Clone YS721 | 55788 |
| Clone YS7211 | 55787 |
| Clone YS7212 | 55789 |
| Clone YS7213 | 55786 |

The following plasmids were deposited with the American Type Culture Collection (ATCC), Manassas, Va. on May 30, 1996, and have been assigned the indicated Accession numbers:

| Microorganism | ATCC Accession No. |
| --- | --- |
| pTK-Sec3 | 97592 |
| pCD-Sec1 | 97593 |
| pSP-SAD4-5 | 97591 |

The invention claimed and described herein is not to be limited in scope by the specific embodiments herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A method for reducing volume or inhibiting growth of a solid tumor cancer, comprising: administering an amount of tumor specific microorganisms, which replicate preferentially in the tumor after administration, to a patient having a solid tumor cancer, wherein the tumor specific microorganisms grow under both aerobic and anaerobic conditions, which amount is effective to reduce volume or inhibit growth of said solid tumor cancer, and wherein the tumor specific microorganisms are a tumor specific Shigella species, wherein the tumor specific microorganisms are super-infective, tumor specific microorganisms.

2. A method for reducing volume or inhibiting growth of a solid tumor cancer, comprising: administering an amount of tumor specific microorganisms, which replicate preferentially in the tumor after administration, to a patient having a solid tumor cancer, wherein the specific microorganisms grow under both aerobic and anaerobic conditions, which amount is effective to reduce volume or inhibit growth of said solid tumor cancer, and wherein the tumor specific microorganisms are a tumor specific Shigella species, wherein the tumor specific microorganisms are attenuated.

3. The method according to claim 1 wherein the tumor specific microorganisms are auxotrophic mutants.

4. The method according to claim 2 wherein the attenuated microorganisms express an altered lipid A molecule.

5. The method according to claim 2 wherein the attenuated microorganisms induce TNF-α expression in monocytes or macrophages from about 1 to about 75 percent compared to non-attenuated microorganisms.

6. The method according to claim 2 wherein the tumor specific microorganisms are auxotrophic mutants.

7. The method according to claim 1 wherein the super-infective, tumor specific microorganisms are produced by:
(a) exposing a cell culture of a solid tumor cancer to a microorganism for a time sufficient so that the microorganism can infect the tumor cells;
(b) allowing the microorganism to replicate, thereby producing super-infective, tumor specific microorganisms; and
(c) isolating the super-infective, tumor specific microorganisms from the infected cell culture.

8. The method according to claim 1 wherein the tumor specific microorganisms are produced by:
(a) exposing a microorganism to tumor cell conditioned medium for a time sufficient to allow the microorganism to chemotact towards the tumor cell conditioned medium;
(b) allowing the microorganism to replicate, thereby producing microorganisms which chemotact towards the tumor cell conditioned medium; and
(c) isolating the microorganisms which chemotact towards the tumor cell conditioned medium.

9. The method according to claim 1 wherein the super-infective, tumor specific microorganisms are produced by:
(a) exposing a mammal having a solid tumor cell cancer to a microorganism for a time sufficient so that the microorganism can infect the tumor cells;
(b) allowing the microorganism to replicate, thereby producing super-infective, tumor specific microorganisms; and
(c) isolating the super-infective, tumor specific microorganisms from the infected tumor cells.

10. The method according to claim 2 wherein the tumor specific microorganisms are produced by:
(a) exposing a microorganism to tumor cell conditioned medium for a time sufficient to allow the microorganism to chemotact towards the tumor cell conditioned medium;
(b) allowing the microorganism to replicate, thereby producing microorganisms which chemotact towards the tumor cell conditioned medium; and
(c) isolating the microorganisms which chemotact towards the tumor cell conditioned medium.

11. The method according to claim 1 or 2 wherein the effective amount is from about 1 to $1 \times 10^8$ c.f.u./kg.

12. The method according to claim 1 or 2 wherein the effective amount is from about 1 to $1 \times 10^2$ c.f.u./kg.

13. The method according to claim 1 or 2 wherein the tumor specific microorganisms are genetically engineered.

14. The method according to claim 7, 8 or 9 or 10 further comprising:
subjecting the microorganism to mutagenesis before step (a).

15. The method according to claim 7, 8 or 9 or 10 further comprising:
(c) repeating steps (a) and (b) a desired number of times.

16. The method according to claim 1, 2, 7, 8, 9 or 10 wherein the solid tumor cancer is melanoma cancer.

17. The method according to claim 1, 2, 7, 8, 9 or 10 wherein the solid tumor cancer is colon carcinoma cancer.

18. The method according to claim 1, 2, 7, 8, 9 or 10 wherein the solid tumor cancer is selected from the group consisting of lung cancer, liver cancer, kidney cancer, prostate cancer and breast cancer.

19. The method according to claims 1, 2, 7, 8, 9, or 10 wherein the solid tumor cancer is a metastatic cancer.

20. The method according to claim 13 wherein the tumor specific microorganisms express a suicide gene.

21. The method according to claim 20 wherein the tumor specific microorganisms express a suicide gene selected from the group consisting of p450 oxidoreductase, HSV thymidine kinase, *E. coli* cytosine deaminase, carboxypeptidase G2, β-glucuronidase, penicillin-V-amidase, penicillin-G-amidase, β-lactamase, β-glucosidase, nitroreductase and carboxypeptidase A.

22. The method according to claim 20 wherein expression of the suicide gene is controlled by a constitutive promoter, an inducible promoter, or a tumor cell specific promoter.

23. The method according to claim 20 wherein the suicide gene is encoded by the open reading frame of the insert of a plasmid selected from the group consisting of pTK-Sec3, pCD-Sec1 and pSP-SAD4-5.

24. The method according to claim 23 wherein the suicide gene is selected from the group consisting of HSV thymidine kinase and *E. coli* cytosine deaminase.

25. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, which amount is effective to reduce volume or inhibit growth of said solid tumor cancer, and wherein the tumor specific microorganisms are a tumor specific Shigella species, wherein the single colony clone of an isolated population of tumor specific microorganisms is a single colony clone of an isolated population of super-infective, tumor specific microorganisms.

26. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, which amount is effective to reduce volume or inhibit growth of said solid tumor cancer, and wherein the tumor specific microorganisms are a tumor specific Shigella species, wherein the tumor specific single colony clone is attenuated.

27. The method according to claim 25 wherein the single colony clone of an isolated population of super-infective, tumor specific microorganisms is produced by:
   (a) exposing a cell culture of a solid tumor cancer to a microorganism for a time sufficient so that the microoranism can infect the tumor cells;
   (b) isolating a population of super-infective, tumor specific microorganisms from the infected cell culture; and
   (c) culturing the population isolated in step (b) so that single colony clones are obtained.

28. The method according to claim 25 wherein the single colony clone of an isolated population of tumor specific microorganisms is produced by:
   (a) exposing a microorganism to tumor cell conditioned medium for a time sufficient to allow the microorganism to chemotact towards the tumor cell conditioned medium;
   (b) isolating a population of microorganisms which chemotacts towards the tumor cell conditioned medium; and
   (c) culturing the population isolated in step (b) so that single colony clones are obtained.

29. The method according to claim 25 wherein the single colony clone of an isolated population of super-infective, tumor specific microorganisms is produced by:
   (a) exposing a mammal having a solid tumor cell cancer to a microorganism for a time sufficient so that the microorganism can infect the tumor cells;
   (b) isolating a population of super-infective, tumor specific microorganisms from the infected tumor cells; and
   (c) culturing the population isolated in step (b) so that single colony clones are obtained.

30. The method according to claim 25 or 26 wherein the single colony clone is genetically engineered.

31. The method according to claim 25 or 26 wherein the effective amount is from about 1 to $1 \times 10^8$ c.f.u./kg.

32. The method according to claim 25 or 26 wherein the effective amount is from about 1 to $1 \times 10^2$ c.f.u./kg.

33. The method according to claim 26 wherein the single colony clone of an isolated population of tumor specific microorganisms is produced by:
   (a) exposing a microorganism to tumor cell conditioned medium for a time sufficient to allow the microorganism to chemotact towards the tumor cell conditioned medium;
   (b) isolating a population of microorganisms which chemotacts towards the tumor cell conditioned medium; and
   (c) culturing the population isolated in step (b) so that single colony clones are obtained.

34. The method according to claim 26 wherein the attenuated clone expresses an altered lipid A molecule.

35. The method according to claim 26 wherein the single colony clone induces TNF-α expression in monocytes or macrophages from about 1 to about 75 percent compared to a single colony clone that is not attenuated.

36. The method according to claim 27, 28, 29 or 33 further comprising:

subjecting the microorganism to mutagenesis before step (a).

37. The method according to claim 27, 28, 29 or 33 further comprising:
   (d) repeating steps (a) and (b) a desired number of times before step (c).

38. The method according to claim 25, 26, 27, 28, 29 or 33 wherein the solid tumor cancer is melanoma cancer.

39. The method according to claim 25, 26, 27, 28, 29 or 33 wherein the solid tumor cancer is colon carcinoma cancer.

40. The method according to claim 25, 26, 27, 28, 29 or 33 wherein the solid tumor cancer is selected from the group consisting of lung cancer, liver cancer, kidney cancer, prostate cancer and breast cancer.

41. The method according to claims 25, 26, 27, 28, 29, or 33 wherein the solid tumor cancer is a metastatic cancer.

42. The method according to claim 30 wherein the single colony clone expresses a suicide gene.

43. The method according to claim 42 wherein expression of the suicide gene is controlled by a constitutive promoter, an inducible promoter, or a tumor cell specific promoter.

44. The method according to claim 42 wherein the suicide gene is encoded by the open reading frame of the insert of a plasmid selected from the group consisting of pTK-Sec3, pCD-Sec1 and pSP-SAD4-5.

45. The method according to claim 44 wherein the suicide gene is selected from the group consisting of HSV thymidine kinase and *E. coli* cytosine deaminase.

46. The method according to claim 42 wherein the single colony clone expresses a suicide gene selected from the group consisting of p450 oxidoreductase, HSV thymidine kinase, *E. coli* cytosine deaminase, carboxypeptidase G2, β-glucuronidase, penicillin-V-amidase, penicillin-G-amidase, β-lactamase, β-glucosidase, nitroreductase and carboxypeptidase A.

47. The method according to claim 46 wherein the suicide gene is selected from the group consisting of HSV thymidine kinase and *E. coli* cytosine deaminase.

48. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by an inducible promoter, which amount is effective to reduce volume or inhibit growth of said solid tumor cancer, and wherein the tumor specific microorganisms are a tumor specific Shigella species.

49. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms, which grows under both aerobic and anaerobic conditions, and wherein the single colony clone expresses a suicide gene which gene is controlled by a bacterial promoter that is activated in specific tumor cells, which amount is effective to reduce volume or inhibit growth of said solid tumor cancer, and wherein the tumor specific microorganisms are a tumor specific Shigella species.

50. A diagnostic kit comprising an effective amount of a tumor-specific microorganism and instructions for use for in vitro diagnosis of a solid tumor cancer, wherein the tumor specific microorganism is a tumor specific Shigella species.

51. The diagnostic kit according to claim 50 further comprising non-cancerous counterpart control cells.

52. The diagnostic kit according to claim 50 wherein the tumor-specific microorganism is a super-infective, tumor-specific microorganism.

53. The diagnostic kit according to claim 52 wherein the microorganism is genetically engineered.

54. A method for reducing volume or inhibiting growth of a solid tumor cancer, comprising: administering an amount of an tumor specific microorganisms, which replicate preferentially in the tumor after administration, to a patient having a solid tumor cancer, wherein the tumor specific microorganisms grow under both aerobic and anaerobic conditions, which amount is effective to reduce volume or inhibit growth of said solid tumor cancer, and wherein the tumor specific microorganisms are a tumor specific Streptococcus species genetically engineered to express a suicide gene.

55. The method according to claim 54 wherein the effective amount is from about 1 to $1 \times 10^8$ c.f.u./kg.

56. The method according to claim 54 wherein the effective amount is from about 1 to $1 \times 10^2$ c.f.u./kg.

57. The method according to claim 54 wherein the tumor specific microorganisms are auxotrophic mutants.

58. The method according to claim 54 wherein the tumor specific microorganisms are super-infective, tumor specific microorganisms.

59. The method according to claim 54 wherein the tumor specific microorganisms are attenuated.

60. The method according to claim 54 wherein the tumor specific microorganisms are produced by:
  (a) exposing a microorganism to tumor cell conditioned medium for a time sufficient to allow the microorganism to chemotact towards the tumor cell conditioned medium;
  (b) allowing the microorganism to replicate, thereby producing microorganisms which chemotact towards the tumor cell conditioned medium; and
  (c) isolating the microorganisms which chemotact towards the tumor cell conditioned medium.

61. The method according to claims 54, 63, 60 or 64 wherein the solid tumor cancer is a metastatic cancer.

62. The method according to claim 59 wherein the attenuated microorganisms induce TNF-α expression in monocytes or macrophages from about 1 to about 75 percent compared to non-attenuated microorganisms.

63. The method according to claim 58 wherein the super-infective, tumor specific microorganisms are produced by:
  (a) exposing a cell culture of a solid tumor cancer to a microorganism for a time sufficient so that the microorganism can infect the tumor cells;
  (b) allowing the microorganism to replicate, thereby producing super-infective, tumor specific microorganisms; and
  (c) isolating the super-infective, tumor specific microorganisms from the infected cell culture.

64. The method according to claim 58 wherein the super-infective, tumor specific microorganisms are produced by:
  (a) exposing a mammal having a solid tumor cell cancer to a microorganism for a time sufficient so that the microorganism can infect the tumor cells;
  (b) allowing the microorganism to replicate, thereby producing super-infective, tumor specific microorganisms; and
  (c) isolating the super-infective, tumor specific microorganisms from the infected tumor cells.

65. The method according to claim 59 wherein the attenuated population expresses an altered lipid A molecule.

66. The method according to claim 58 wherein the tumor specific microorganisms are auxotrophic mutants.

67. The method according to claim 63, 60 or 64 further comprising:
  subjecting the microorganism to mutagenesis before step (a).

68. The method according to claim 63, 60 or 64 further comprising:
  (c) repeating steps (a) and (b) a desired number of times.

69. The method according to claim 54, 63, 60 or 64 wherein the solid tumor cancer is melanoma cancer.

70. The method according to claim 54, 63, 60 or 64 wherein the solid tumor cancer is colon carcinoma cancer.

71. The method according to claim 54, 63, 60 or 64 wherein the solid tumor cancer is selected from the group consisting of lung cancer, liver cancer, kidney cancer, prostate cancer and breast cancer.

72. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by an inducible promoter, which amount is effective to reduce volume or inhibit growth of said solid tumor cancer, and wherein the tumor specific microorganisms are a tumor specific Streptococcus species genetically engineered to express a suicide gene.

73. The method according to claim 72 wherein the effective amount is from about 1 to $1 \times 10^8$ c.f.u./kg.

74. The method according to claim 72 wherein the effective amount is from about 1 to $1 \times 10^2$ c.f.u./kg.

75. The method according to claim 72 wherein the single colony clone of an isolated population of tumor specific microorganisms is a single colony clone of an isolated population of super-infective, tumor specific microorganisms.

76. The method according to claim 72 wherein the tumor specific single colony clone is attenuated.

77. The method according to claim 72 wherein the single colony clone of an isolated population of tumor specific microorganisms is produced by:
  (a) exposing a microorganism to tumor cell conditioned medium for a time sufficient to allow the microorganism to chemotact towards the tumor cell conditioned medium;
  (b) isolating a population of microorganisms which chemotacts towards the tumor cell conditioned medium; and
  (c) culturing the population isolated in step (b) so that single colony clones are obtained.

78. The method according to claim 72 or 75 wherein the suicide gene is encoded by the open reading frame of the insert of a plasmid selected from the group consisting of pTK-Sec3, pCD-Sec1 and pSP-SAD4-5.

79. The method according to claim 72 or 75 wherein the suicide gene selected from the group consisting of p450 oxidoreductase, HSV thymidine kinase, *E. coli* cytosine deaminase, carboxypeptidase G2, β-glucuronidase, penicillin-V-amidase, penicillin-G-amidase, β-lactamase, β-glucosidase, nitroreductase and carboxypeptidase A.

80. The method according to claim 72 or 75 wherein expression of the suicide gene is controlled by a constitutive promoter, an inducible promoter, or a tumor cell specific promoter.

81. The method according to claim 78 wherein the suicide gene is selected from the group consisting of HSV thymidine kinase and *E. coli* cytosine deaminase.

82. The method according to claim 79 wherein the suicide gene is selected from the group consisting of HSV thymidine kinase and *E. coli* cytosine deaminase.

83. The method according to claim 76 wherein the single colony clone induces TNF-α expression in monocytes or macrophages from about 1 to about 75 percent compared to a single colony clone that is not attenuated.

84. The method according to claim 75 wherein the single colony clone of an isolated population of super-infective, tumor specific microorganisms is produced by:
   (a) exposing a cell culture of a solid tumor cancer to a microorganism for a time sufficient so that the microorganism can infect the tumor cells;
   (b) isolating a population of super-infective, tumor specific microorganisms from the infected cell culture; and
   (c) culturing the population isolated in step (b) so that single colony clones are obtained.

85. The method according to claim 75 wherein the single colony clone of an isolated population of super-infective, tumor specific microorganisms is produced by:
   (a) exposing a mammal having a solid tumor cell cancer to a microorganism for a time sufficient so that the microorganism can infect the tumor cells;
   (b) isolating a population of super-infective, tumor specific microorganisms from the infected tumor cells; and
   (c) culturing the population isolated in step (b) so that single colony clones are obtained.

86. The method according to claim 84, 77 or 85 further comprising:
   subjecting the microorganism to mutagenesis before step (a).

87. The method according to claim 84, 77 or 85 further comprising:
   (d) repeating steps (a) and (b) a desired number of times before step (c).

88. The method according to claim 72, 84, 77 or 85 wherein the solid tumor cancer is melanoma cancer.

89. The method according to claim 72, 84, 77 or 85 wherein the solid tumor cancer is colon carcinoma cancer.

90. The method according to claim 72, 84, 77 or 85 wherein the solid tumor cancer is selected from the group consisting of lung cancer, liver cancer, kidney cancer, prostate cancer and breast cancer.

91. The method according to claims 72, 84, 77 or 85 wherein the solid tumor cancer is a metastatic cancer.

92. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms that grows under both aerobic and anaerobic conditions, and wherein the single colony clone expresses a suicide gene which gene is controlled by an inducible promoter, which amount is effective to reduce volume or inhibit growth of said solid tumor cancer, and wherein the tumor specific microorganisms are a tumor specific Streptococcus species genetically engineered to express a suicide gene.

93. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms, which grows under both aerobic and anaerobic conditions, and wherein the single colony clone expresses a suicide gene which gene is controlled by a bacterial promoter that is activated in specific tumor cells, which amount is effective to reduce volume or inhibit growth of said solid tumor cancer, and wherein the tumor specific microorganisms are a tumor specific Streptococcus species genetically engineered to express a suicide gene.

94. A method for reducing volume or inhibiting growth of a solid tumor cancer, comprising: administering an amount of tumor specific microorganisms, which replicate preferentially in the tumor after administration, to a patient having a solid tumor cancer, wherein the tumor specific microorganisms grow under both aerobic and anaerobic conditions, which amount is effective to reduce volume or inhibit growth of said solid tumor cancer, wherein the tumor specific microorganisms are a tumor specific Streptococcus species, and wherein the administration is oral, topical, intravenous, intraperitoneal, subcutaneous, or intramuscular.

95. The method according to claim 94 wherein the effective amount is from about 1 to $1 \times 10^8$ c.f.u./kg.

96. The method according to claim 94 wherein the effective amount is from about 1 to $1 \times 10^2$ c.f.u./kg.

97. The method according to claim 94 wherein the tumor specific microorganisms are auxotrophic mutants.

98. The method according to claim 94 wherein the tumor specific microorganisms are super-infective, tumor specific microorganisms.

99. The method according to claim 94 wherein the tumor specific microorganisms are attenuated.

100. The method according to claim 94 wherein the tumor specific microorganisms are produced by:
   (a) exposing a microorganism to tumor cell conditioned medium for a time sufficient to allow the microorganism to chemotact towards the tumor cell conditioned medium;
   (b) allowing the microorganism to replicate, thereby producing microorganisms which chemotact towards the tumor cell conditioned medium; and
   (c) isolating the microorganisms which chemotact towards the tumor cell conditioned medium.

101. The method according to claim 99 wherein the attenuated microorganisms induce TNF-α expression from about 1 to about 75 percent compared to non-attenuated microorganisms.

102. The method according to claim 98 wherein the super-infective, tumor specific microorganisms are produced by:
   (a) exposing a cell culture of a solid tumor cancer to a microorganism for a time sufficient so that the microorganism can infect the tumor cells;
   (b) allowing the microorganism to replicate, thereby producing super-infective, tumor specific microorganisms; and
   (c) isolating the super-infective, tumor specific microorganisms from the infected cell culture.

103. The method according to claim 98 wherein the super-infective, tumor specific microorganisms are produced by:

(a) exposing a mammal having a solid tumor cell cancer to a microorganism for a time sufficient so that the microorganism can infect the tumor cells;

(b) allowing the microorganism to replicate, thereby producing super-infective, tumor specific microorganisms; and (c) isolating the super-infective, tumor specific microorganisms from the infected tumor cells.

104. The method according to claim 102, 100 or 103 further comprising:

subjecting the microorganism to mutagenesis before step (a).

105. The method according to claim 102, 100 or 103 further comprising:

(c) repeating steps (a) and (b) a desired number of times.

106. The method according to claim 94, 102, 100 or 103 wherein the solid tumor cancer is melanoma cancer.

107. The method according to claim 94, 102, 100 or 103 wherein the solid tumor cancer is colon carcinoma cancer.

108. The method according to claim 94, 102, 100 or 103 wherein the solid tumor cancer is selected from the group consisting of lung cancer, liver cancer, kidney cancer, prostate cancer and breast cancer.

109. The method according to claims 94, 102, 100 or 103 wherein the solid tumor cancer is a metastatic cancer.

110. The method according to claim 98 wherein the tumor specific microorganisms are auxotrophic mutants.

111. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, which amount is effective to reduce volume or inhibit growth of said solid tumor cancer, wherein the tumor specific microorganisms are a tumor specific Streptococcus species, and wherein the administration is oral, topical, intravenous, intraperitoneal, subcutaneous, or intramuscular.

112. The method according to claim 111 wherein the effective amount is from about 1 to $1 \times 10^8$ c.f.u./kg.

113. The method according to claim 111 wherein the effective amount is from about 1 to $1 \times 10^2$ c.f.u./kg.

114. The method according to claim 111 wherein the single colony clone of an isolated population of tumor specific microorganisms is a single colony clone of an isolated population of super-infective, tumor specific microorganisms.

115. The method according to claim 111 wherein the tumor specific single colony clone is attenuated.

116. The method according to claim 111 or 114 wherein the single colony clone is genetically engineered.

117. The method according to claim 111 wherein the single colony clone of an isolated population of tumor specific microorganisms is produced by:

(a) exposing a microorganism to tumor cell conditioned medium for a time sufficient to allow the microorganism to chemotact towards the tumor cell conditioned medium;

(b) isolating a population of microorganisms which chemotacts towards the tumor cell conditioned medium; and (c) culturing the population isolated in step (b) so that single colony clones are obtained.

118. The method according to claim 115 wherein the single colony clone induces TNF-α expression from about 1 to about 75 percent compared to a single colony clone that is not attenuated.

119. The method according to claim 114 wherein the single colony clone of an isolated population of super-infective, tumor specific microorganisms is produced by:

(a) exposing a cell culture of a solid tumor cancer to a microorganism for a time sufficient so that the microorganism can infect the tumor cells;

(b) isolating a population of super-infective, tumor specific microorganisms from the infected cell culture; and (c) culturing the population isolated in step (b) so that single colony clones are obtained.

120. The method according to claim 114 wherein the single colony clone of an isolated population of super-infective, tumor specific microorganisms is produced by:

(a) exposing a mammal having a solid tumor cell cancer to a microorganism for a time sufficient so that the microorganism can infect the tumor cells;

(b) isolating a population of super-infective, tumor specific microorganisms from the infected tumor cells; and (c) culturing the population isolated in step (b) so that single colony clones are obtained.

121. The method according to claim 119, 117 or 120 further comprising:

subjecting the microorganism to mutagenesis before step (a).

122. The method according to claim 119, 117 or 120 further comprising:

(d) repeating steps (a) and (b) a desired number of times before step (c).

123. The method according to claim 111, 119, 117 or 120 wherein the solid tumor cancer is melanoma cancer.

124. The method according to claim 111, 119, 117 or 120 wherein the solid tumor cancer is colon carcinoma cancer.

125. The method according to claim 111, 119, 117 or 120 wherein the solid tumor cancer is selected from the group consisting of lung cancer, liver cancer, kidney cancer, prostate cancer and breast cancer.

126. The method according to claim 111, 119, 117 or 120 wherein the solid tumor cancer is a metastatic cancer.

127. The method according to claim 116 wherein the single colony clone expresses a suicide gene.

128. The method according to claim 127 wherein expression of the suicide gene is controlled by a constitutive promoter, an inducible promoter, or a tumor cell specific promoter.

129. The method according to claim 127 wherein the suicide gene is encoded by the open reading frame of the insert of a plasmid selected from the group consisting of pTK-Sec3, pCD-Sec1 and pSP-SAD4-5.

130. The method according to claim 127 wherein the single colony clone expresses a suicide gene selected from the group consisting of p450 oxidoreductase, HSV thymidine kinase, *E. coli* cytosine deaminase, carboxypeptidase G2, β-glucuronidase, penicillin-V-amidase, penicillin-G-amidase, β-lactamase, β-glucosidase, nitroreductase and carboxypeptidase A.

131. The method according to claim 129 wherein the suicide gene is selected from the group consisting of HSV thymidine kinase and *E. coli* cytosine deaminase.

132. The method according to claim 130, wherein the suicide gene is selected from the group consisting of HSV thymidine kinase and *E. coli* cytosine deaminase.

133. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by an inducible promoter, which amount is effective to reduce volume or inhibit growth of said solid tumor cancer, wherein the tumor specific microorganisms are a tumor specific Streptococcus species, and wherein the administration is oral, topical, intravenous, intraperitoneal, subcutaneous, or intramuscular.

134. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms, which grows under both aerobic and anaerobic conditions, and wherein the single colony clone expresses a suicide gene which gene is controlled by a bacterial promoter that is activated in specific tumor cells, which amount is effective to reduce volume or inhibit growth of said solid tumor cancer, wherein the tumor specific microorganisms are a tumor specific Streptococcus species, and wherein the administration is oral, topical, intravenous, intraperitoneal, subcutaneous, or intramuscular.

135. A method for reducing volume or inhibiting growth of a solid tumor cancer, comprising: administering an amount of tumor specific microorganisms, which replicates preferentially in the tumor after administration, to a patient having a solid tumor cancer, wherein the tumor specific microorganisms grow under both aerobic and anaerobic conditions, which amount is effective to reduce volume or inhibit growth of said solid tumor cancer, and wherein the tumor specific microorganisms are a tumor specific *Listeria monocytogenes*, wherein the tumor specific microorganisms are super-infective, tumor specific microorganisms.

136. A method for reducing volume or inhibiting growth of a solid tumor cancer, comprising: administering an amount of tumor specific microorganisms, which replicate preferentially in the tumor after administration, to a patient having a solid tumor cancer, wherein the specific microorganisms grow under both aerobic and anaerobic conditions, which amount is effective to reduce volume or inhibit growth of said solid tumor cancer, and wherein the tumor specific microorganisms are a tumor specific *Listeria monocytogenes*, wherein the tumor specific microorganisms are attenuated.

137. The method according to claim 135 wherein the tumor specific microorganisms are auxotrophic mutants.

138. The method according to claim 136 wherein the attenuated microorganisms induce TNF-α expression in monocytes or macrophages from about 1 to about 75 percent compared to non-attenuated microorganisms.

139. The method according to claim 135 wherein the super-infective, tumor specific microorganisms are produced by:
 (a) exposing a cell culture of a solid tumor cancer to a microorganism for a time sufficient so that the microorganism can infect the tumor cells;
 (b) allowing the microorganism to replicate, thereby producing super-infective, tumor specific microorganisms; and
 (c) isolating the super-infective, tumor specific microorganisms from the infected cell culture.

140. The method according to claim 135 wherein the tumor specific microorganisms are produced by:
 (a) exposing a microorganism to tumor cell conditioned medium for a time sufficient to allow the microorganism to chemotact towards the tumor cell conditioned medium;
 (b) allowing the microorganism to replicate, thereby producing microorganisms which chemotact towards the tumor cell conditioned medium; and
 (c) isolating the microorganisms which chemotact towards the tumor cell conditioned medium.

141. The method according to claim 135 wherein the super infective, tumor specific microorganisms are produced by:
 (a) exposing a mammal to having a solid tumor cell cancer to a microorganism for a time sufficient so that the microorganism can infect the tumor cells;
 (b) allowing the microorganism to replicate, thereby producing super-infective, tumor specific microorganisms; and
 (c) isolating the super-infective, tumor specific microorganisms from the infected tumor cells.

142. The method according to claim 136 wherein the tumor specific microorganisms are produced by:
 (a) exposing a microorganism to tumor cell conditioned medium for a time sufficient to allow the microorganism to chemotact towards the tumor cell conditioned medium;
 (b) allowing the microorganism to replicate, thereby producing microorganisms which chemotact towards the tumor cell conditioned medium; and
 (c) isolating the microorganisms which chemotact towards the tumor cell conditioned medium.

143. The method according to claim 135 or 136 wherein the tumor specific microorganisms are genetically engineered.

144. The method according to claim 139, 140, 141 or 142 further comprising:
 subjecting the microorganism to mutagenesis before step (a).

145. The method according to claim 139, 140, 141 or 142 further comprising:
 (c) repeating steps (a) and (b) a desired number of times.

146. The method according to claim 135, 136, 139, 140, 141 or 142 wherein the solid tumor cancer is melanoma cancer.

147. The method according to claim 135, 136, 139, 140, 141 or 142 wherein the solid tumor cancer is colon carcinoma cancer.

148. The method according to claim 135, 136, 139, 140, 141 or 142 wherein the solid tumor cancer is selected from the group consisting of lung cancer, liver cancer, kidney cancer, prostate cancer and breast cancer.

149. The method according to claims 135, 136, 139, 140, 141, or 142 wherein the solid tumor cancer is a metastatic cancer.

150. The method according to claim 143 wherein the tumor specific microorganisms express a suicide gene.

151. The method according to claim 150 wherein the tumor specific microorganisms express a suicide gene selected from the group consisting of p450 oxidoreductase, HSV thymidine kinase, *E. coli* cytosine deaminase, carboxypeptidase G2, β-glucuronidase, penicillin-V-amidase, penicillin-G-amidase, β-lactamase, β-glucosidase, nitroreductase and carboxypeptidase A.

152. The method according to claim 150 wherein expression of the suicide gene is controlled by a constitutive promoter, an inducible promoter, or a tumor cell specific promoter.

153. The method according to claim 150 wherein the suicide gene is encoded by the open reading frame of the insert of a plasmid selected from the group consisting of pTK-Sec3, pCD-Sec1 and pSP-SAD4-5.

154. The method according to claim 153 wherein the suicide gene is selected from the group consisting of HSV thymidine kinase and *E. coli* cytosine deaminase.

155. The method according to claim 135 or 136 wherein the effective amount is from about 1 to $1 \times 10^8$ c.f.u./kg.

156. The method according to claim 135 or 136 wherein the effective amount is from about 1 to $1 \times 10^2$ c.f.u./kg.

157. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, which amount is effective to reduce volume or inhibit growth of said solid tumor cancer, and wherein the tumor specific microorganisms are a tumor specific *Listeria monocytogenes*, wherein the single colony clone of an isolated population of tumor specific microorganisms is a single colony clone of an isolated population of super-infective, tumor specific microorganisms.

158. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, which amount is effective to reduce volume or inhibit growth of said solid tumor cancer, and wherein the tumor specific microorganisms are a tumor specific *Listeria monocytogenes*, wherein the tumor specific single colony clone is attenuated.

159. The method according to claim 158 wherein the single colony clone induces TNF-α expression in monocytes or macrophages from about 1 to about 75 percent compared to a single colony clone that is not attenuated.

160. The method according to claim 157 wherein the single colony clone of an isolated population of tumor specific microorganisms is produced by:

(a) exposing a mammal having a solid tumor cell cancer to a microorganism for for a time sufficient so that the population of microorganism can infect the tumor cells;

(b) isolating a population of super-infective, tumor specific microorganisms from the infected cell culture; and (c) culturing the population isolated in step (b) so that single colony clones are obtained.

161. The method according to claim 157 wherein the single colony clone of an isolated population of tumor specific microorganisms is produced by:

(a) exposing a microorganism to tumor cell conditioned medium for a time sufficient to allow the microorganism to chemotact towards the tumor cell conditioned medium;

(b) isolating a population of microorganisms which chemotacts towards the tumor cell conditioned medium; and (c) cultured the population isolated in step (b) so that single colony clones are obtained.

162. The method according to claim 157 wherein the single colony clone of an isolated population of super-infective, tumor specific microorganisms is produced by:

(a) exposing a mammal having a solid tumor cell cancer to a microorganism for for a time sufficient so that the population of microorganisms can infect the tumor cells;

(b) isolating a population of super-infective, tumor specific microorganisms from the infected tumor cells; and (c) culturing the population isolated in step (b) so that single colony clones are obtained.

163. The method according to claim 158 wherein the single colony clone of an isolated population of tumor specific microorganisms is produced by:

(a) exposing a microorganism to tumor cell conditioned medium for a time sufficient to allow the microorganism to chemotact towards the tumor cell conditioned medium;

(b) isolating a population of microorganisms which chemotacts towards the tumor cell conditioned medium; and (c) culturing the population isolated in step (b) so that single colony clones are obtained.

164. The method according to claim 157 or 158 wherein the single colony clone is genetically engineered.

165. The method according to claim 157 or 158 wherein the effective amount is from about 1 to $1 \times 10^8$ c.f.u./kg.

166. The method according to claim 157 or 158 wherein the effective amount is from about 1 to $1 \times 10^2$ c.f.u./kg.

167. The method according to claim 160, 161, 162 or 163 further comprising:

subjecting the microorganism to mutagenesis before step (a).

168. The method according to claim 160, 161, 162 or 163 further comprising:

(d) repeating steps (a) and (b) a desired number of times before step (c).

169. The method according to claim 157, 158, 160, 161, 162 or 163 wherein the solid tumor cancer is melanoma cancer.

170. The method according to claim 157, 158, 160, 161, 162 or 163 wherein the solid tumor cancer is colon carcinoma cancer.

171. The method according to claim 157, 158, 169, 161, 162 or 163 wherein the solid tumor cancer is selected from the group consisting of lung cancer, liver cancer, kidney cancer, prostate cancer and breast cancer.

172. The method according to claims 157, 158, 160, 161, 162, or 163 wherein the solid tumor cancer is a metastatic cancer.

173. The method according to claim 164 wherein the single colony clone expresses a suicide gene.

174. The method according to claim 173 wherein expression of the suicide gene is controlled by a constitutive promoter, an inducible promoter, or a tumor cell specific promoter.

175. The method according to claim 173 wherein the single colony clone expresses a suicide gene selected from the group consisting of p450 oxidoreductase, HSV thymidine kinase, *E. coli* cytosine deaminase, carboxypeptidase G2, β-glucuronidase, penicillin-V-amidase, penicillin-G-amidase, β-lactamase, β-glucosidase, nitroreductase and carboxypeptidase A.

176. The method according to claim 173 wherein the suicide gene is encoded by the open reading frame of the insert of a plasmid selected from the group consisting of pTK-Sec3, pCD-Sec1 and pSP-SAD4-5.

177. The method according to claim 176 wherein the suicide gene is selected from the group consisting of HSV thymidine kinase and *E. coli* cytosine deaminase.

178. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by an inducible promoter, which amount is effective to reduce volume or inhibit growth of said solid tumor cancer, and wherein the tumor specific microorganims are a tumor specific *Listeria monocytogenes.*

179. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms, which grows under both aerobic and anaerobic conditions, and wherein the single colony clone expresses a suicide gene which gene is controlled by a bacterial promoter that is activated in specified tumor cells, which amount is effective to reduce volume or inhibit growth of said solid tumor cancer, and wherein the tumor specific microorganisms are a tumor specific *Listeria monocytogenes.*

180. A diagnostic kit comprising an effective amount of a tumor-specific microorganism and instructions for use for in vitro diagnosis of a solid tumor cancer, wherein the tumor specific microorganism is a tumor specific *Listeria monocytogenes.*

181. The diagnostic kit according to claim 180 wherein the tumor-specific microorganism is a super-infective, tumor-specific microorganism.

182. The diagnostic kit according to claim 180 further comprising non-cancerous counterpart control cells.

183. The diagnostic kit according to claim 181 wherein the microorganism is genetically engineered.

184. The method according to claim 166 wherein the tumor specific microorganisms are auxotrophic mutants.

185. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by a constitutive promoter, which amount is effective to reduce volume or inhibit growth of said solid tumor cancer, and wherein the tumor specific microorganisms are a tumor specific Shigella species.

186. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by a constitutive promoter, which amount is effective to reduce volume or inhibit growth of said solid tumor cancer, and wherein the tumor specific microorganisms are a tumor specific Streptococcus species genetically engineered to express a suicid gene.

187. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by a constitutive promoter, which amount is effective to reduce volume or inhibit growth of said solid tumor cancer, and wherein the tumor specific microorganisms are a tumor specific Streptococcus species, and wherein the administration is oral, topical, intravenous, intraperitoneal, subcutaneous, or intramuscular.

188. A method for reducing volume or inhibiting growth of a solid tumor cancer, comprising: administering an amount of a single colony clone of an isolated population of tumor specific microorganisms, which replicates preferentially in the tumor after administration, to a patient having a solid tumor cancer, wherein the single colony clone of an isolated population of tumor specific microorganisms grows under both aerobic and anaerobic conditions, and wherein the single colony clone expresses a suicide gene which gene is controlled by a constitutive promoter, which amount is effective to reduce volume or inhibit growth of said solid tumor cancer, and wherein the tumor specific microorganisms are a tumor specific *Listeria monocytogenes.*

\* \* \* \* \*

UNITED STATES PATENT AND TRADEMARK OFFICE
CERTIFICATE OF CORRECTION

PATENT NO. : 6,685,935 B1
DATED : February 3, 2004
INVENTOR(S) : Pawelek et al.

It is certified that error appears in the above-identified patent and that said Letters Patent is hereby corrected as shown below:

Column 74,
Lines 28-29, the ATCC Accession Nos. for Population #14028$^{pop-1}$ and Population #14028$^{pop-2}$, "55681" and "55682," respectively, need to be interchanged.

Signed and Sealed this

Twenty-seventh Day of December, 2005

JON W. DUDAS
*Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 1:

GATCATGCAT GGCTTCGTAC CCCGGCC                                                27

(2) INFORMATION FOR SEQ ID NO: 2:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

CTAGATGCAT CAGTGGCTAT GGCAGGGC                                               28

(2) INFORMATION FOR SEQ ID NO: 3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

CTAGACTAGT TTGTCAATAA TGACAACACC C                                           31

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GATCGGATCC TTGCCCGGCG CGGCGGCCTG                                             30

(2) INFORMATION FOR SEQ ID NO: 5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

```
CTAGAAGCTT ATAAGGGTTG ATCTTTGTTG TC                           32
```

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

```
GTACGATATC CAGAACGATG TGCATAGCCT G                            31
```

(2) INFORMATION FOR SEQ ID NO: 7:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO: 7:

```
Tyr Thr Ser Gly Tyr Ala His Arg Ser
1               5
```

(2) INFORMATION FOR SEQ ID NO: 8:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (xi) SEQUENCE DESCRIPTION: SEQ ID NO: 8:

```
Ser Gly Tyr Arg Ile Pro
1               5
```

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

```
GATCATGCAT GTGGAGGCTA ACAGT                                   25
```

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

```
CTAGATGCAT CAGACAGCCG CTGCGAAGGC                              30
```